(12) United States Patent
Willoughby et al.

(10) Patent No.: US 9,700,459 B2
(45) Date of Patent: Jul. 11, 2017

(54) APPARATUSES, TOOLS AND KITS RELATING TO FLUID MANIPULATION TREATMENTS OF PARANASAL SINUSES

(71) Applicant: SINOPSYS SURGICAL, INC., Boulder, CO (US)

(72) Inventors: Brian James Willoughby, Denver, CO (US); Christopher Lee Oliver, Lakewood, CO (US); Harry Ross, Boulder, CO (US); William W. Cimino, Louisville, CO (US)

(73) Assignee: Sinopsys Surgical, Inc., Boulder, CO (US)

( * ) Notice: Subject to any disclaimer, the term of this patent is extended or adjusted under 35 U.S.C. 154(b) by 0 days.

(21) Appl. No.: 15/027,406

(22) PCT Filed: Oct. 16, 2014

(86) PCT No.: PCT/US2014/060891
§ 371 (c)(1),
(2) Date: Apr. 5, 2016

(87) PCT Pub. No.: WO2015/069433
PCT Pub. Date: May 14, 2015

(65) Prior Publication Data
US 2016/0250070 A1 Sep. 1, 2016

Related U.S. Application Data

(60) Provisional application No. 61/891,710, filed on Oct. 16, 2013.

(51) Int. Cl.
*A61F 9/007* (2006.01)

(52) U.S. Cl.
CPC . *A61F 9/00772* (2013.01); *A61M 2210/0618* (2013.01); *A61M 2210/0681* (2013.01)

(58) Field of Classification Search
CPC .. A61M 2039/0279; A61M 2039/0294; A61M 2210/0618; A61M 2210/0681
See application file for complete search history.

(56) References Cited

U.S. PATENT DOCUMENTS

| 3,726,284 A | 4/1973 | Parker |
| 3,948,272 A | 4/1976 | Guibor |

(Continued)

FOREIGN PATENT DOCUMENTS

| EP | 0631793 A1 | 1/1995 |
| FR | 2813522 A1 | 3/2002 |

(Continued)

OTHER PUBLICATIONS

Bagdonaite, Laura, M.D. et al. "Twelve-Year Experience of Lester Jones Tubes—Results and Comparison of 3 Different Tube Types", Opthalmic Plastic Reconstructive Surgery (2015) vol. 31, No. 5., pp. 352-356.

(Continued)

*Primary Examiner* — Tatyana Zalukaeva
*Assistant Examiner* — Kai Weng
(74) *Attorney, Agent, or Firm* — Marsh Fischmann & Breyfogle, LLP

(57) ABSTRACT

Apparatuses, tools and kits are directed to fluid manipulations in relation to a paranasal sinus through a paranasal sinus access implant device (906) that provides fluid communication between the lacrimal apparatus in the orbit and a paranasal sinus. An implant device has a proximal head and a conduit distal of the head, with the conduit having a first longitudinal portion having a larger minimum wall thickness than a minimum wall thickness of a second a second longitudinal portion of the conduit located distal of the first longitudinal portion. A paranasal sinus fluid manipulation tool (900) has an engagement structure (904) insert- (Continued)

able into the palpebral fissure to engage a head of the implant device.

20 Claims, 22 Drawing Sheets

(56) References Cited

U.S. PATENT DOCUMENTS

| | | |
|---|---|---|
| 4,915,684 A | 4/1990 | MacKeen et al. |
| 4,921,485 A | 5/1990 | Griffiths |
| 5,169,386 A | 12/1992 | Becker et al. |
| 5,345,948 A | 9/1994 | O'Donnell, Jr. |
| 6,041,785 A | 3/2000 | Webb |
| 6,083,188 A | 7/2000 | Becker |
| 6,629,533 B1 | 10/2003 | Webb et al. |
| 6,878,165 B2 | 4/2005 | Makino |
| 6,966,888 B2 | 11/2005 | Cullen et al. |
| 7,156,821 B2 | 1/2007 | Dohlman |
| 7,169,163 B2 | 1/2007 | Becker |
| 7,361,168 B2 | 4/2008 | Makower et al. |
| 7,410,480 B2 | 8/2008 | Muni et al. |
| 7,419,497 B2 | 9/2008 | Muni et al. |
| 7,462,175 B2 | 12/2008 | Chang et al. |
| 7,500,971 B2 | 3/2009 | Chang et al. |
| D590,935 S | 4/2009 | Becker |
| 7,547,323 B2 | 6/2009 | Lavigne |
| 7,559,925 B2 | 7/2009 | Goldfarb et al. |
| 7,641,644 B2 | 1/2010 | Chang et al. |
| 7,645,272 B2 | 1/2010 | Chang et al. |
| 7,654,997 B2 | 2/2010 | Makower et al. |
| 7,713,255 B2 | 5/2010 | Eaton et al. |
| 7,720,521 B2 | 5/2010 | Chang et al. |
| 7,727,186 B2 | 6/2010 | Makower et al. |
| 7,727,226 B2 | 6/2010 | Chang et al. |
| 7,758,534 B2 | 7/2010 | Pearson |
| 7,771,409 B2 | 8/2010 | Chang et al. |
| 7,785,315 B1 | 8/2010 | Muni et al. |
| 7,803,150 B2 | 9/2010 | Chang et al. |
| 7,846,124 B2 | 12/2010 | Becker |
| 9,022,967 B2 | 5/2015 | Oliver et al. |
| 9,308,358 B2 | 4/2016 | Oliver et al. |
| 2002/0032444 A1 | 3/2002 | Mische |
| 2002/0107579 A1 | 8/2002 | Makino |
| 2004/0077989 A1 | 4/2004 | Goode et al. |
| 2004/0116958 A1 | 6/2004 | Gopferich et al. |
| 2004/0204704 A1 | 10/2004 | Tamplenizza et al. |
| 2004/0254516 A1 | 12/2004 | Murray et al. |
| 2005/0159730 A1* | 7/2005 | Kathrani ............ A61B 17/3421 604/541 |
| 2005/0197614 A1 | 9/2005 | Pritchard et al. |
| 2005/0240143 A1 | 10/2005 | Dohlman |
| 2005/0245906 A1 | 11/2005 | Makower et al. |
| 2005/0273033 A1 | 12/2005 | Grahn et al. |
| 2006/0063973 A1 | 3/2006 | Makower et al. |
| 2006/0142736 A1 | 6/2006 | Hissink et al. |
| 2006/0251575 A1 | 11/2006 | Morgenstern |
| 2006/0276738 A1 | 12/2006 | Becker |
| 2007/0005120 A1 | 1/2007 | Villacampa et al. |
| 2007/0112291 A1 | 5/2007 | Borgesen |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0255263 A1 | 11/2007 | Sugimoto |
| 2007/0269487 A1 | 11/2007 | de Juan et al. |
| 2007/0276314 A1 | 11/2007 | Becker |
| 2007/0282305 A1 | 12/2007 | Goldfarb et al. |
| 2007/0293726 A1 | 12/2007 | Goldfarb et al. |
| 2007/0293727 A1 | 12/2007 | Goldfarb et al. |
| 2007/0299422 A1* | 12/2007 | Inganas ............ A61B 17/0057 604/508 |
| 2008/0082037 A1 | 4/2008 | Pearson |
| 2008/0097154 A1 | 4/2008 | Makower et al. |
| 2008/0097354 A1 | 4/2008 | Lavigne |
| 2008/0097514 A1 | 4/2008 | Chang et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0125805 A1 | 5/2008 | Mische |
| 2008/0132938 A1 | 6/2008 | Chang et al. |
| 2008/0154237 A1 | 6/2008 | Chang et al. |
| 2008/0154250 A1 | 6/2008 | Makower et al. |
| 2008/0195041 A1 | 8/2008 | Goldfarb et al. |
| 2008/0228085 A1 | 9/2008 | Jenkins et al. |
| 2008/0234720 A1 | 9/2008 | Chang et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0306428 A1* | 12/2008 | Becker ............... A61F 9/00772 604/8 |
| 2008/0319424 A1 | 12/2008 | Muni et al. |
| 2009/0005763 A1 | 1/2009 | Makower et al. |
| 2009/0028923 A1 | 1/2009 | Muni et al. |
| 2009/0030274 A1 | 1/2009 | Goldfarb et al. |
| 2009/0036818 A1 | 2/2009 | Grahn et al. |
| 2009/0099626 A1 | 4/2009 | de Juan, Jr. et al. |
| 2009/0104248 A1 | 4/2009 | Rapacki et al. |
| 2009/0105749 A1 | 4/2009 | de Juan et al. |
| 2009/0187098 A1 | 7/2009 | Makower et al. |
| 2009/0198216 A1 | 8/2009 | Muni et al. |
| 2009/0204142 A1 | 8/2009 | Becker et al. |
| 2009/0221988 A1 | 9/2009 | Ressemann et al. |
| 2009/0240112 A1 | 9/2009 | Goldfarb et al. |
| 2009/0240237 A1 | 9/2009 | Goldfarb et al. |
| 2009/0275882 A1 | 11/2009 | Lavigne |
| 2009/0275903 A1 | 11/2009 | Lavigne |
| 2009/0281621 A1 | 11/2009 | Becker |
| 2009/0312745 A1 | 12/2009 | Goldfarb et al. |
| 2010/0034870 A1 | 2/2010 | Sim et al. |
| 2010/0042046 A1 | 2/2010 | Chang et al. |
| 2010/0076269 A1 | 3/2010 | Makower et al. |
| 2010/0099946 A1 | 4/2010 | Jenkins et al. |
| 2010/0100181 A1 | 4/2010 | Makower et al. |
| 2010/0106255 A1 | 4/2010 | Dubin |
| 2010/0114066 A1 | 5/2010 | Makower et al. |
| 2010/0121308 A1 | 5/2010 | Muni et al. |
| 2010/0174138 A1 | 7/2010 | Chang et al. |
| 2010/0174308 A1 | 7/2010 | Chang et al. |
| 2010/0198247 A1 | 8/2010 | Chang et al. |
| 2010/0210901 A1 | 8/2010 | Makower et al. |
| 2010/0268245 A1 | 10/2010 | Chang et al. |
| 2010/0274204 A1 | 10/2010 | Rapacki et al. |
| 2010/0274259 A1 | 10/2010 | Yaron et al. |
| 2010/0298862 A1 | 11/2010 | Chang et al. |
| 2010/0317969 A1 | 12/2010 | Becker |
| 2011/0004057 A1 | 1/2011 | Goldfarb et al. |
| 2011/0060214 A1 | 3/2011 | Makower |
| 2011/0105989 A1 | 5/2011 | Becker |
| 2011/0112512 A1 | 5/2011 | Muni et al. |
| 2011/0224680 A1 | 9/2011 | Barker |
| 2011/0276131 A1 | 11/2011 | De Juan, Jr. et al. |
| 2012/0089071 A1 | 4/2012 | Oliver et al. |
| 2012/0245539 A1 | 9/2012 | Zarins et al. |
| 2013/0030545 A1 | 1/2013 | Gross et al. |
| 2013/0231693 A1 | 9/2013 | Edgren et al. |
| 2013/0274647 A1 | 10/2013 | Oliver et al. |
| 2014/0012309 A1 | 1/2014 | Keith et al. |
| 2015/0065941 A1 | 3/2015 | Ross et al. |
| 2015/0231376 A1 | 8/2015 | Willoughby et al. |

FOREIGN PATENT DOCUMENTS

| | | |
|---|---|---|
| WO | 2006013306 A1 | 2/2006 |
| WO | 2008045242 A2 | 4/2008 |
| WO | 2009035562 A2 | 3/2009 |
| WO | 2009145755 A1 | 12/2009 |
| WO | 2010096822 A2 | 8/2010 |
| WO | 2010111528 A2 | 9/2010 |
| WO | 2011066479 A1 | 6/2011 |

(56) References Cited

FOREIGN PATENT DOCUMENTS

| WO | 2012048278 A2 | 4/2012 |
|---|---|---|
| WO | 2013154843 A1 | 10/2013 |
| WO | 2014116980 A1 | 7/2014 |

OTHER PUBLICATIONS

Sadeghi, Nader, M.D. et al. Transnasal Endoscopic Medial Maxillectomy for Inverting Papilloma. Laryngoscope (2003) 113:749-753.

Mangan, BG et al. Bilateral Nasolacrimal Duct Atresia in a Cria. Veterinary Opthalmology (2008) 11, 1, 49-54.

Giuliano, EA et al. Dacryocystomaxillorhinostomy for Chronic Dacryocystitis in a Dog. Veterinary Opthalmology (2006) 9, 2, 89-94.

Wilson, DG et al. Surgical Reconstruction of the Nasolacrimal System in the Horse. Equine Veterinary Science (1991) vol. II, No. 4, pp. 232-234.

Steinmetz, A et al. Surgical Removal of a Dermoid Cyst From the Bony Part of Thenasolacrimal Duct in a Scottish Highland Cadle Heifer. Veterinary Opthalmology (2009) 12, 4, 259-262.

McIlnay, TR et al. Use of Canaliculorhinostomy for Repair of Nasolacrimal Duct Obstruction in a Horse. JAVMA (2001) vol. 218, No. 8. Scientific Reports: Clinical Report. 1323-1324.

Gionfriddo JR. The nasolacrimal system. In: Textbook of Small Animal Surgery 3rd edition. 2003, Slatter OM ed. Saunders, Philadelphia PA, pp. 1356-1358.

* cited by examiner

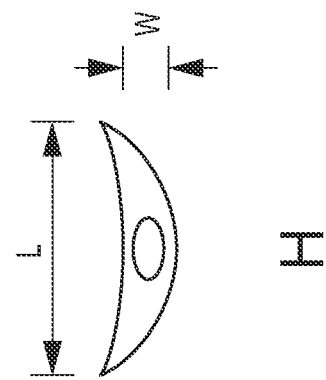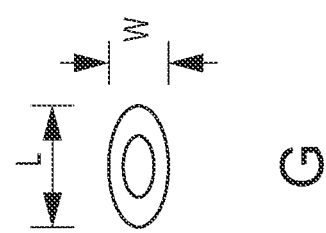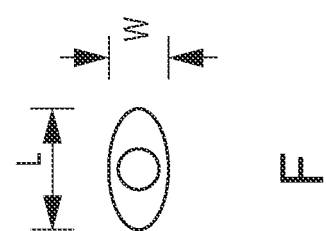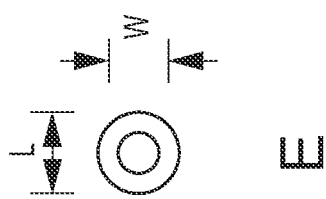
FIG.9

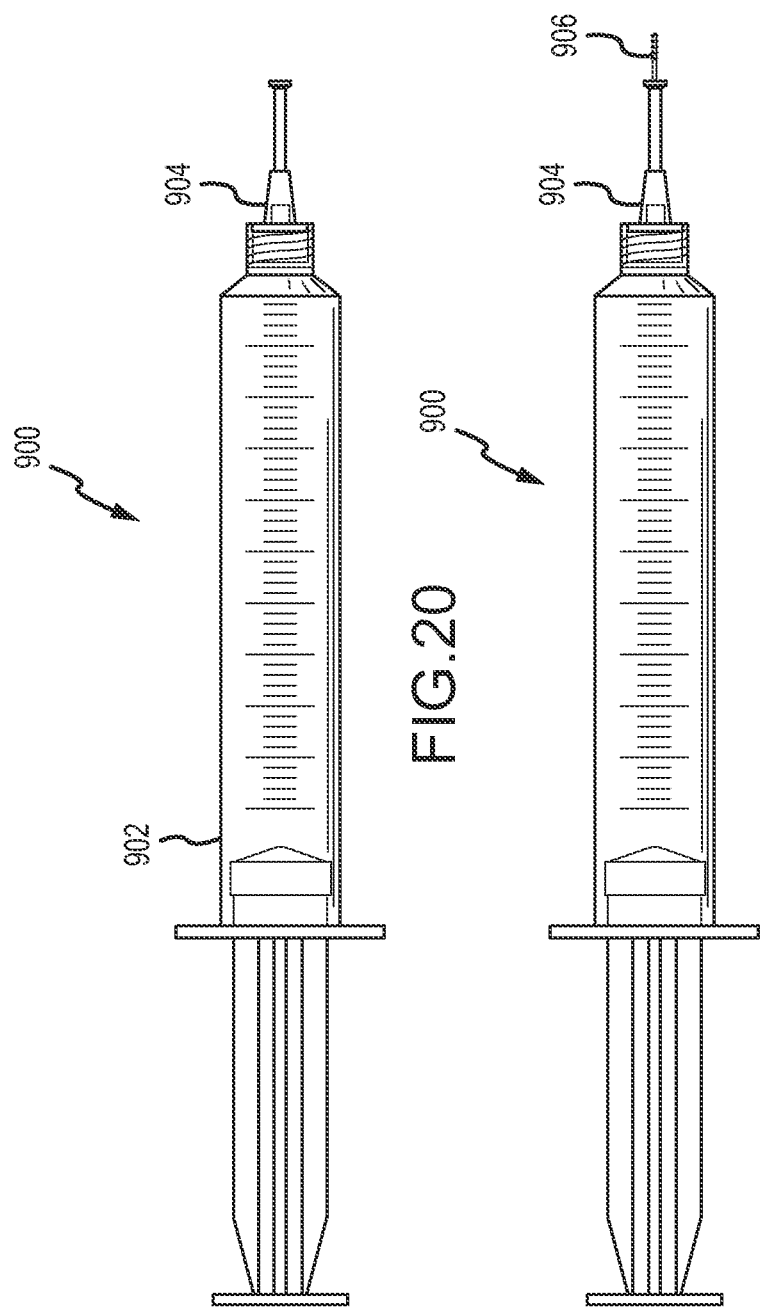

APPARATUSES, TOOLS AND KITS RELATING TO FLUID MANIPULATION TREATMENTS OF PARANASAL SINUSES

CROSS-REFERENCE TO RELATED APPLICATIONS

This application claims the benefit of U.S. provisional patent application No. 61/891,710 entitled "APPARATUSES, TOOLS, KITS AND METHODS RELATING TO FLUID MANIPULATION TREATMENTS OF PARANASAL SINUSES" filed Oct. 16, 2013, the entire contents of which are incorporated herein by reference.

This application incorporates by reference each and every portion of the following: international patent application no. PCT/US2011/055456 entitled "IMPLANT DEVICE, TOOL, AND METHODS RELATING TO TREATMENT OF PARANASAL SINUSES" filed Oct. 7, 2011; U.S. nonprovisional patent application Ser. No. 13/225,213 entitled "IMPLANT DEVICE, TOOL, AND METHODS RELATING TO TREATMENT OF PARANASAL SINUSES" filed Sep. 2, 2011; U.S. provisional patent application No. 61/528,058 entitled "IMPLANT DEVICE, TOOL, AND METHODS RELATING TO TREATMENT OF PARANASAL SINUSES" filed Aug. 26, 2011; U.S. provisional patent application No. 61/404,716 entitled "METHODS AND TOOLS FOR TREATMENT AND PREVENTION OF SINUSITIS" filed Oct. 8, 2010; U.S. provisional patent application No. 61/623,022 entitled "IMPLANTATION TOOLS, TOOL ASSEMBLIES, KITS AND METHODS" filed Apr. 11, 2012; international patent application no. PCT/US2013/03447 entitled "IMPLANTATION TOOLS, TOOL ASSEMBLIES, KITS AND METHODS" filed Mar. 28, 2013; U.S. provisional patent application No. 61/757,046 entitled "IMPLANT DEVICE, METHOD AND KIT FOR IMPLANTATION BETWEEN THE LACRIMAL SYSTEM AND A PARANASAL SINUS" filed Jan. 25, 2013; and U.S. provisional patent application No. 61/891,250 entitled "PARANASAL SINUS ACCESS IMPLANT DEVICES AND RELATED TOOLS, METHODS AND KITS" filed Oct. 15, 2013.

FIELD OF THE INVENTION

The invention relates to treatment of conditions of the paranasal sinuses, including with respect to apparatuses, tools, kits and methods.

BACKGROUND OF THE INVENTION

In the United States alone, 35 million people a year are treated for sinus infections, or sinusitis, and 7 million of those will suffer from chronic sinusitis and will have minimal response to prescription drug therapies. Current surgical interventions may be expected to, at best, offer only moderate symptomatic improvement but no cure.

Current drug therapies include oral administration as pills and nasal topical administration, neither of which is conducive to delivering adequate concentration of medication to the involved paranasal sinus. In addition to medication, frequent sinus irrigation can be helpful in flushing out debris, irritants and obstructing viscous fluids, but patients are generally not able to adequately perform this procedure at home.

For patients with particularly severe symptoms, surgical drainage may be the only additional option. An early surgical procedure was the Caldwell-Luc procedure, which involves creating a permanent fistula from the base of the paranasal sinus into the oral cavity above the front upper incisors. More recently, other surgical access points to the paranasal sinuses have been attempted. A variety of endoscopic techniques have been developed that access the paranasal sinuses through the nose, including functional endoscopic sinus surgery (FESS) and balloon sinuplasty. All attempt to increase drainage, but utilize different routes or tools. Surgical formation of a fistula between the lacrimal apparatus and a paranasal sinus has been identified as a technique to provide direct access to the paranasal sinus, and through which a variety of medical treatments and medical procedures may be directed to the paranasal sinus. None of these surgical approaches has yet achieved wide-spread acceptance or success, and millions of chronic sinusitis patients continue to suffer long-term disability and discomfort. There continues to be a need for effective and convenient techniques to administer drugs directed to treatment of conditions of the paranasal sinuses.

SUMMARY OF INVENTION

Paranasal sinus access implant devices may be configured to be implanted in a human to provide fluid access to a paranasal sinus through an internal passage of such a paranasal sinus access implant device, with the internal passage being accessible through an opening in a head of the paranasal sinus access implant device. The head may be configured to be disposed in the orbit, for example between the medial canthus and the medial side of the adjacent eyeball, when the paranasal sinus access implant device is implanted to provide fluid access to a paranasal sinus. Such paranasal sinus access implant devices have significant potential for performance of medical procedures and treatments of paranasal sinuses, but such potential has not yet been realized. Treatment compositions may be delivered to a paranasal sinus through such an implant device by administering eye drops that may then flow through the implant device to a paranasal sinus. Fluid administrations may also be made by inserting a needle through the implant device to inject fluid directly into the paranasal sinus and medical procedures may involve passing a medical device through the implant device and into the paranasal sinus. However, such mechanical interactions with the implant device have potential to structurally damage the implant device or to dislodge the implant device or disrupt the anchoring of the implant device in surrounding tissue. Various aspects of this disclosure relate to fluid manipulations through such paranasal sinus access implant devices in a manner that may reduce the potential for problems associated with mechanical interactions of the types noted.

A first aspect of the disclosure involves a paranasal sinus fluid manipulation tool to manipulate fluid through a paranasal sinus access implant device, for example of a type such as noted above. The paranasal sinus fluid manipulation tool comprises:
  a fluid container;
  a paranasal sinus fluid connection engagement structure configured for insertion into the palpebral fissure to make engagement with a head of a said paranasal sinus access implant device when implanted to fluidly connect the fluid container with the internal passage of the said paranasal sinus access implant device; and
  a fluid transmission structure configured to transmit fluid between the fluid container and the paranasal sinus access implant device when the paranasal sinus fluid connection engagement structure is in the engagement with the head of the paranasal sinus access implant device.

The paranasal sinus fluid manipulation tool may be manipulable to manipulate fluid to perform at least one of the following fluid manipulations when the said paranasal sinus access implant device is implanted and the paranasal sinus fluid connection engagement structure is in the engagement with the head: (i) introducing fluid from the fluid container into an internal passage of the said paranasal sinus implant device for delivery from the internal passage to a paranasal sinus and (ii) applying suction to the internal passage for aspiration of fluid from a paranasal sinus through the internal passage and into the fluid container. As will be appreciated, the palpebral fissure is an anatomical opening between eyelids, also referred to as the rima palpebrarum. The fluid container, paranasal sinus fluid connection engagement structure and fluid transmission structure may be provided in a kit with the fluid container, paranasal sinus fluid connection engagement structure and fluid transmission structure as provided in the kit being assembled or assemblable as such a paranasal sinus fluid manipulation tool. Such a kit may or may not include one or more additional components in the kit.

A second aspect of the disclosure involves a paranasal sinus fluid treatment apparatus including a paranasal sinus access implant device, for example of a type such as noted above. The paranasal sinus fluid treatment apparatus includes a paranasal sinus fluid manipulation tool, the paranasal sinus fluid manipulation tool comprising:

a fluid container;
a paranasal sinus fluid connection engagement structure in engagement with a head of the paranasal sinus access implant device to fluidly connect the paranasal sinus fluid manipulation tool with the paranasal sinus access implant device, the paranasal sinus fluid connection engagement structure being configured to be disposed in the palpebral fissure; and
a fluid transmission structure configured to transmit fluid between the fluid container and the paranasal sinus access implant device.

The paranasal sinus fluid manipulation tool may be manipulable to perform at least one of the following fluid manipulations when the paranasal sinus access implant device is implanted to provide fluid access to a paranasal sinus: (i) introduction of fluid from the fluid container into an internal passage of the paranasal sinus implant device for delivery to a paranasal sinus and (ii) applying suction to the internal passage for aspiration of fluid from a paranasal sinus through the internal passage.

A third aspect of the disclosure involves a fluid transmission attachment for use with a syringe to manipulate fluid through a paranasal sinus access implant device, for example of a type such as noted above. The syringe attachment comprises:

a connection structure configured to connect the fluid transmission attachment with a syringe;
a paranasal sinus fluid connection engagement structure configured for insertion into the palpebral fissure for engagement with a head of a said paranasal sinus access implant device when implanted; and
a fluid conduit between the connection structure and the paranasal sinus fluid connection engagement structure to conduct fluid from a fluid container of the syringe to an internal passage of the said paranasal sinus access implant device when the syringe and fluid transmission attachment are connected through the connection structure and the paranasal sinus fluid connection engagement structure is in the engagement with the head of the said paranasal sinus access implant device.

The fluid transmission attachment may be configured to transmit fluid between the syringe and the internal passage of the paranasal sinus access implant device as manipulated by a syringe to perform at least one of the following fluid manipulations when the said paranasal sinus access implant device is implanted, the fluid transmission attachment and the syringe are connected through the connection structure and the paranasal sinus fluid connection engagement structure is in the engagement with the head: (i) introducing fluid from the fluid container of the syringe into the internal passage for delivery from the internal passage to a paranasal sinus and (ii) applying suction to the internal passage for aspiration of fluid from a paranasal sinus through the internal passage and into the fluid container of the syringe.

A fourth aspect of the disclosure involves a kit useful for accessing and performing fluid manipulations in relation to a paranasal sinus. The kit, comprises a paranasal sinus access implant device, for example of a type such as noted above, and a paranasal sinus fluid manipulation tool or components assemblable into such a paranasal sinus fluid manipulation tool, for example of a type of the first aspect of the disclosure. The paranasal sinus access implant device and the paranasal sinus fluid manipulation tool may be configurable to perform at least one of the following fluid manipulations when a paranasal sinus fluid connection engagement structure of the paranasal sinus fluid manipulation tool is in engagement with a head of the paranasal sinus access implant device: (i) introducing fluid from a fluid container of the paranasal sinus fluid manipulation tool into an internal passage of the paranasal sinus access implant device and (ii) applying suction to the internal passage for aspiration of fluid from the internal passage.

A fifth aspect of the disclosure involves a method for manipulating fluid in relation to a paranasal sinus using a paranasal sinus fluid treatment apparatus, for example such as of a type of the second aspect of the disclosure, and a paranasal sinus access implant device, for example of a type as noted above. With the paranasal sinus access implant device implanted in a human with a head of the paranasal sinus access implant device disposed in the orbit of the human (e.g., between the medial canthus and the medial side of an adjacent eyeball), the method may include manipulating the fluid manipulation apparatus to perform one of the following manipulations: (i) introduction of fluid from the fluid container into an internal passage of the paranasal sinus access implant device for delivery to the paranasal sinus and (ii) applying suction to the internal passage for aspiration of fluid from paranasal passage through the internal passage.

A sixth aspect of the disclosure involves a method for manipulating fluid in relation to a paranasal sinus through a paranasal sinus access implant device, for example of a type as noted above, implanted in a human to provide fluid access to a paranasal sinus with a head of the implant device being disposed in an orbit of the human. The method comprises engaging a paranasal sinus fluid manipulation tool, for example of a type such as of the first aspect of the disclosure, with a head of the paranasal sinus fluid access implant device disposed in the orbit to make an engagement between a paranasal sinus fluid connection engagement structure of the paranasal sinus fluid manipulation tool and the head. The paranasal sinus fluid manipulation tool may then be manipulated to perform one of the following fluid manipulations while the paranasal sinus fluid connection engagement structure is in the engagement with the head: (i) introducing fluid from a fluid container of the paranasal sinus fluid manipulation tool into an internal passage of the paranasal sinus access implant device for delivery from the internal passage to a paranasal sinus and (ii) applying suction to the internal passage for aspiration of fluid from a paranasal sinus through the internal passage and into the fluid container.

A number of feature refinements and additional features are applicable to any one or more of these or other aspects of the disclosure. These feature refinements and additional features may be used individually or in any combination within the subject matter of any such aspects. As such, each of the following features may be, but are not required to be, used within any other feature or combination of features in relation to the same aspect or any other aspect of the disclosure.

For brevity, paranasal sinus access implant devices are referred to herein as simply implant devices, paranasal sinus fluid manipulation tools are referred to herein as simply fluid manipulation tools, paranasal sinus fluid connection engagement structures are referred to herein as simply engagement structures, and paranasal sinus fluid treatment apparatuses are referred to herein as simply fluid treatment apparatuses.

Various feature refinements and additional features are applicable to the paranasal sinus fluid connection engagement structure of the paranasal sinus fluid manipulation tool.

An engagement structure may have an insertion cross-section configured (e.g., sized and shaped) to permit the engagement structure to be easily inserted into and disposed within the palpebral fissure to encounter and engage with a head of a paranasal sinus access implant device. The insertion cross-section identifies a minimum area through which the engagement structure may be inserted to encounter and engage with a head of an implant device when the implant device is implanted with the head of the implant device disposed in the orbit between the medial canthus and the medial side of an adjacent eyeball. In that regard, the insertion cross-section may have an elongated shape with a length aspect configured to fit between the a top and bottom of the palpebral fissure, between opened eyelids, and a narrower width aspect configured to fit between the medial canthus and the medial side of the adjacent eyeball, and the insertion cross-section may be configured to orient with respect to and engage with a corresponding elongated configuration of the head of the implant device. The insertion cross-section of the engagement structure may be configured to be positionable in (e.g., passable through) a first rectangular area having a first length dimension equal to or no larger than 12 millimeters, 10 millimeters, 8 millimeters or 7 millimeters and a first width dimension equal to or no larger than 8 millimeters, 7 millimeters, 6 millimeters, 5 millimeters, 3.5 millimeters or 3 millimeters, wherein the first length dimension is larger than the first width dimension. Such an insertion cross-section may be such as to not be positionable in (e.g., not passable through) a second rectangular area having a second length dimension that is no larger than, and may be smaller than, the first length dimension and that is equal to or at least as large as 3 millimeters, 4 millimeters, 5 millimeters or 6 millimeters and a second width dimension that is smaller than the first width dimension and that is equal to or at least as large as 1.5 millimeters, 2 millimeters, 2.5 millimeters or 3 millimeters, wherein the second length dimension is larger than the second width dimension. The insertion cross-section of the engagement structure may be configured to be positionable in (e.g., passable through) a first elliptical area having a first major axis dimension equal to or no larger than 12 millimeters, 10 millimeters, 8 millimeters or 7 millimeters and a first minor axis dimension equal to or no larger than 8 millimeters, 7 millimeters, 6 millimeters, 5 millimeters, 3.5 millimeters or 3 millimeters. Such an insertion cross-section may be such as to not be positionable in (e.g., not passable through) a second elliptical area having a second major axis dimension that is no larger than, and may be smaller than, the first major axis dimension and that is equal to or at least as large as 3 millimeters, 4 millimeters, 5 millimeters or 6 millimeters and a second minor axis dimension that is smaller than the first minor axis dimension and that is equal to or at least as large as 1.5 millimeters, 2 millimeters, 2.5 millimeters or 3 millimeters. The insertion cross-section may have an aspect ratio of length to width of at least 1.25:1, at least 1.5:1, at least 1.75:1, at least 2:1 or at least 2.5:1. Such an aspect ratio may be smaller than 5:1, smaller than 4:, smaller than 3:1 or smaller than 2.5:1. The length of the insertion cross-section refers to the largest separation distance between opposing points on the perimeter of the cross-section and the width refers to the maximum separation distance between opposing points on the perimeter of the cross-section that are on a line perpendicular to the length dimension. The insertion cross-section may have an oval shape, which generally refers to an elongated shape with at least curved perimeter ends. Such an oval shape may have one or even two axes of symmetry, in which case such two axes of symmetry may be perpendicular axes. An oval shape includes an ellipse. In the case of the insertion cross-section being an ellipse, the length of the insertion cross-section is the major axis of the ellipse and the width is the minor axis of the ellipse.

The paranasal sinus fluid connection engagement structure may include a receptacle for receiving the head when the engagement structure and the head are in engagement. The receptacle may include a feature, such as a shoulder or other geometric design feature, that acts as an insertion stop that limits a depth within the receptacle to which the head is receivable in the receptacle in the engagement. Such a feature may in the engagement limit receipt of the head to a depth within the receptacle of no more than 5 millimeters, no more than 4 millimeters, no more than 3 millimeters, no more than 2 millimeters or no more than 1 millimeter. When in the engagement, the head may be receivable within the receptacle to a depth in the receptacle of at least 0.1 millimeter, at least 0.25 millimeter, at least 0.5 millimeter at least 0.75 millimeter, or more. Such an insertion stop feature may beneficially help prevent inadvertent advancement of the head into the receptacle to a depth at which the engagement structure excessively pushes into adjacent conjunctival tissue in a manner that may be detrimental to the integrity of the anchoring of the implant device in surrounding tissue through which the implant device extends into the paranasal sinus (e.g., the firmness of the anchoring of the implant within a fistula through which the implant device extends). The receptacle may have a receiving geometry that promotes alignment between the engagement structure and the head for effective fluid communication with the internal passage of the implant device. The receptacle may have a receiving geometry that is keyed to align with and receive a corresponding geometry of the periphery of the head of the implant device, for example to ensure a particular orientation between the engagement structure and the head when the engagement structure and the head are in engagement. The receptacle may have an oval geometry and the head may have a mating oval geometry received within the receptacle in the engagement. The receptacle may be configured to receive the head in the engagement with a relatively close fit, to promote effective alignment and fluid communication with the implant device. When in the engagement, clearance fit of the head in the receptacle may be no larger than 0.5 millimeter, no larger than 0.35 millimeter, no larger than 0.25 millimeter, no larger than 0.2 millimeter, no larger than 0.15 millimeter or no larger than 0.1 millimeter or even smaller. By a clearance fit of a structure received in a receiving structure, it is meant that the received structure (e.g., the head) as properly received (e.g., in a receptacle to engage the engagement structure with the head) may move laterally within receiving structure (e.g., the receptacle) perpendicular to a direction of insertion of the receiving structure into the received structure by no more than that amount. The engagement structure may have a peripheral wall that defines a lateral extent and shape of the receptacle in which the head is received. In some preferred implementation, such a peripheral wall will have a thin wall thickness to facilitate easy insertion of the engagement structure into the palpebral fissure to access and engage with the head of an implant device. The thickness of such a peripheral wall may be not larger than 2 millimeters, not larger than 1.5 millimeters, not larger than 1.25 millimeters, not larger than 1 millimeter, not larger than 0.75 millimeter, not larger than 0.5 millimeter or not larger than 0.25 millimeter. The thickness of such a peripheral wall may be at least 0.05 millimeter at least 0.1 millimeter, at least 0.15 millimeter or at least 0.2 millimeter.

When the engagement structure and the head are in engagement, the paranasal sinus fluid manipulation tool may have an portion that is disposed exterior to the implant device and distal to a proximal end of the implant device, which portion of the fluid manipulation tool may be referred to as an exteriorly overlapping portion. The exteriorly overlapping portion of the fluid manipulation tool may be part of the engagement structure, and may be configured to orient the fluid manipulation tool and the implant device when the engagement structure and the head are in engagement. The exteriorly overlapping portion may be or include a peripheral wall of a receptacle for receiving the head when the head and the engagement structure are in engagement.

The paranasal sinus fluid connection engagement structure may include an insertion stub that inserts through an opening in a head of the implant device into the internal passage of the implant device when the engagement structure and the head are in engagement, for example to assist in aligning the engagement structure and the implant device for effective fluid communication. The insertion stub may be configured to enhance alignment and fluid communication between a fluid manipulation tool and the implant device in the engagement. A clearance fit between the insertion stub in the internal passage in the engagement may be no larger than 0.35 millimeter, no larger than 0.25 millimeter, no larger than 0.2 millimeter, no larger than 0.15 millimeter, or no larger than 0.1 millimeter. The insertion stub may be configured so that when in the engagement the insertion stub does not extend beyond a distal end of the internal passage, for example so as not to have potential to interact with tissue in a paranasal sinus. When in the engagement, such an insertion stub may extend longitudinally into the internal passage of the implant device by no more than 20 millimeters, no more than 15 millimeters, no more than 10 millimeters, no more than 5 millimeters or no more than 3 millimeters. The engagement structure may include both an insertion stub and a receptacle to receive the head of the implant device.

The head of the implant device may be disposed adjacent a proximal end of the implant device, and when the engagement structure and the head are in the engagement a fluid manipulation tool of which the engagement structure is a part may have no portion that extends distal of a distal end of the implant device, which distal end of the implant device is at a longitudinal end opposite the proximal end. Such a fluid manipulation tool may have no portion that extends into the opening through the head into the internal passage when the engagement structure and the head are in engagement, in which case the engagement structure will not include an insertion stub, reducing potential for damage to a wall of a conduit of the implant device through which the internal passage of the implant extends.

The paranasal sinus fluid connection engagement structure may have design features that promote effective conduction of fluid to or from the internal passage of the implant device, for example without excessive leakage or loss of pressurized fluid intended for conduction to the internal passage for delivery to a paranasal sinus or with transmission of sufficient vacuum to the internal passage to suction desired fluid from a paranasal sinus. The engagement structure may be configured so that when the engagement structure is in engagement with the head, the engagement structure and the head may be in surface contact around the entire periphery of opening of the internal passage in the head. The surface contact may include flush surface contact and/or overlapping surface contact. By flush surface contact it is meant contact between opposing surfaces of the engagement structure and the head that face each other and come into contact as the engagement structure is advanced to engage the head when the implant device is in an implanted position. Such flush surface contact may be in a plane perpendicular to the direction of advancement of the engagement structure to engage the head (e.g., contact between a face of the head and an opposing surface of the engagement structure that stops further advancement of the head into a receptacle of the engagement structure). By overlapping surface contact it is meant contact between surfaces that do not face each other until the engagement structure is advanced to an extent that at least a portion of the engagement structure has advanced to be distal of a proximal extent of the head (e.g., contact between peripheral edges of the head and internal wall surfaces of a receptacle of the engagement structure). The contact between the engagement structure and the head may be sufficient to form a fluid seal between the engagement structure and the head for example for sealed fluid communication between a fluid conduit of a fluid manipulation tool and an internal passage of the implant device.

The engagement structure, and particularly surfaces of the engagement structure that are designed to contact the head of the implant device when in engagement, may be made of materials that promote effective fluid communication with the internal passage of the implant device without damage to the structural integrity of the implant device. The material may be deformable to an extent to conform with a mating contact surface of the head to an extent and in a manner to enhance a fluid seal between the engagement structure and the head and/or to reduce possibility that contact between the engagement structure and the head will mechanically damage the implant device. The engagement structure may include a contact surface or surfaces that in the engagement are in contact with the head and such surface or surfaces may be of a material having a durometer of no larger than Shore D 100, no larger than Shore D 70, no larger than Shore D 50, no larger than Shore D 30, no larger than Shore A 100, no larger than Shore A 90 or no larger than Shore A 80. Such a durometer may be not less than Shore A 30, not less than Shore A 50 or not less than Shore A 70. The material may be a polymeric material, such as for example comprising a silicone composition, a polyurethane composition or a polyolefin composition. The material may comprise an elastomeric composition. The material may be of a rubber material (e.g., surgical rubber). All surfaces of the engagement structure that contact the head in the engagement may be of the same material or may include different materials for different contact surfaces. The engagement structure may be formed as a unitary piece made of a single material or may include a contact material supported by a support structure of a different material, for example a more rigid material than material of contact surfaces.

Various feature refinements and additional features are applicable to the fluid container.

The fluid container may be provided by a syringe. For example the fluid container may include at least a portion of a syringe barrel. Such a syringe may include a piston disposed within the barrel that is manipulable to manipulate fluid in the syringe barrel, for example by advancement of the piston within the barrel to apply pressure to fluid in the barrel to force the fluid to flow from the barrel to the internal passage of an implant device or by retraction of the piston to create a vacuum in the barrel to suction fluid from the internal passage of the implant device when the engagement structure and the head are in engagement. The engagement structure may be on a distal portion, may adjacent a distal end, of a fluid manipulation tool, and which may be on a distal portion of a fluid transmission attachment connected with the syringe. A fluid transmission structure of such a fluid transmission attachment may comprise a fluid conduit in fluid communication with the fluid container and an internal passage of the implant device when the engagement structure and a head of the implant device are in engagement. Such a fluid transmission attachment may be connected with a syringe through corresponding connecting structures, for example through a luer connection.

The fluid container may contain a fluid treatment composition disposed within the fluid container. Such a fluid treatment composition may be suitable for being conducted to the internal passage of an implant device through manipulation of a fluid manipulation tool for delivery to a paranasal sinus, for example to treat for sinusitis or some other condition of the paranasal sinus. The treatment composition may be an aqueous irrigation liquid. The treatment composition may be a drug treatment composition. The drug treatment composition may comprise at least one drug for treating sinusitis or other condition of a paranasal sinus. The drug treatment composition may comprise one or more of the following: an antibiotic, a steroid, an anti-viral, an antihistamine, an anti-fungal, a mast cell stabilizer, a mucolytic, a non-steroidal anti-inflammatory drug (NSAID), a vasoconstrictor and an immunosuppressant. Some example antibiotics include: sulfa, or sulfonamide, drugs, such as for example sulfacetamide (e.g., in OCUSOL) and sulfisoxazole (e.g., in GANTRISIN®); macrolide drugs, such as for example azithromycin (e.g., in AZACITE®) and erythromycin (e.g., in ERYPED®); aminoglycoside drugs, such as for example tobramycin (e.g., in TOBREX®) and gentamicin (e.g., in GENOPTIC®); fluoroquinolone drugs, such as for example ciprofloxacin (e.g., in CILOXAN®), besifloxacin (e.g., in BESIVANCE®) and moxifloxacin (e.g., in VIGAMOX®); tetracycline drugs, such as for example oxytetracycline (e.g., in CODEX); and antibiotic drug combinations, such as for example containing a combination of bacitracin, neomycin and polymyxin B (e.g., in OCUSPORE B) and a combination of gramicidin, neomycin and polymyxin B (e.g., in NEOCIN PG). Some example antivirals include gancyclovir (e.g., in ZIRGAN®) and trifluridine (e.g., in VIROPTIC®). Some example steroids include loteprednol (e.g., in LOTEMAX®) and prednisolone (e.g., in PRED FORTE®). Some example anthistimines include ketotifen (e.g., in ALAWAY®), otopatadine (e.g., in PATADAY®) and pinastine (e.g., in ELESTAT®). Some example mast cell stabilizers include nedocromil sodium (e.g., in ALOCRIL®) and lodoxamide (e.g., in ALOMIDE®). Some example anti-fungals include natamycin (e.g., in NATACYN®) and euconzol. Some example mucolytics include N-acetylcysteine (e.g., in PARVOLEX). Some example NSAID materials include nepafenac (e.g., in NEVANAC®) and bromfenac (e.g., in BROMDAY®). Some example vasoconstrictors include naphazoline (e.g., in NAPHCON A®) and tetrahydrozoline (e.g., in VISENE®). Some example immunosuppressants include cyclosporine (e.g., in RESTASIS®). All of the aforementioned materials include any pharmaceutically acceptable salts thereof. The fluid container may contain any desired volume of the treatment composition. Such a volume may be in a range having a lower limit of 0.1, 0.25, 0.5, 0.74 or 1 milliliter and an upper limit of 5, 3, or 2 milliliters. Such a range may be the total treatment composition contained within the fluid container or may be the volume of treatment composition contained within the fluid container that is deliverable from the fluid container, which may be referred to as the deliverable volume. The deliverable volume refers to that volume of fluid in the fluid container that can be effectively delivered from a fluid manipulation tool or other fluid dispensing tool from which the treatment composition is delivered. The delivery volume may be less than the total volume of treatment composition contained in the fluid container because of residual treatment composition that may be retained in the fluid manipulation tool or other fluid dispenser tool used to deliver the treatment composition, for example residual treatment composition that may be retained on internal wall surfaces of such tools (e.g., internal wall surfaces of the fluid container, for example internal wall surfaces of a syringe barrel) or that remain in fluid conduction portions of such a tool between the fluid container and a distal fluid emission tip of the tool (e.g., within a fluid manipulation tool between the fluid container and a fluid emission opening adjacent the engagement structure on a distal portion of the fluid manipulation tool). A kit may include multiple different treatment compositions, and may include multiple fluid containers (e.g., multiple syringes) each containing a different treatment composition.

Various feature refinements and additional features are applicable to the paranasal sinus access implant device.

The implant device may include:
  a proximal end at a first longitudinal end, the head being adjacent the proximal end;
  a distal end at a second longitudinal end that is longitudinally opposite the first longitudinal end;
  a conduit disposed between the head and the distal end, the internal passage extending through the head and the conduit;
  a length longitudinally along the implant device between the proximal end and the distal end in a range of from 2 millimeters to 50 millimeters; and
  a width of the internal passage transverse to the length of the paranasal sinus access implant device in a range of from 0.25 millimeter to 5 millimeters; and
  the implant device may be configured to be implanted between the lacrimal apparatus in the orbit and a paranasal sinus, wherein when so implanted the proximal end is disposed in the lacrimal apparatus within the orbit and the distal end is disposed in the paranasal sinus.

Such a conduit may include one or more feature refinements or additional features to further enhance operability in combination with a fluid manipulation tool to manipulate fluid through the internal passage when the implant device is implanted. The conduit may have a thicker wall toward the proximal end adjacent the head that provides better mechanical properties to facilitate implantation and to also provide enhanced mechanical resistance to possible damage from mechanical interactions with the fluid manipulation tool. The conduit may include a first longitudinal portion and a second longitudinal portion located toward the distal end relative to the first longitudinal portion, with the first longitudinal portion of the conduit having a first minimum wall thickness adjacent the internal passage and the second longitudinal portion of the conduit having a second minimum wall thickness adjacent the internal passage that is smaller than the first minimum wall thickness, wherein the implant device may be configured to be implanted with at least a portion of each of the first longitudinal portion and the second longitudinal portion of the conduit disposed across tissue between the lacrimal apparatus in the orbit and the paranasal sinus and at least a portion of the second longitudinal portion of the conduit disposed in the paranasal sinus. The first longitudinal portion of the conduit may or may not have a uniform wall thickness and may or may not have a smooth exterior surface.

It has been found that implant devices may be better retained following implantation if the implant devices include anchoring surface features including protrusion areas and recess areas along a conduit that is to be inserted into the fistula for implantation. Anchoring is enhanced when a maximum outside diameter defined by protrusion areas to be disposed in the fistula is larger than the diameter of the fistula that was formed to accept the conduit of the implant device. This creates a snug fit of the conduit in the fistula, with tissue forcing itself into the recess areas of the anchoring surface feature. However, such implantation conduits made of relatively flexible plastic materials may bunch up, such as in the manner of an accordion, making it difficult to insert the conduit into the fistula for implantation. It has been found that by including a thicker conduit wall in a proximal portion of the conduit of an implant device than is included in a distal portion that is inserted first into the fistula, that the ease of insertion of the conduit may be significantly improved. In addition, a thicker conduit wall in a proximal portion of the conduit provides added mechanical durability of the conduit adjacent the head of the implant device, providing better mechanical support to the head of the implant device and reducing potential for mechanical damage to proximal portions of the conduit due to mechanical interactions between the implant device and a fluid manipulation tool or other mechanical devices, for example during a fluid manipulation procedure. Such enhanced proximal-end durability may extend the useful life of the implant device in terms of the number of fluid manipulation procedures that may be performed through the implant device using a fluid manipulation tool.

Providing the first longitudinal portion with a smooth exterior surface may beneficially permit some amount of compression and deformation of conjunctival tissue in the orbit in the vicinity of the head of the implant device and around a proximal portion of the conduit when an engagement structure (e.g., a receptacle) of a fluid manipulation tool is advanced to engage the head for a fluid manipulation procedure. A smooth conduit exterior, free of anchoring surface features, permits such compressed tissue to move, or slide, relative to the exterior surface of the first longitudinal portion of the conduit without disrupting mechanical retention of the implant device by tissue that may be engaged by exterior anchoring surface features of the second longitudinal portion of the conduit that may be configured to anchor the implant device.

The first longitudinal portion of the conduit may have a length of at least 3 millimeters, at least 4 millimeters, at least 5 millimeters, at least 8 millimeters or at least 10 millimeters. The first longitudinal portion of the conduit may often have a length that is no greater than 20 millimeters, no greater than 15 millimeters, no greater than 12 millimeters or no greater than 10 millimeters.

The first minimum wall thickness may be at least 0.25 millimeter, at least 0.3 millimeter, at least 0.35 millimeter or at least 0.4 millimeter. The first minimum wall thickness may often be no greater than 0.75 millimeter, no greater than 0.6 millimeter, no greater than 0.55 millimeter, no greater than 0.5 millimeter or no greater than 0.45 millimeter. The wall thickness of the first longitudinal portion of the conduit may be substantially the same and equal to the first minimum wall thickness over some portion of or the entire length of the first longitudinal portion.

The second longitudinal portion of the conduit may have a length of at least 3 millimeters, at least 4 millimeters, at least 5 millimeters, at least 8 millimeters or at least 10 millimeters. The second longitudinal portion of the conduit may often have a length that is no greater than 30 millimeters, no greater than 25 millimeters, no greater than 20 millimeters, no greater than 15 millimeters, no greater than 12 millimeters or no greater than 10 millimeters.

The second minimum wall thickness may be no greater than 0.6 millimeter, no greater than 0.5 millimeter, no greater than 0.45 millimeter, no greater than 0.4 millimeter, no greater than 0.35 millimeter, no greater than 0.3 millimeter, no greater than 0.25 millimeter or no greater than 0.2 millimeter. The second minimum wall thickness may often be at least 0.1 millimeter, at least 0.15 millimeter or at least 0.2 millimeter. The wall thickness of the second longitudinal portion of the conduit may be substantially the same over some portion or portions of the second longitudinal portion of the conduit. The second longitudinal portion of the conduit may have an exterior including an anchoring surface feature including protrusion areas and recess areas. The wall thickness at locations corresponding with the recess areas may be smaller than the wall thickness at locations corresponding with the protrusion areas. The second minimum wall thickness may occur at one or more locations corresponding with one or more of such recess areas.

The first minimum wall thickness may be at least 0.05 millimeter larger, at least 0.1 millimeter larger, at least 0.15 millimeter or at least 0.175 millimeter larger than the second minimum wall thickness. The first minimum wall thickness may be no more than 0.3 millimeter larger, no more than 0.25 millimeter larger or no more than 0.2 millimeter larger than the second minimum wall thickness.

The first longitudinal portion of the conduit may have a maximum exterior width (first maximum exterior width) that is smaller than a maximum exterior width of the second longitudinal portion of the conduit (second maximum exterior width). The second maximum exterior width may be at least 0.1 millimeter larger, at least 0.2 millimeter larger, at least 0.25 millimeter larger, at least 0.3 millimeter larger, at least 0.35 millimeter larger, at least 0.4 millimeter larger or at least 0.5 millimeter larger than the first maximum exterior width. The second maximum exterior width may often be no more than 1 millimeter, no more than 0.75 millimeter, no more than 0.5 millimeter or no more than 0.4 millimeter larger than the first maximum exterior width. The first maximum exterior width may be at least 1.25 millimeters, at least 1.5 millimeters, at least 1.75 millimeters or at least 2 millimeters. The first maximum exterior width may often be no greater than 3 millimeters, no greater than 2.5 millimeters, no greater than 2.25 millimeters or no greater than 2 millimeters. The second maximum exterior width may be at least 1.5 millimeters, at least 1.6 millimeters at least 1.75 millimeters, at least 2 millimeters, at least 2.25 millimeters or at least 2.5 millimeters. The second maximum exterior width may be no greater than 5 millimeters, no greater than 4 millimeters, no greater than 3 millimeters, no greater than 2.75 millimeters, no greater than 2.5 millimeters or no greater than 2.25 millimeters.

The first longitudinal portion of the conduit may have a minimum exterior width (first minimum exterior width) and the second longitudinal portion of the conduit may have a minimum exterior width (second minimum exterior width) that is smaller than the first maximum exterior width. The first minimum exterior width may be at least 0.1 millimeter larger, at least 0.2 millimeter larger, at least 0.25 millimeter larger, at least 0.3 millimeter larger, at least 0.35 millimeter larger, at least 0.4 millimeter larger or at least 0.5 millimeter larger than the second minimum exterior width. The first minimum exterior width may be no greater than 3 millimeters, no greater than 2.5 millimeters, no greater than 2.25 millimeters or no greater than 2 millimeters. The first minimum exterior width may be at least 1 millimeter, at least 1.25 millimeters, at least 1.5 millimeters, at least 1.75 millimeters or at least 2 millimeters. The first longitudinal portion of the conduit may have a substantially constant cross-section (e.g., constant circular cross-section), in which case the maximum and minimum exterior widths of the first longitudinal portion of the conduit are the same. The second minimum exterior width may be no greater than 2.5 millimeters, no greater than 2 millimeters, no greater than 1.75 millimeters or no greater than 1.5 millimeters. The second minimum exterior width may often be at least 1 millimeter, at least 1.25 millimeter, at least 1.50 millimeters or at least 1.75 millimeters. The second longitudinal portion may have a surface geometry wherein the second minimum exterior width may be smaller than a second maximum exterior width of the second longitudinal portion. The second minimum exterior width may correspond with locations of the second minimum wall thickness.

The conduit may have a circular cross-section at some or all points along the length of the first and second longitudinal portions of the conduit. The first minimum wall thickness and the second minimum wall thickness may be tubular walls.

The conduit may be configured so that an exterior of the conduit comprises an anchoring surface feature which assists to anchor the implant device when the device is implanted. The anchoring surface feature includes protrusion areas and recess areas. The second minimum wall thickness may occur at a location corresponding with at least one of the recess areas. The implant device may be configured so that when implanted the conduit is disposed through the fistula with at least a portion of the recess areas disposed within the fistula and with at least a portion of the protrusion areas disposed in the fistula and engaging tissue exposed within the fistula to anchor the implant device. The structural and mechanical characteristics of protrusion occurrences in the protrusion areas may affect anchoring performance of the protrusion areas. The height of the protrusion areas relative to the recess areas may affect anchoring effectiveness when the implant device is implanted. A larger height may provide greater anchor effectiveness, but also may involve a larger overall width of the implant device that must be inserted into the fistula. The protrusion areas may have a height relative to the recess areas of at least 0.1 millimeter, at least 0.2 millimeter, at least 0.25 millimeter or at least 0.3 millimeter. The protrusions areas may have a height relative to the recess areas of no greater than 2 millimeters, no greater than 1.5 millimeter, no greater than 1 millimeter, no greater than 0.75 millimeter, no greater than 0.5 millimeter or no greater than 0.4 millimeter. The height may be of particular protrusion occurrences relative to adjacent areas of recesses. Protrusion occurrences are also referred to herein as anchor protrusions. Such anchor protrusions may be configured to flexibly deform when the conduit is inserted through the fistula for implantation, for example to flexibly deform in a direction opposite the direction of insertion when the anchor protrusions contact tissue disposed in the fistula during insertion. After insertion, the anchor protrusions may over time return to their original shape and extend deeper into adjacent tissue to better anchor the implant device. The mechanical properties of the anchor protrusions may be influenced by materials of construction. Preferred materials of construction for the protrusion areas, and also for the other portions of the implant device, are polymeric materials. The polymeric materials may preferably be medical grade materials. Some preferred polymeric materials are silicones and polyurethanes. For enhanced performance, the material of construction should have a rigidity that interacts positively with tissue in the vicinity of the fistula, for example to promote load sharing and good anchoring. One preferred material of construction is a polymeric material (e.g. silicone or polyurethane) having a durometer (Shore A) in a range having a lower limit of 50, 60, 70 or 80 and an upper limit of 100, 80, 70 or 60, provided that the upper limit must be larger than the lower limit. One preferred range is for a durometer (Shore A) of 60-100, with a range of 80-100 being even more preferred. For some implementations the polymeric material has a durometer (Shore A) of about 60, of about 80 or of about 100. Mechanical properties of the protrusion occurrences of the protrusion areas will also be affected by the geometry of the protrusion occurrences. The protrusion occurrences may have a width that tapers, or narrows, in a direction from a base toward a top of the protrusion occurrences, with the base being a portion of a protrusion occurrence disposed toward the internal passage of the conduit and a top of the protrusion occurrence being the extremity of the protrusion occurrence away from the internal passage of the conduit. The width may be transverse to the length of the conduit. The protrusion occurrences may have a width at the base that is no larger than 2 millimeters, no larger than 1.5 millimeters, no larger than 1.25 millimeters or no larger than 1 millimeter. One or more of the protrusion occurrences may have a width at the base that is at least 0.2 millimeter, at least 0.3 millimeter, at least 0.5 millimeter, at least 0.75 millimeter or at least 1 millimeter. The protrusion occurrences may have a width adjacent the top that is no larger than 0.75 times width at the base, no larger than 0.5 times the width at the base, or no larger than 0.25 times the width at the base. The protrusion occurrences may have a width midway between the base and the top that is no larger than 0.8 times the width of the base, no larger than 0.7 times the width of the base, no larger than 0.6 times the width of the base or no larger than 0.5 times the width at the base.

The protrusion areas may be provided by a single protrusion occurrence feature located to correspond with the interior of the fistula when the implant device is implanted. In more preferred implementations, the protrusion areas include multiple protrusion occurrences spaced on the exterior of the conduit. The protrusion occurrences may have a center-to-center spacing, in one or more directions, of at least 0.5 millimeter, at least 0.75 millimeter, at least 1 millimeter or at least 1.75 millimeters. The protrusion occurrences may have a center-to-center spacing of no greater than 2.5 millimeters, no greater than 2 millimeters or no greater than 1.75 millimeters. The protrusion occurrences may have a center-to-center spacing longitudinally along the conduit. The protrusion occurrences may have a center-to-center spacing that is at least 0.5 times the base width of the protrusion occurrences, or at least 1 times the base width of the protrusion occurrences or at least 2 times the base width of the protrusion occurrences. The protrusion occurrences may have a center-to-center spacing that is no more than 5 times a base width of the protrusion occurrences, no more than 3 times a base width of the protrusion occurrences or no more than 2 times a base width of the protrusion occurrences.

The protrusion areas may be located on a longitudinal portion of the conduit that includes at least a portion of the conduit that will be disposed within a fistula when the implant device is implanted. The protrusion areas may be on a longitudinal portion of the conduit that extends for at least 2 millimeters along the length of the implant device, that extends for at least 3 millimeters along the length of the implant device, that extends for at least 4 millimeters along the length of the implant device, that extends for at least 5 millimeters along the length of the implant device or that extends for at least 8 millimeters along the length of the implant device. A longitudinal portion of the conduit including the protrusion areas may be no longer than 20 millimeters, no longer than 15 millimeters or no longer than 10 millimeters. A longitudinal portion of the conduit including the protrusion areas may be disposed at least 2 millimeters from the proximal end of the device, at least 3 millimeters from the proximal end of the device, or at least 4 millimeters from the proximal end of the device. A longitudinal portion of the conduit including the protrusions may be disposed at least 1 millimeter, at least 2 millimeters or at least 3 millimeters from a head of the implant device. Providing significant distance between the head and commencement of the protrusion areas permits the head to better "float" on the surface of tissue, which may enhance patient comfort and device performance. The protrusion areas may be disposed along a longitudinal portion of the conduit with the protrusion areas covering no more than 35% of the area along that longitudinal portion of the conduit, no more than 25% of the area along that longitudinal portion of the conduit or not more than 20% of the area along that longitudinal portion of the conduit. Providing significant spacing between protrusion occurrences may permit better engagement of tissue by the anchoring surface feature.

The protrusion areas may comprise at least one circumferential ridge. By circumferential ridge is meant a ridge that extends around an entire circumference of the conduit. The protrusion area may comprise at least two, at least three or at least five circumferential ridges. The protrusion areas may comprise a spiral ridge. Such a spiral ridge may extend along a longitudinal portion of the conduit. The protrusion areas may comprise a knob or may comprise multiple knobs. The anchoring surface feature may comprise a textured surface, with the protrusion areas comprising protruding portions of the textured surface and the recess areas comprising recess portions of the textured surface.

The length of the implant device may be selected to provide sufficient conduit length for extending through the entire length of the fistula plus any extension distance desired in the lacrimal apparatus proximal to the fistula and in the paranasal sinus distal to the fistula. The length of the implant device and/or of the conduit may be in a range having a lower limit of 2 millimeters, 3 millimeters, 4 millimeters, 5 millimeters, 8 millimeters, 10 millimeters or 12 millimeters and an upper limit of 50 millimeters, 40 millimeters, 30 millimeters, 25 millimeters, 20 millimeters, 15 millimeters or 10 millimeters, provided that the upper limit is larger than the lower limit. One preferred range for some implementations when the fistula is between the orbit and the ethmoid sinus or the maxillary sinus is for the length of the implant device and/or for the length of the conduit to be in a range of from 10 millimeters to 30 millimeters, with a range of from 15 millimeters to 25 millimeters being more preferred. By length of the implant device or the conduit it is meant the dimension longitudinally along the implant device or the conduit, as the case may be, from the proximal end to the distal end of the implant device or conduit, and may be along a longitudinal axis through the internal passage. The length may be a straight line, for example when the internal passage is straight, or the length may be curvilinear or some other shape, for example when the internal passage is not linear. When a reference is made herein to transverse to the length, the reference is to a right angle to the longitudinal direction of the length at that point (e.g., right angle to a line of the length or to a line tangent to a curve of the length).

The implant device may advantageously be designed with a conduit of appropriate width dimensions to fit snuggly within a desired size of fistula. The implant device may have a first exterior width dimension defined by a maximum extent of the protrusion areas transverse to the length of the device, with the first exterior width being within a range having a lower limit of 0.75 millimeter, 1 millimeter, 1.25 millimeters, 1.5 millimeters, 1.75 millimeters or 2 millimeters and an upper limit of 8 millimeters, 7 millimeters, 6 millimeters, 5 millimeters, 4 millimeters, 3 millimeters, 2 millimeters or 1.75 millimeters, provided of course that the upper limit must be larger than the lower limit. The conduit may have a second width dimension defined by the minimum extent of the recess areas transverse to the length of the device, and which second exterior width dimension will be smaller than the first exterior width dimension defined by the protrusion areas. The second exterior width dimension defined by the recess areas may be smaller than the first exterior width dimension defined by the protrusion areas by an amount within a range having a lower limit of 0.2 millimeter, 0.25 millimeter, 0.35 millimeter or 0.5 millimeter and having an upper limit of 1.5 millimeters, 1 millimeter or 0.75 millimeter. The height of the protrusion areas may be one-half the difference between the first exterior width and the second exterior width. Either one of or each one of the first exterior width and the second exterior width may be the diameter of a circle.

The implant device may include a head adjacent to the conduit at the proximal end of the implant device. The implant device may be configured so that when the implant device is implanted, the head is disposed in the lacrimal apparatus, and preferably with the head located in the orbit. The head may beneficially keep the implant device from migrating through the fistula toward the paranasal sinus following implantation of the implant device. The head may comprise a flanged tissue engagement surface on a side of the head disposed toward the conduit and configured to engage tissue outside of and adjacent to the fistula when the implant device is implanted. The flanged tissue engagement surface may be a flat surface. The flanged tissue engagement surface may have non-flat surface features configured to improve seating of the surface against tissue, such as for example to inhibit rotation of the implant device within the fistula after implantation. The head may have a face surface opposite the flanged tissue engagement surface and also disposed away from the conduit and disposed away from tissue engaged by the flanged tissue engagement surface when the implant device is implanted. The face surface may be substantially flat. The face surface may be disposed at the proximal end of the implant device and the internal passage may open at the face surface. The separation distance between the face surface and the flanged tissue engagement surface may be in a range having a lower limit of 0.25 millimeter, 0.5 millimeter or 0.75 millimeter and having an upper limit of 2 millimeters, 1.5 millimeters or 1 millimeter. Such separation distance need not be constant across the flanged tissue engagement surface and face surface. A maximum separation distance between the face surface and the flanged tissue engagement surface may be referred to as the depth of the head, and such depth may be in a range described above for the separation distance between the face surface and the flanged tissue engagement surface. The flanged tissue engagement surface need not be continuous and may be divided into multiple distinct surface portions. For example, the flanged tissue engagement surface may include a first flanged portion disposed to one side of the internal passage and a second flanged surface portion disposed to a second side of the internal passage that is opposite the first side. Each of the face surface and the flanged tissue engagement surface may have a length dimension that represents a maximum separation distance between points on an outer edge of the respective surface, and may each have a width dimension that is a maximum separation distance between points on the outer edge transverse to the length dimension. The length dimensions of the face surface and the flanged tissue engagement surface may be the same or may be different. The width dimensions of the face surface and the flanged tissue engagement surface may be the same or may be different. The face surface and the flanged tissue engagement surface may have corresponding outer edges. The length dimension of any or all of the face surface, the flanged tissue engagement surface and the head may be larger than a first exterior width of the conduit defined by an extent of the protrusion areas transverse to the length of the implant device, when the implant device includes an anchoring surface feature such as summarized above. The length dimension of any or all of the face surface, the tissue engagement surface and the head may be in a range having a lower limit of 1 millimeter, 2 millimeters, 3 millimeters, 4 millimeters or 5 millimeters and an upper limit of, 10 millimeters, 8 millimeters or 7 millimeters. The width dimension of any or all of the face surface, tissue engagement surface and the head may be in a range having a lower limit of 0.5 millimeter, 1 millimeter, 1.5 millimeters or 2 millimeters and an upper limit of 5 millimeters, 4 millimeters or 3 millimeters. The length dimension of any or all of the face surface, the flanged tissue engagement surface and the head may be at least 1 millimeter, at least 2 millimeters, at least 3 millimeters or at least 4 millimeters larger than such first exterior width of the conduit defined by an extent of the protrusion areas, when the implant device includes an anchoring surface feature such as summarized above. A ratio of the length of any of or all the face surface, the flanged tissue engagement surface and the head to such a first exterior width of the conduit may be at least 2. Such a ratio may be smaller than 4. The width of any or all of the face surface, the flanged tissue engagement surface and the head may be not larger than, or may be smaller than (e.g., by at least 0.1 mm or by at least 0.2 mm), such a first exterior width of the conduit defined by an extent of the protrusion areas, when the implant device includes an anchoring surface feature such as summarized above. A ratio of the length dimension to the width dimension for any or all of the face surface, the flanged tissue engagement surface and the head may be in a range having a lower limit of 1, 1.5, 2 or 2.5 and an upper limit of 5, 4, 3 or 2.5, provided of course that the upper limit must be larger than the lower limit. Having a larger length dimension to width dimension on the head is particularly preferred when the head will be located in the orbit between the lacrimal caruncle and the plica semilunaris, because the length dimension may advantageously align in a vertical direction next to the eyeball and will help provide sufficient flanged surface area to effectively anchor the implant device on the proximal end and impede conjunctival tissue from covering the opening into the internal passage of the implant device, compensating for the narrower width. This is particularly advantageous when using polymeric materials of construction as described above.

The internal passage through the implant device may have a substantially uniform shape along the entire length of the implant device, or may have a varying shape. The internal passage may be substantially straight from the proximal end of the device to the distal end of the device. The internal passage may have a cross-section available for flow (transverse to the length of the device) that is substantially uniform from the proximal end to the distal end of the implant device. The internal passage may have a substantially circular cross-section. The internal passage may have a substantially elliptical cross-section. The width of the internal passage (maximum dimension across the cross-section of the internal passage available for flow) may be in a range having a lower limit of 0.25 millimeter, 0.5 millimeter or 0.75 millimeter and 1 millimeter and an upper limit of 5 millimeters, or 4 millimeters or 3 millimeters, 2 millimeters or 1.5 millimeters.

The lacrimal apparatus and a paranasal sinus may be in fluid communication through the internal passage of the implant device when the implant device is implanted. The conduit may extend from adjacent the proximal end of the implant device. The conduit may extend to adjacent the distal end of the implant device. The internal passage may have a first end open at the proximal end and a second end open at the distal end, and when the implant device is implanted the first end of the internal passage may open in the lacrimal apparatus and the second end of the internal passage may open in the paranasal sinus.

The implant device may be configured for implantation with the conduit passing through a fistula between a location in a lacrimal apparatus within the orbit and a paranasal sinus selected from the group consisting of a frontal sinus, an ethmoid sinus, a maxillary sinus and a sphenoid sinus, with a frontal sinus, a maxillary sinus or an ethmoid sinus being preferred, with an ethmoid sinus or a maxillary sinus being more preferred, and with an ethmoid sinus being particularly preferred.

Various feature refinements and additional features are applicable to kits.

A kit may include components in addition to an implant device and a fluid manipulation tool, or components assemblable into such a fluid manipulation tool. A kit may include any, or any combination of any, apparatuses, tools, devices, products, components or treatment compositions described herein.

A kit may include at least one cutting tool for cutting away tissue to form a fistula through which the implant device may be implanted during an implant procedure. Such a cutting tool may include a hollow member having a hollow cutting tip at a distal end of the cutting member configured to cut tissue to size the fistula for implantation of the implant device through the fistula. Such a cutting member may have a cutting width that is smaller than a maximum exterior width of a conduit of the implant device configured to be disposed through the fistula during implantation. Such a cutting tool may be a drill.

Forming a fistula for implantation of an implant device to provide a fluid passage between the lacrimal apparatus and a paranasal sinus involves making a hole through a wall of the bone in which the cavity of the paranasal sinus is located. As described herein, such a hole may be made by a sytlet or other solid piercing instrument and then widened as needed to form the fistula to the desired size for implantation of the implant device. For example following the initial piercing to make an initial hole, the hole may be dilated using dilators to make the hole progressively larger until the desired size is obtained. However, it has been found that when forming a fistula for implantation in such a manner, the bone tends to crack and shatter in the vicinity of hole. Although this does not present a medical problem, it has been found that if the bone is kept more in-tact in the vicinity of the hole, then the bone may provide mechanical support to help secure the implant device in place and prevent the implant device from migrating out of the fistula following implantation. Bone integrity in the vicinity of the fistula may be improved by cutting the hole for the fistula rather than piercing and dilating the hole. By cutting through the bone, rather than pushing through the bone, the bone remains more in-tact in the vicinity of the hole and provides better mechanical support to help retain the implant device in place in the fistula following implantation.

A kit may include a cutting tool that may be guidable by a guide member disposable through an internal passage of the cutting tool. The cutting tool may include a hollow cutting member that has a hollow cutting tip at a distal end of the cutting member configured to cut tissue to size the fistula for implantation of the implant device through the fistula. The hollow cutting tip of the cutting tool may be configured to make a larger diameter cut to enlarge a smaller-diameter preliminary cut that may have been previously made to accommodate the guide member, or the cutting tool may be configured to make a desired final cut without prior formation of a smaller initial fistula. The cutting member may be configured to be slidably engaged with the guide member with the guide member disposed through a passage in the cutting member with the distal end of the guide member disposed distal of the distal end of the cutting member. A distal end of the guide member may be configured to be disposed in or distal of the fistula such that the cutting member is slidable over the guide member, for example to conduct the cutting tip of the cutting member to cut tissue to size the fistula for implantation of the implant device when a smaller initial fistula has already been formed or to permit retraction of the cutting member while leaving the guide member in place for use to conduct another tool or tools to the location of the fistula, for example an implantation tool for inserting an implant device into the fistula in position for implantation.

A cutting member of a cutting tool may be or include a hollow needle or a cutting cannula. The cutting member may have a cutting width, or diameter in the case of a circular cut, that is smaller than a maximum exterior width of the conduit of the implant device. The maximum exterior width of the conduit of the implant device may occur at one or more protrusion areas that form part of an anchoring surface feature on the conduit. The cutting width may be at least 0.1 millimeter smaller, at least 0.2 millimeter smaller, at least 0.25 millimeter smaller, at least 0.3 millimeter smaller, at least 0.35 millimeter smaller or at least 0.4 millimeter smaller than the maximum exterior width of the conduit of the implant device. The cutting width may be not more than 1 millimeter, 0.75 millimeter, 0.6 millimeter, or 0.5 millimeter smaller than the maximum exterior width of the conduit. The cutting width may be not larger than 5 millimeters, 4 millimeters, 3.5 millimeters, 3 millimeters, 2.5 millimeters, 2.25 millimeters, 2 millimeters, 1.9 millimeters or 1.8 millimeters. The cutting width may be at least 1 millimeter, 1.5 millimeter, 1.75 millimeter or 1.85 millimeter.

A kit may include an implantation guide tool with a proximal end and a distal end and including a guide member extending longitudinally in a direction from the proximal end toward the distal end of the implantation guide tool. The guide member and internal passage may be configured for mounting the implant device on the guide member with the guide member disposed through the internal passage of the implant device with a distal end of the guide member disposed distal of the distal end of the implant device, and the distal end of the guide member may be configured to be disposed in or distal of the fistula such that the implant device mounted on the guide member is slidable on the guide member toward the distal end of the guide member to conduct the implant device into the fistula for implantation. The guide member may be configured for insertion through a passage through a tool (e.g., cutting tool or carrier tool) to guide the tool to the site of a fistula.

In one example of a guide member, the guide member may be a guide wire or a small diameter needle (e.g., 20 gauge spinal needle), a cutting member may be a larger gage needle through which the guide member may be inserted (e.g., 12 to 14 gauge spinal needle), and an implant device may have an internal passage through which the guide member may be inserted (e.g., 1 mm).

The guide member may be any appropriately sized member on which the implant device or a tool to be guided by the guide member may be slidably conducted along the guide member for implantation. The guide member may be a rigid, flexible or malleable material. The guide member may be a solid member, for example a solid guide wire or a stylet. The guide member may be a hollow member, for example the guide member may be or include a needle or cannula. The guide member may include a cutting end at the distal end configured to cut tissue to form at least a portion of the fistula. Such a hollow guide member with a cutting end may be a needle or cutting cannula. Such a hollow guide member with a cutting end may be useful to cut an initial hole that may then be made larger to a desired size for implantation of the implant device.

A kit may include a carrier tool, also referred to as an implantation tool, for carrying the implant device during an implantation procedure. Such a carrier tool may include a carrier member with a distal tip, with the carrier member being adapted to be disposed through a fistula between the lacrimal apparatus in the orbit and a paranasal cavity with the distal tip located in the paranasal cavity. The carrier tool may include a hand-manipulable handle connected to the carrier member. An implant device may be mountable on the carrier member for implantation of the implant device, with the mounted implant device disposed between the handle and the distal tip with the carrier member disposed through the internal passage and with a proximal end of the implant device disposed toward the handle and a distal end of the implant device disposed toward the distal tip of the member. When the implant device is mounted for implantation, the carrier member, and the carrier tool, may be disengageable from the implant device for implant placement of the implant device during an implantation procedure to provide fluid access to a paranasal sinus. A clearance fit of the carrier member in the internal passage of the implant device when the implant device is mounted on the carrier member for implantation may be small to ensure a close fit and help prevent lateral deformation of the implant device during implantation. For example such a clearance fit may be no larger than 0.5 millimeter, no larger than 0.4 millimeter, no larger than 0.3 millimeter, no larger than 0.2 millimeter or no larger than 0.1 millimeter. Having a close fit between of the carrier member in the internal passage of the implant device helps prevent accordion-like bunching of the implant device during an implant procedure as the carrier tool with the mounted device may be advanced to advance (push) the carrier member and the mounted implant device into the fistula for implantation.

Any and all parts of a kit may conveniently be contained within a common package, such as a common box, bag or other common packaging enclosure. Some or all components of a kit may be sterilized and sealed within hermetically sealed enclosures, such as for example hermetically sealed bags or wrapping.

Various feature refinements and additional features are applicable to methods.

A method for manipulating fluid in relation to a paranasal sinus may or may not be performed as part of a medical procedure also including implanting an implant device to provide an artificial fluid path in fluid communication with the lacrimal apparatus. Implanting an implant device may include cutting away tissue to form a fistula for implantation of an implant device, which is particularly advantageous when the fistula is to pass through bone, such as in the case of implant devices designed to provide an artificial fluid passage between the lacrimal apparatus and a paranasal sinus. A method may include cutting away tissue to form a fistula of a size to receive at least a portion of a conduit of an implant device, the fistula having a proximal end opening into the lacrimal apparatus, and implanting the implant device with at least a portion of the conduit of the implant device in the fistula. The implanting may include advancing the implant device into an implantation position using a carrier tool. The implanting may include advancing the carrier tool to have the carrier tool push the implant device into an implant position. The implanting may include sliding the implant device along a guide member or along a carrier member of a carrier tool into an implantation position.

The method may be performed using a kit of an aspect of this disclosure or parts of such a kit. Cutting away tissue may comprise cutting the tissue with a cutting tool of such a kit. During the cutting away or some portion thereof, the cutting member may or may not be disposed over and conducted to the location for the cut by the guide member. For example, a preliminary cut may be made for form a preliminary hole of a smaller size, the guide member may be disposed with a distal end in or distal to the preliminary hole, and the cutting member may be slid over the guide member to cut tissue to produce a larger fistula of the desired size for implantation of the implant device. As another example, a single, final cut may be made to make a hole of a final desired size for implantation which may be made without the aid of a guide member and without making a preliminary hole. In that regard, a shoulder on the ethmoid bone facing the orbit has been identified that is a convenient landmark for orienting a cut into the ethmoid sinus. The shoulder has been named the shoulder of Willoughby.

The cutting away tissue may be accomplished by removing tissue by drilling through the tissue with a drill.

These and other aspects of the disclosure, and possible feature refinements and additional features therefore, will be further understood with reference to the drawings, to the description provided below and to the claims.

BRIEF DESCRIPTION OF THE DRAWINGS

The drawings are included to aid in the understanding of various aspects of the disclosure and possible feature refinements and additional features applicable thereto. Features shown in the drawings are presented for purposes of illustration only, and are not necessarily to scale and are not necessarily detailed in every respect.

FIG. 9 is an illustration of various head configurations for an implant device.

FIG. 20 is an illustration of an embodiment of a paranasal sinus fluid manipulation tool.

FIG. 21 is an illustration of a paranasal sinus fluid treatment apparatus including the paranasal sinus fluid manipulation tool embodiment of FIG. 20 engaged with an implant device.

DETAILED DESCRIPTION

Figure 1:
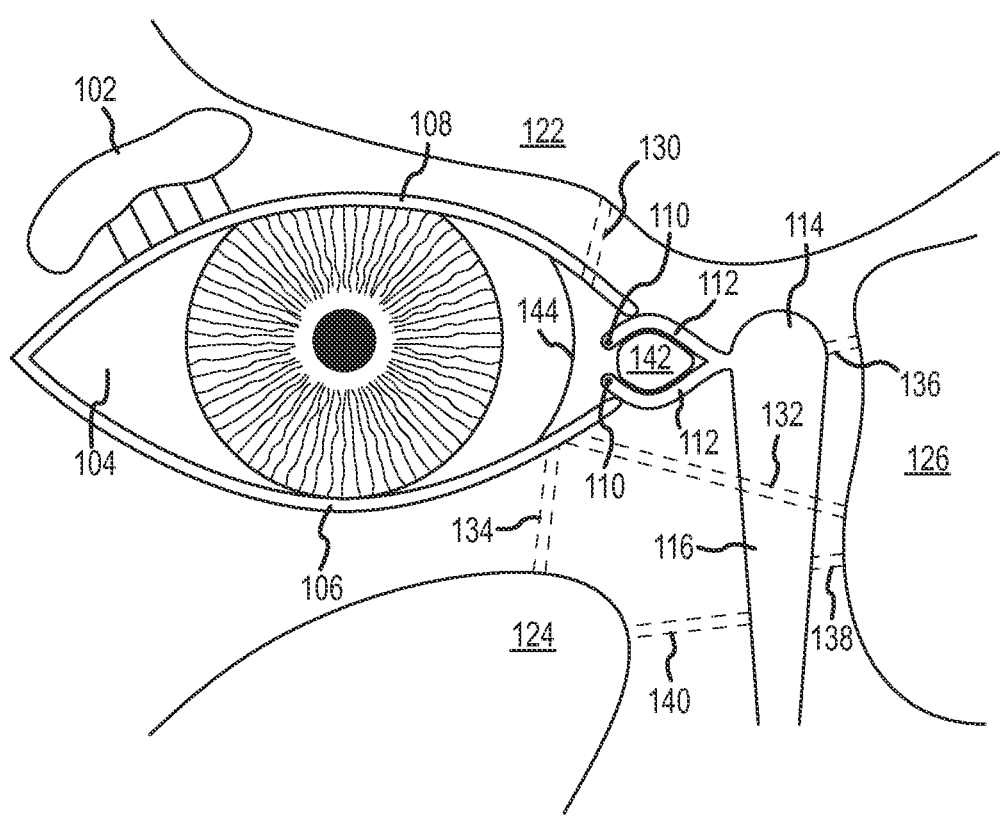
FIG. 1 is an illustration showing some example routes for an implant to provide fluid access from the lacrimal apparatus to a paranasal sinus.
Figure 2:
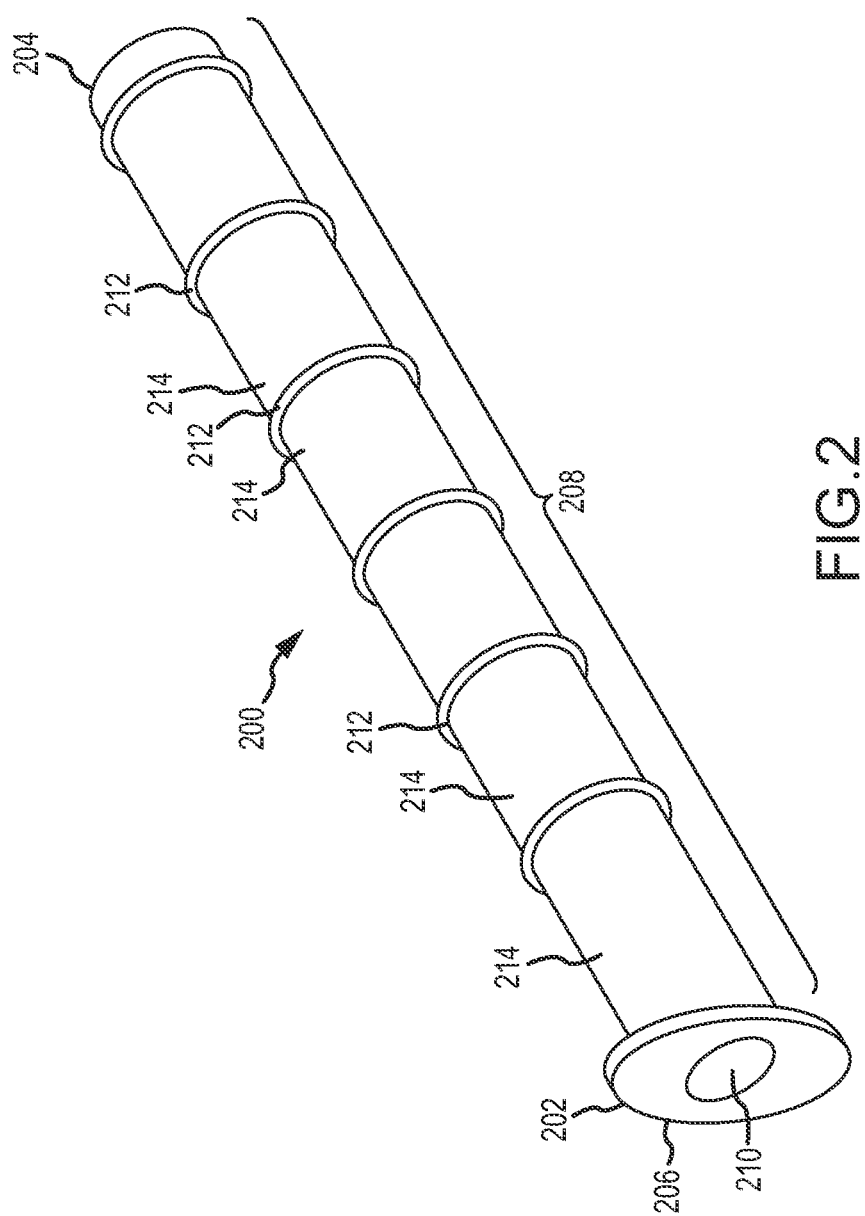
FIG. 2 is perspective view of one embodiment of an implant device.

The terms "lacrimal apparatus" and "lacrimal system" are used interchangeably herein to refer to the collection of physiological components that accomplish the production and secretion of lacrimal fluid to lubricate the eyeball, containment of lacrimal fluid in a reservoir of lacrimal fluid in the orbit and drainage of lacrimal fluid from the orbit to the nasal cavity. The lacrimal apparatus includes the lacrimal glands, the tear drainage system and the reservoir of lacrimal fluid located between the lacrimal glands and the tear drainage system. The reservoir of lacrimal fluid includes the eyelid margins and the conjunctival sac (and including the pool of tears in the lower conjunctival cul-de-sac that is sometimes referred to as the lacrimal lake). The tear drainage system includes the puncta, canaliculi and nasolacrimal duct (including the so-called lacrimal sac located at the top of the nasolacrimal duct) through which excess tears drain to Hasner's valve and into the nasal cavity. FIG. 1 shows generally the lacrimal apparatus. Lacrimal fluid is produced and secreted from lacrimal glands 102 to lubricate the surface of the eyeball 104 disposed within the orbit. Lacrimal fluid forms a coating over the eyeball 104 and is generally contained within the conjunctival sac (the space between the lower eyelid 106, upper eyelid 108 and eyeball 104 that is lined by the conjunctiva). Excess lacrimal fluid is conducted to the vicinity of the medial canthus (medial corner of the eye) and drains through the lacrimal puncta 110 into the lacrimal canaliculi 112 and into the lacrimal sac 114 of the nasolacrimal duct 116. The lacrimal fluid then drains from the nasolacrimal duct 116 through Hasner's valve and into the nasal cavity.

As used herein, a fistula between the lacrimal apparatus and a paranasal sinus refers to an artificially-created passage that fluidly connects the lacrimal apparatus with a paranasal sinus. Such a fistula may be surgically created. The paranasal sinuses include the frontal sinuses, maxillary sinuses, ethmoid sinuses and sphenoid sinuses, which are cavities contained within frontal, maxilla, ethmoid and sphenoid bones, respectively. The paranasal sinuses drain into the nasal cavity. FIG. 1 also shows the general proximity of the frontal sinus 122, maxillary sinus 124 and ethmoid sinus 126 relative to features of the lacrimal apparatus and some example fistula routes shown by dashed lines. A first example fistula route 130 is from the orbit to the frontal sinus. A second example fistula route 132 is from the orbit to the ethmoid sinus 126. A third example fistula route 134 is from the orbit to the maxillary sinus 124. A fourth example fistula route 136 is from the lacrimal sac 114 at the top of the nasolacrimal duct 116 to the ethmoid sinus 126. A fifth example fistula route 138 is from the nasolacrimal duct 116 at a location below the lacrimal sac 114 to the ethmoid sinus 126. A sixth example fistula route 140 is from the nasolacrimal duct 116 at a location below the lacrimal sac 114 to the maxillary sinus 124. The example fistula routes shown in FIG. 1 are for purposes of general illustration only and not to show precise locations where a fistula might be formed to connect a part of the lacrimal apparatus with the corresponding paranasal sinus. Although not shown in FIG. 1, example fistula routes to the sphenoid sinus include from the orbit to the sphenoid sinus and from the nasolacrimal duct 116 to the sphenoid sinus. Forming a fistula to connect to the sphenoid sinuses is generally not as preferred as forming a fistula to connect to the ethmoid sinus, for example because it is generally more convenient and direct to connect with the ethmoid sinus. Also, forming a fistula to either the ethmoid sinus 126 or the maxillary sinus 124 is generally preferred to forming a fistula to the frontal sinus 122, with one reason being that a fistula between the lacrimal system and either the ethmoid sinus 126 or the maxillary sinus 124 may be formed in a way to obtain the benefit of gravity to assist drainage of lacrimal fluid from the lacrimal system into the corresponding paranasal sinus through the fistula. The frontal sinus is located generally above the orbit and will not benefit in the same way from gravity drainage of lacrimal fluid into the paranasal sinus. However, gravity drainage may beneficially assist drainage of fluid from the frontal sinus.

With continued reference to FIG. 1, the first, second and third example fistula routes 130, 132 and 134 are subconjuctival routes that penetrate the conjunctiva to directly connect the lacrimal fluid reservoir within the conjunctival sac to the corresponding paranasal sinus. A fistula along such a subconjunctival route may be surgically formed by a surgical tool piercing through the conjunctiva and the adjacent wall of the bone in which is disposed the corresponding paranasal sinus. For example, for the first example fistula route 130, the fistula would pass subconjunctivally from the orbit and through a wall of the frontal bone into the frontal sinus 122. For example, a fistula following second example fistula route 132 would pass subconjuctivally from the orbit and through a wall of the ethmoid bone into the ethmoid sinus 126. For example, a fistula following the third example fistula route 134 would pass subconjuctivally from the orbit through a wall of the maxilla bone into the maxillary sinus 124. Subconjuctival routes for a fistula such as those of the first, second and third example fistula routes 130, 132 and 134 are generally preferred as being formed at locations that are relatively easy to access. In a preferred implementation of the first, second and third example fistula routes 130, 132 and 134, the proximal end of the fistula opening into the orbit is located between the medial canthus and the medial side of the adjacent eyeball, for example between the lacrimal caruncle 142 and the plica semilunaris 144 as shown in FIG. 1.

Figure 3:
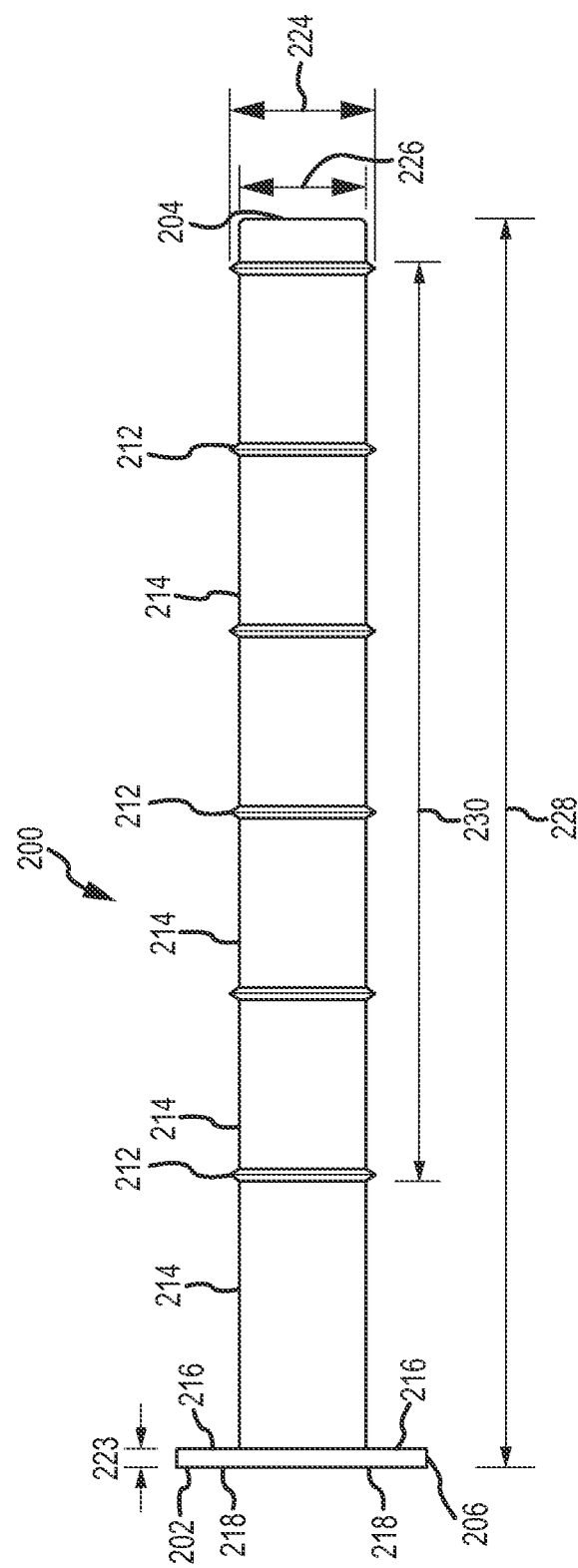
FIG. 3 is a side view of the same embodiment of an implant device as shown in FIG. 2.
Figure 4:
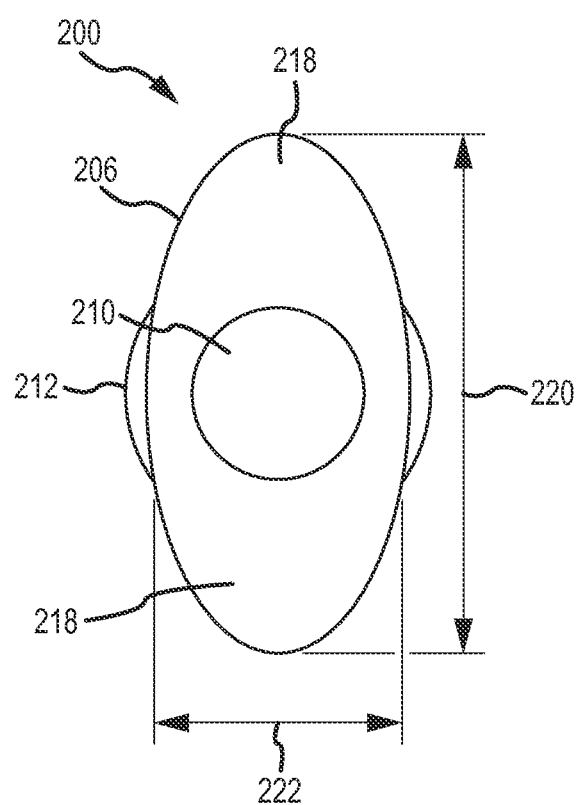
FIG. 4 is an end view of the same embodiment of an implant device as show in FIG. 2.
Figure 5:
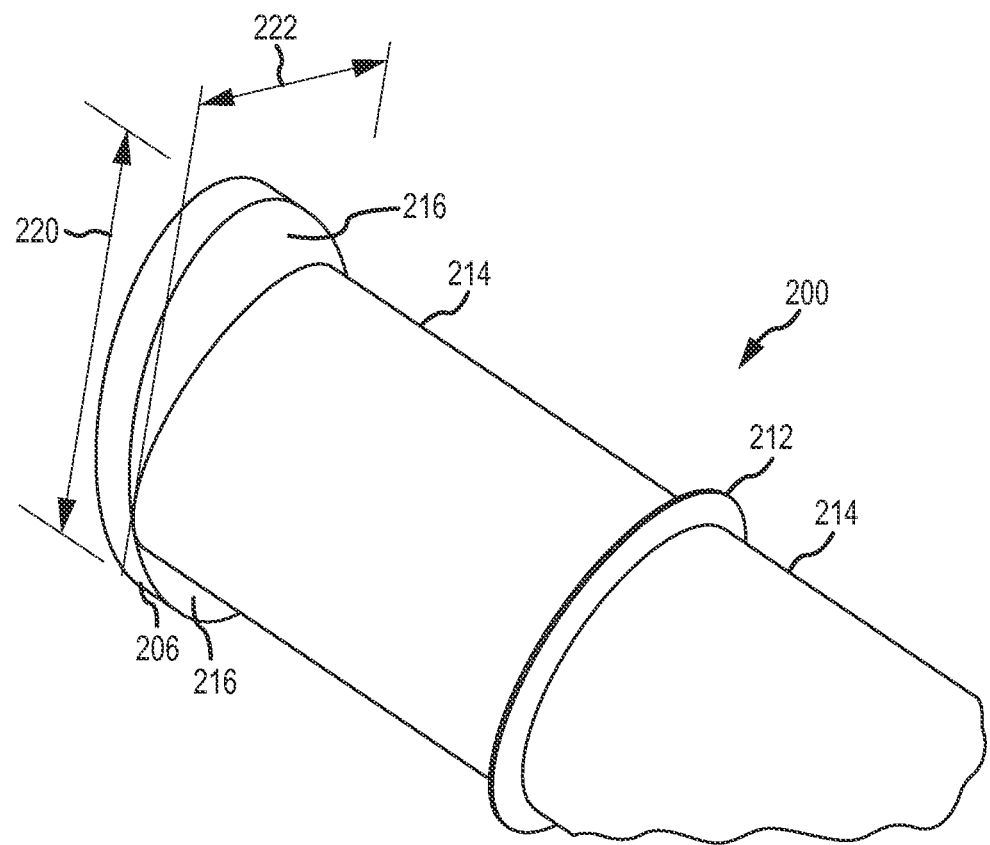
FIG. 5 is a partial perspective view of the same embodiment of an implant device as shown in FIG. 2.

Continuing with reference to FIG. 3, a fistula at the fourth, fifth or sixth example fistula routes 136, 138 and 140 will have a proximal end opening into a location within the nasolacrimal duct 116. Those routes are less preferred than routes 130, 132 and 134, because locations for those routes are significantly less convenient to access both to form the fistula and to perform medical treatments or procedures through the fistula.

FIGS. 2-5 show one embodiment of an implant device, for example that may be implanted through a fistula at the first, second or third routes 130, 132, or 134 shown in FIG. 1. As shown in FIGS. 2-5, an implant device 200 has a proximal end 202 and a distal end 204 located on opposite longitudinal ends of the implant device 200. The implant device 200 includes a head 206 at the proximal end 202 and a conduit 208 extending from the head 206 to the distal end 204. An internal passage 210 extends from the proximal end 202 to the distal end 204, passing through the head 206 and the conduit 208. The internal passage 210 opens at the proximal end 202 and the distal end 204, thereby providing a passage through the entire longitudinal length of the implant device 200. The internal passage 210 of the embodiment shown in FIG. 2 has a cylindrical shape with a uniform circular cross-section (transverse to the length of the implant device 200), and the width of the internal passage is equal to the diameter of the circle of the cross-section and is uniform along the length of the implant device 200. The length of the implant device 200 is the minimum distance longitudinally along the implant device 200 between the proximal end 202 and the distal end 204, and will typically be equal to the distance along an axis of the internal passage 210 from the proximal end 202 to the distal end 204. The implant device 200 includes multiple anchor protrusions 212 on an exterior of the conduit 208. In the embodiment shown in FIGS. 2-5, the anchor protrusions 212 are in the form of spaced circumferential ridges that each extends around the entire circumference of the conduit 208. Adjacent the circumferential ridges of the anchor protrusions 212 are areas of recess 214 on the exterior of the conduit 208.

With continued reference to FIGS. 2-5, when the implant device is implanted to fluidly connect the lacrimal apparatus to a paranasal sinus through a fistula, the head 206 is disposed in the lacrimal apparatus and the proximal end 202 is disposed in the paranasal sinus, and with at least a portion of the conduit 208 disposed through the fistula with at least one, and preferably more than one, of the anchor protrusions 212 engaging tissue within the fistula to anchor the implant device 200. When implanted in this manner, the internal passage 210 opens into the lacrimal apparatus at the proximal end 202 and into the paranasal sinus at the distal end 204. The head 206 has a flanged tissue engagement surface 216 on a side of the head 206 disposed toward the conduit 208, and which flanged tissue engagement surface 216 is advantageously configured to engage tissue adjacent the proximal end of fistula and to prevent the proximal end 202 of the implant device 200 from migrating into the fistula following implantation. On the side of the head 206 opposite the flanged tissue engagement surface 216 is a face surface 218 of the head 206, which face surface 218 is disposed away from tissue engaged by the flanged tissue engagement surface 216 when the implant device is implanted. The head 206 has a first dimension 220 and a second dimension 222 on both the flanged tissue engagement surface 216 and the face surface 218. The first dimension 220 is the length of the respective surface and the second dimension is the width of the respective surface. Such length and width dimensions may also be referred to as major and minor dimensions. The first dimension 220 of a surface 216 or 218 corresponds to the maximum separation distance between points on the outer edge of the surface (maximum cross dimension across the head), and the second dimension 222 of the surface 216 or 218 corresponds to the maximum separation distance between points on the outer edge of the surface that are on a line transverse (perpendicular) to the first dimension. Conveniently, the face surface 218 and the flanged tissue engagement surface 216 may be made with corresponding outer edges, so that the opposing surfaces 216 and 218 have substantially equal length and width dimensions, although such is not required. The first dimension 220 and the second dimension 222 may be referred to generally as the length and width, respectively, of the head 206 when the surfaces 216 and 218 have corresponding shapes, as is the case for the embodiment shown in FIGS. 2-5. When the surfaces 216 and 218 do not have corresponding shapes, the length and width dimensions of the head will be different from one or more of the length and width dimensions of the surfaces 216 and 218. The head 206 has a depth dimension 223 between surfaces 216 and 218. The depth dimension 223 should preferably be kept to a small value so that the head 206 will have a low profile adjacent the proximal end of the fistula when the implant device 200 is implanted with the flanged tissue engagement surface engaging tissue adjacent the proximal end of the fistula.

With continued reference to FIGS. 2-5, the conduit 208 has a first exterior width 224 that is a maximum exterior width of the conduit 208 as defined by the maximum extents of the anchor protrusions 212 transverse to the length of the conduit 208. The conduit 208 has a second exterior width 226 that is a minimum exterior width of the conduit 208 defined between the most recessed portions of the areas of recess 214. In the embodiment shown in FIGS. 2-5, the height of the anchor protrusions 212 is equal to one-half the difference between the first exterior width 224 and the second exterior width 226 of the conduit 208. In the configuration of the head 206 shown in FIGS. 2-5, the first dimension 220 of the head is larger than both the first exterior width 224 and the second exterior width 226 of the conduit 208, while the second dimension 222 of the head is approximately equal to the second exterior width 224 of the conduit 208.

With continued reference to FIGS. 2-5, the anchor protrusions 212 are in the form of spaced circumferential ridges having a width that is at a maximum at the bottom of the ridges located adjacent the areas of recess 214, and which width tapers to a minimum at the top of the ridges 212 located away from the recess areas 214. Other configurations for anchor protrusions are possible, and all anchor protrusions on an implant device need not be of the same size, geometry or height. Likewise, areas of recess may have varying configurations, and not all recesses on an implant device need to be the same size or configuration. The implant device 200 has a length 228 including the depth 223 of the head 206 and the length of the conduit 208. The anchor protrusions 212 are on a longitudinal portion 230 of the conduit 208.

Figure 6:
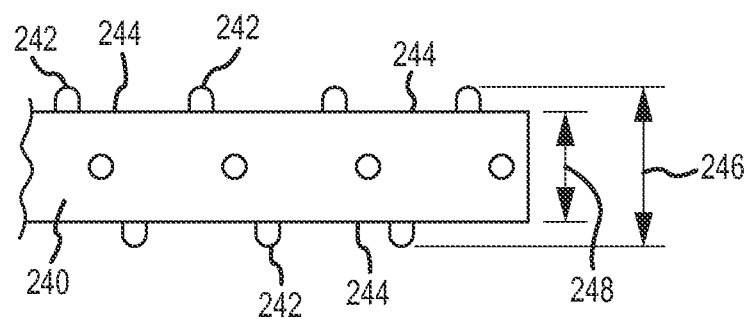
FIG. 6 is a partial side view of an embodiment of an implant device.
Figure 7:
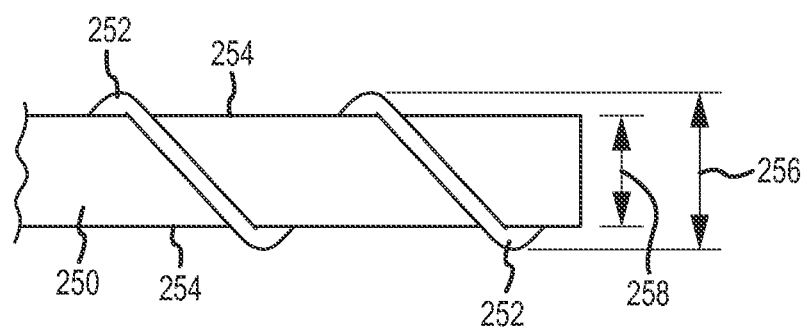
FIG. 7 is a partial side view of an embodiment of an implant device.

Referring now to FIG. 6, an alternative embodiment is shown of a conduit 240 of an implant device having anchor protrusions 242 in the form of knobs, or buttons, and areas of recess 244 adjacent the anchor protrusions 242. The conduit 240 has a first exterior width 246 defined by the anchor protrusions 242 and a smaller, second exterior width 248 defined by the areas of recess 244. An example of another configuration for anchor protrusions is shown in FIG. 7. As shown in FIG. 7, a conduit 250 of an implant device has anchor protrusions 252 and areas of recess 254 on the exterior surface of the conduit 250. The anchor protrusions 252 are in the form of a continuous spiral ridge extending along a portion of the longitudinal length of the conduit 250. The conduit 250 has a first exterior width 256 defined by the anchor protrusions 254 and a smaller, second exterior width 258 defined by the areas of recess 254. As with the embodiments shown in FIGS. 2-5, the conduit embodiments shown in FIGS. 6 and 7 include a height of the anchor protrusions that is equal to one half the difference between the larger and smaller outer diameters of the respective conduits. As will be appreciated from the embodiments of FIGS. 6 and 7, the first exterior width is determined as the width of an envelope volume that contains the anchor protrusions.

Figure 8:
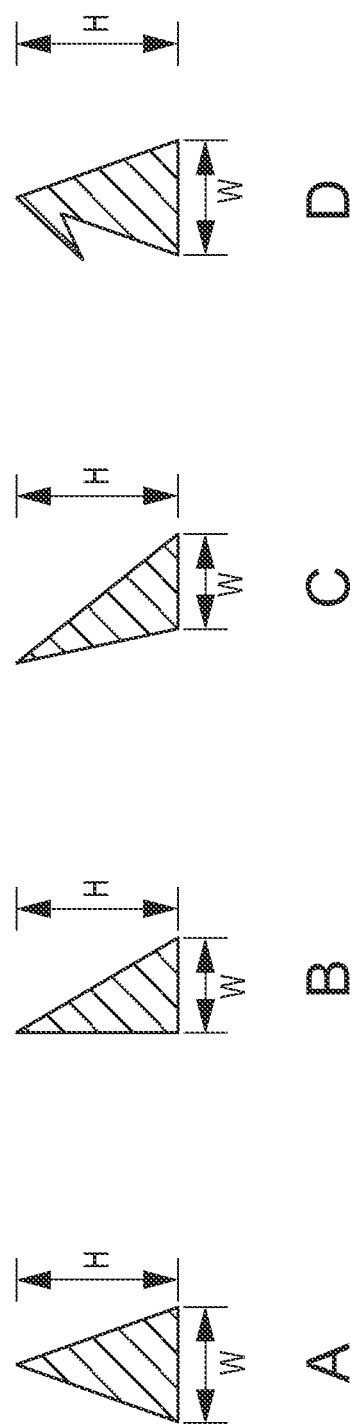
FIG. 8 is an illustration of cross-sections of various configurations for anchor protrusions for an implant device.

FIG. 8 shows examples of some shapes for anchor protrusions that include a tapering width in a direction from the base of the anchor protrusion toward a top of the anchor protrusion. FIG. 8 shows cross-sections of anchor protrusion configurations (designated A-D), each having a greater width at the base than at the top. The height (H) and base width (W) of the anchor protrusions are indicated in FIG. 8. The cross-sections shown in FIG. 8 may, for example, be across a ridge (e.g., circumferential ridge, spiral ridge), a knob protrusion or other anchor protrusion form. All of the anchor protrusion configurations A-D in FIG. 8 are shown with a leading side of the anchor protrusion on the right side and a trailing side on left side of the anchor protrusion. By leading side it is meant a side that enters the fistula first when a conduit containing the anchor protrusion is inserted into the fistula for implantation. By trailing side it is meant the side opposite the leading side and that enters the fistula after the leading side.

FIG. 9 shows some different example configurations (designated E-H) for a head for an implant device. For each head configuration, the length dimension (L) and width dimension (W) of the head configurations are shown. The heads of configurations E-H are shown on end showing the face surface (surface facing away from the fistula when implanted) and the opening of the internal passage at the proximal end of the implant device. For each of the head configurations E-H, the length and width of the face surface and the opposing flanged tissue engagement surface are the same. As shown in FIG. 9, head configuration E has a circular outer edge, and thus has equal length and width dimensions. Head configuration F has an elongated length dimension relative to width dimension, similar to that shown in the implant device embodiment described with reference to FIGS. 2-5. Head configuration G has an elongated length dimension relative to the width dimension, similar to configuration F, but for configuration G the internal passage opening at the proximal end of the implant device has an elliptical cross-section, rather than a circular cross-section as is the case for configurations E and F. Head configuration H has a crescent-shaped head with a significantly larger length dimension than width dimension. The internal passage for configuration H is also shown with an elliptical cross-section. Configurations F-H, with a larger length than width, are advantageously configured for use with fistulas opening into the orbit between the medial canthus and the medial side of an adjacent eyeball, for example between the plica semilunaris and the lacrimal caruncle, and preferably with the length dimension of the head extending generally in a direction from the bottom of the orbit toward the top of the orbit next to the eyeball, and for configuration H with the concave side of the crescent disposed toward the eyeball and the convex side of the crescent disposed towards the lacrimal caruncle. An "aspect ratio" of the head refers to a ratio of the length of the head to the width of the head. Configuration E has an aspect ratio of 1:1, while configurations E, F, G and H each has an aspect ratio of greater than 1:1.

Figure 10:
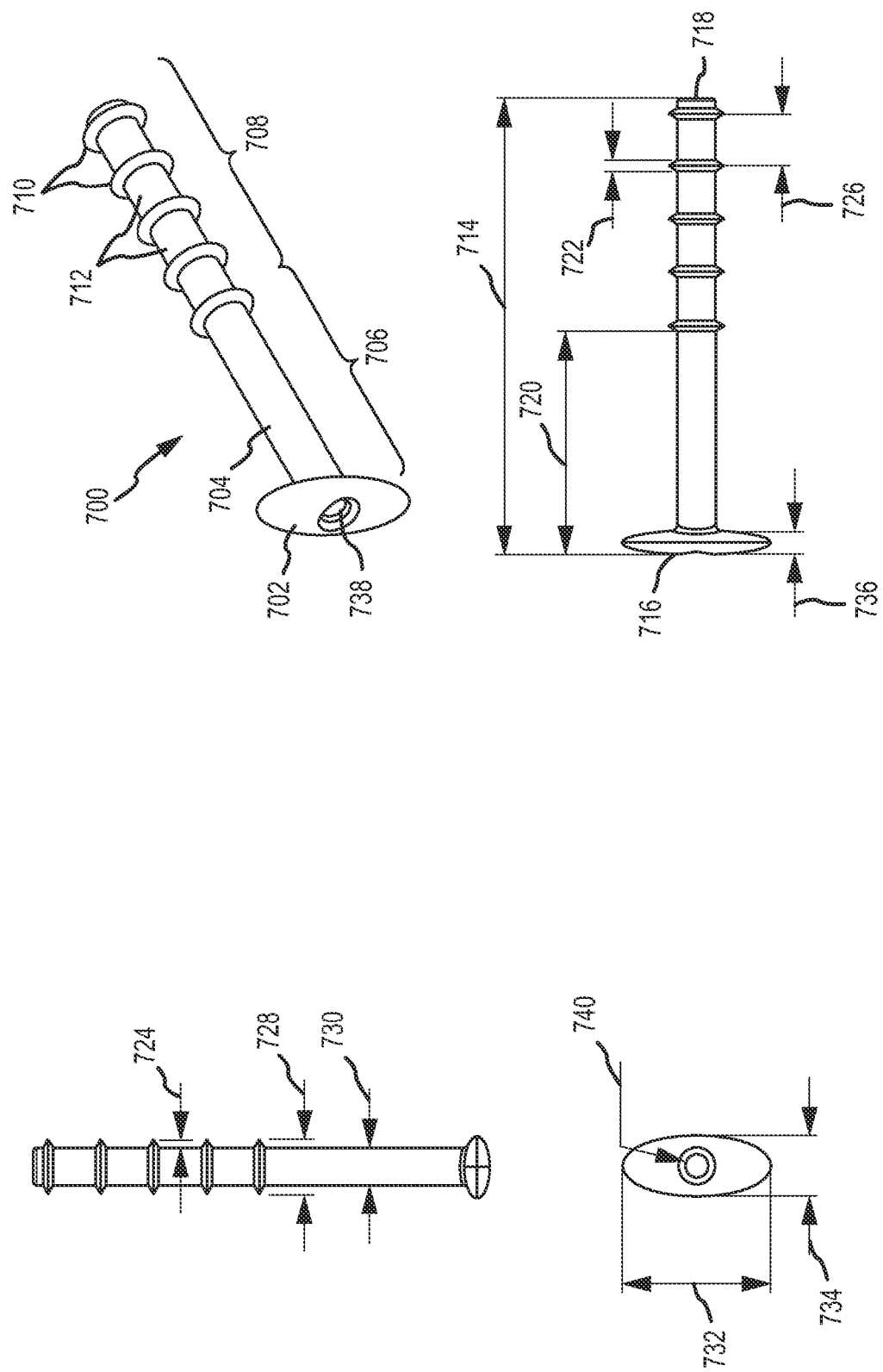
FIG. 10 shows perspective, top, side and end views of an embodiment of an implant device.
Figure 11:
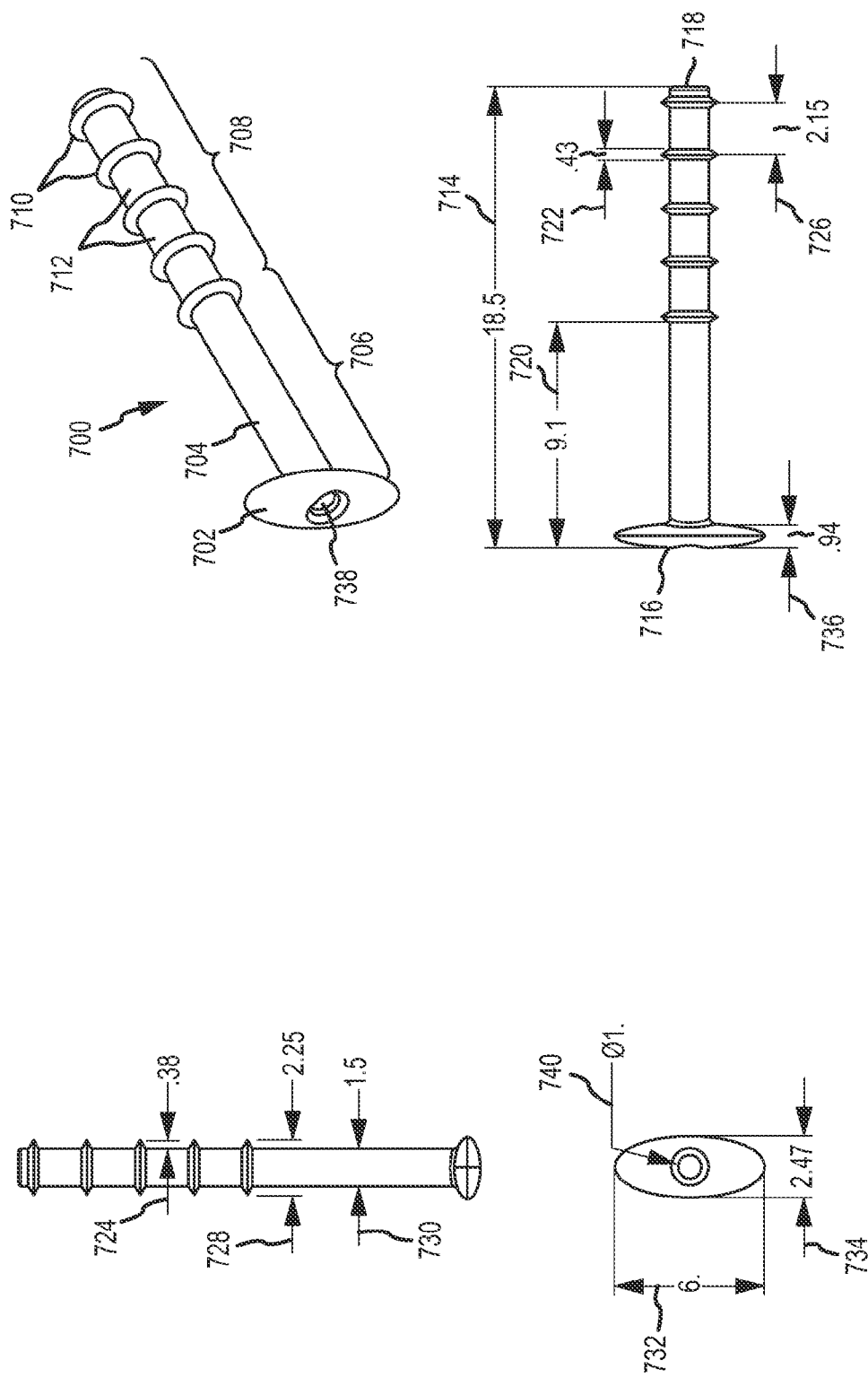
FIG. 11 shows perspective, top, side and end view of an embodiment of an implant device showing some possible example dimensions.

FIG. 10 shows an implant device 700 with a head 702 and a conduit 704. The conduit 704 includes a first longitudinal portion 706 and a second longitudinal portion 708 disposed distal of the first longitudinal portion 706. The first longitudinal portion 706 includes a smooth exterior surface and the second longitudinal portion 708 includes an anchoring surface feature including anchor protrusions 710, in the form of spaced circumferential ridges, and recess areas 712 between the anchor protrusions 710. The length of the first longitudinal portion 706, located before the beginning of the anchoring surface feature of the second longitudinal portion 708, may advantageously be disposed in conjunctival tissue adjacent the head 702 when implanted to "float" for patient comfort. and to facilitate performance of post-implantation medical procedures without disruption of implant anchor stability. The anchoring features of the second longitudinal portion 708 may advantageously be located a distance from the head 702 so that one or more of the anchor protrusions 710 are located in the vicinity of the paranasal sinus bone wall that is penetrated by the implant device 700 when implanted, preferably with one or more of the anchor protrusions disposed on each side of the bone. In the embodiment shown in FIG. 10, the exterior width of the conduit 704 is substantially the same for the whole length of the first longitudinal portion 706 and in the recess areas 712 of the second longitudinal portion 708. The conduit 704 has a circular cross-section, so that the exterior width of the conduit 704 at any location along the conduit 704 is represented by the diameter of the circular cross-section of the conduit 704 at that location. As shown in FIG. 10, the implant device 700 has a length 714 from a proximal end 716 to a distal end 718 of the implant device 700. The beginning of the second longitudinal portion 708 is located a distance 720 distal from the proximal end 716. The anchor protrusions 710 have a width 722 at the base of the anchor protrusions 722 and a height 724 above the adjacent recess areas 712. The anchor protrusions 710 are spaced on a center-to-center spacing 726. The conduit 704 has a maximum exterior width 728 corresponding with the tops of the anchor protrusions 710, equal to the diameter of the circle of the cross-section through the conduit 704 at the top of the anchor protrusions 710. The conduit 704 has a minimum exterior width 730 along the length of the first longitudinal portion 706 and in the recess areas 712 of the second longitudinal portion 708 of the conduit 704, and which is equal to the diameter of the circular cross-section at those locations. The head 702 has a length dimension 732, a width dimension 734 and a depth dimension 736. The implant device 700 has an internal passage 738 extending between the proximal end 716 and the distal end 718 and through the length of the conduit 704. The internal passage 738 has a width 740, which in this embodiment is equal to a diameter of the circular cross-section of the internal passage 738. FIG. 11 shows the same implant device 700 as shown in FIG. 10 with some exemplary dimensions, in millimeters, for one nonlimiting example for a configuration for the implant device 702.

Figure 12:
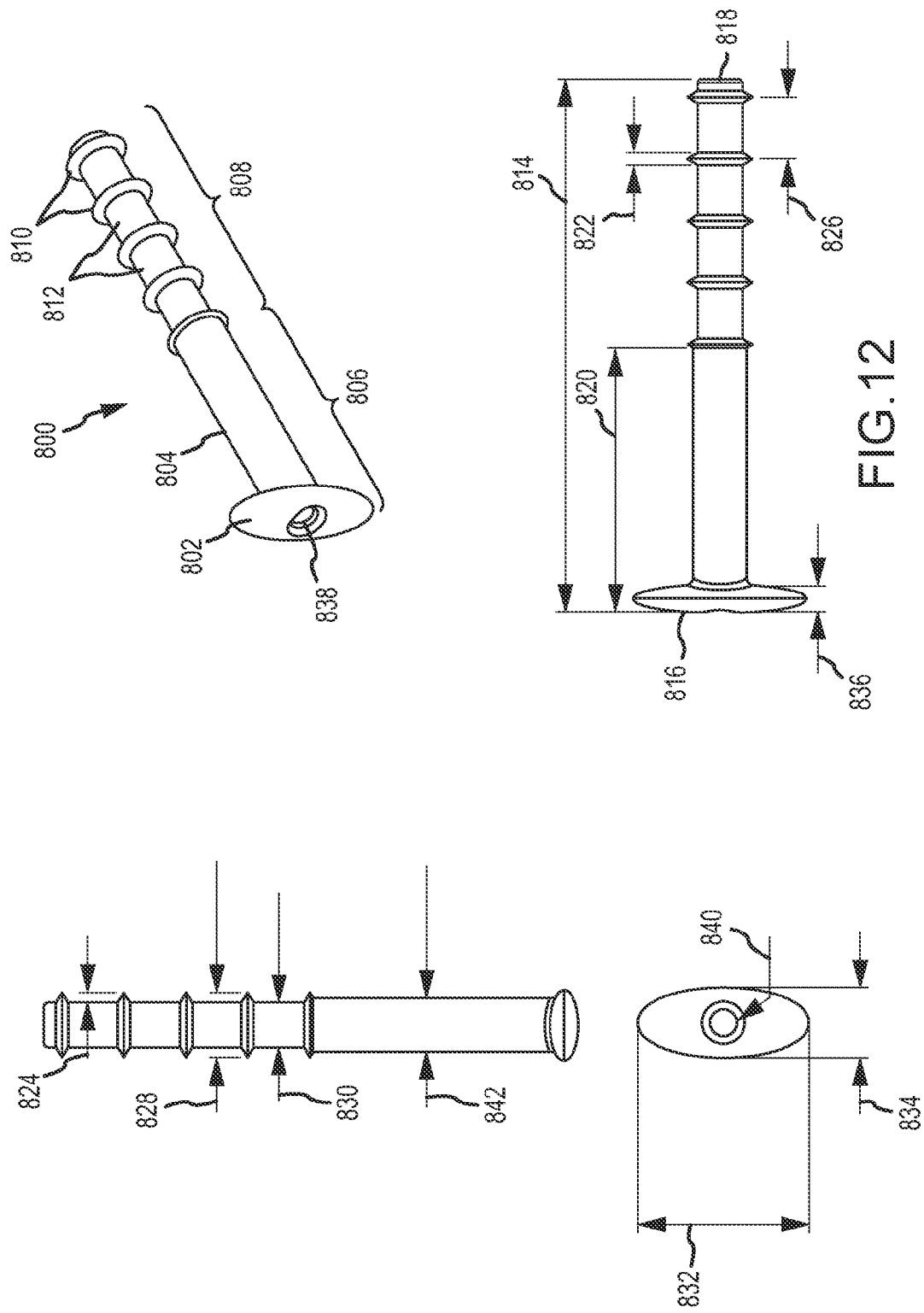
FIG. 12 shows perspective, top, side and end views of an embodiment of an implant device.

FIG. 12 shows an implant device 800 that is similar to the implant device 700 shown in FIGS. 10 and 11, except including a first longitudinal portion of a conduit having a thicker wall than recess areas of the anchoring surface feature of a second longitudinal portion of the conduit. The thicker wall in the first longitudinal portion of the conduit provides added rigidity to that portion of the conduit to facilitate pushing the implant device 800 into place during an implantation procedure, while the thinner wall in the recess areas of the second longitudinal portion of the conduit permit that portion to more easily deform and fit through a fistula during implantation and then to expand to engage tissue and anchor the implant device 800. More specifically as shown in FIG. 12, the implant device 800 includes a head 802 and a conduit 804. The conduit 804 has a first longitudinal portion 806 and a second longitudinal portion 808 located distal of the first longitudinal portion 806. The first longitudinal portion 806 includes a substantially smooth exterior surface with a substantially constant exterior width, which is the diameter of the circular cross-section of the conduit 804 along the first longitudinal portion 806. The second longitudinal portion 808 includes an anchoring surface feature including anchor protrusions 810, in the form of circumferential ridges, and recess areas 812 in the spaces between the anchor protrusions 810. Various dimensions of the implant device 802 are illustrated in FIG. 12, similar to the illustration provided for the implant device 700 in FIG. 10. The implant device 800 has a length 814 from a proximal end 816 to a distal end 818 of the implant device 800. The beginning of the second longitudinal portion 808 is located a distance 820 distal of the proximal end 816. The anchor protrusions have a width 822 at the base and a height 824 above the adjacent recess areas 812. The anchor protrusions are spaced on a center-to-center spacing 826. The conduit 804, and also the second longitudinal portion 808, has a maximum exterior width 828 occurring at the tops of the anchor protrusions 810, and equal to the diameter of the circular cross-section of the conduit 804 through the tops of the anchor protrusions 810. The conduit 804, and the second longitudinal portion 808, of the conduit 804 have a minimum exterior width 830 located at the recess areas 812. The head 802 has a length dimension 832, a width dimension 834 and a depth dimension 836. The implant device 800 has an internal passage 838 extending between the proximal end 816 and the distal end 818 and through the length of the conduit 804. The internal passage 838 has a width 840, which in the embodiment shown in FIG. 12 is equal to a diameter of the circular cross-section of the internal passage 838.

Figure 13:
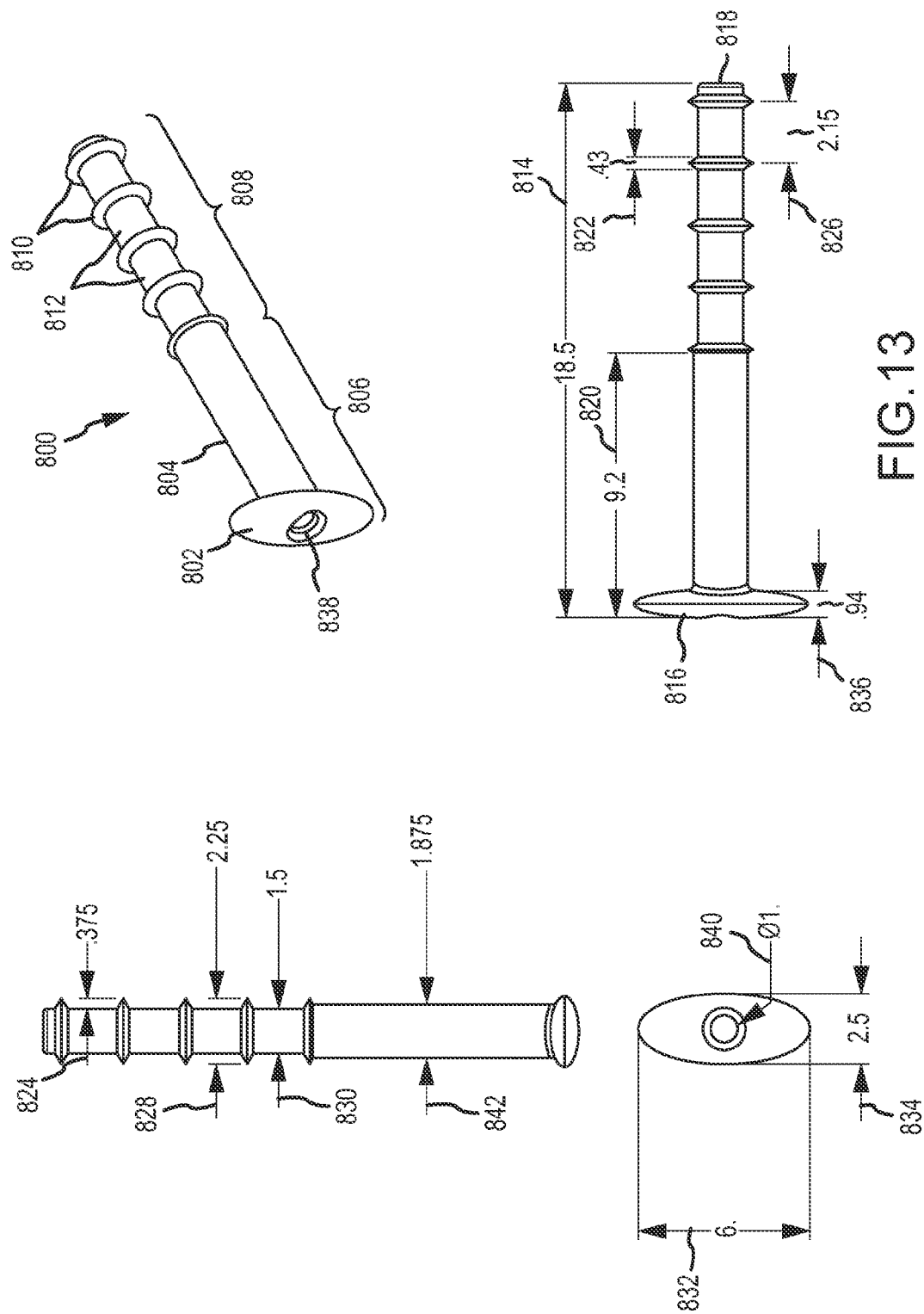
FIG. 13 shows perspective, top, side and end view of an embodiment of an implant device showing some possible example dimensions.

With continued reference to FIG. 12, the wall thickness of the conduit 804, (thickness of the wall between the internal passage 838 and the exterior surface of the conduit 804) is greater along the first longitudinal portion 806 than in the recess areas 812 of the second longitudinal portion 808. The internal passage 838 has a constant width along the length of the conduit 804, such that the greater wall thickness of the conduit 804 along the first longitudinal portion 806 results in an exterior width 842 that is larger than the minimum exterior width 830 in the recess areas 812. The maximum exterior width 828 at the anchor protrusions 810 is larger than the exterior width 842 along the first longitudinal portion 806. FIG. 13 shows some exemplary dimensions, in millimeters, for one nonlimiting example for a configuration of the implant device 800.

Figure 14:
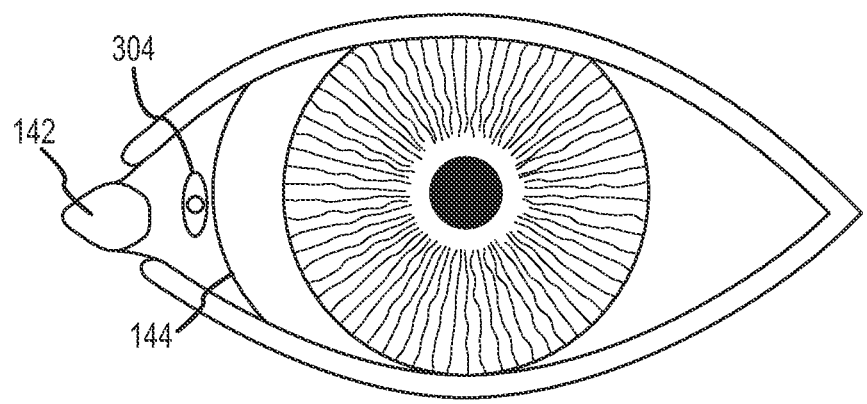
FIG. 14 is an illustration showing an embodiment for placement of an implant device with a head of the implant device located within the orbit between the lacrimal caruncle and plica semilunaris.

FIG. 14 shows an example of an implant device with a conduit passing through a fistula formed from the orbit subconjunctivally between the lacrimal caruncle 142 and the plica semilunaris 144, and showing an example location for the head 304 of the implant device disposed in the orbit between the lacrimal caruncle 142 and the plica semilunaris 144. The head 304 is shown with an elongated configuration, such as for example a head configuration shown in any of FIGS. 2-5, FIGS. 10-13, or configurations F-H shown in FIG. 11.

Referring now to FIGS. 15-18, some examples of surgical procedures involving forming a fistula and implanting an implant device to provide access to a paranasal sinus, and some example surgical tools for use therewith, will now be described.

Figure 15:
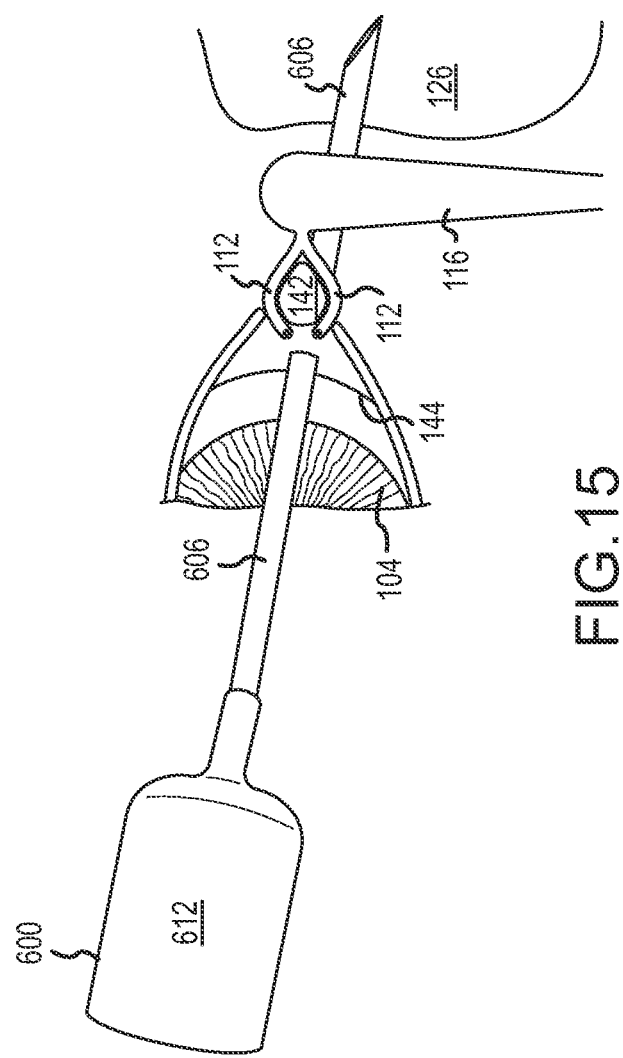
FIG. 15 is an illustration showing use of a surgical tool, in the form of a cutting tool, to form a fistula between the orbit and an ethmoid sinus during a surgical procedure.

In FIG. 15 a surgical tool, in the form of an entry tool 600 is shown in the process of making a fistula through tissue between the lacrimal caruncle 142 and the plica semilunaris 144. Numbering of anatomical parts is the same as in FIG. 1. The fistula is formed through tissue between the conjunctival sac in the orbit and the ethmoid sinus 126. The route for the fistula would be consistent with general fistula route 132 as shown in FIG. 1. The entry tool 600 includes a hollow working member 606 with a hollow cutting distal tip 610 with a shape suitable to cut away tissue to form a fistula from the conjunctival sac to the ethmoid sinus 126. The entry tool 600 may also be referred to as a cutting tool and the working member may also be referred to as a cutting member. The entry tool 600 includes a hand-manipulable handle 612. The handle 612 may be advanced or retracted to advance or retract the hollow working member 606. As shown in FIG. 15, the distal cutting tip 610 has been advanced from a location in the conjunctival sac between the caruncle 142 and the plica semilunaris 144 to form a fistula between the conjunctival sac and the ethmoid sinus 126. As shown, the fistula passes behind the caruncle 142, canaliculi 112 and nasolacrimal duct 116 to access the ethmoid sinus 126.

Figure 16:
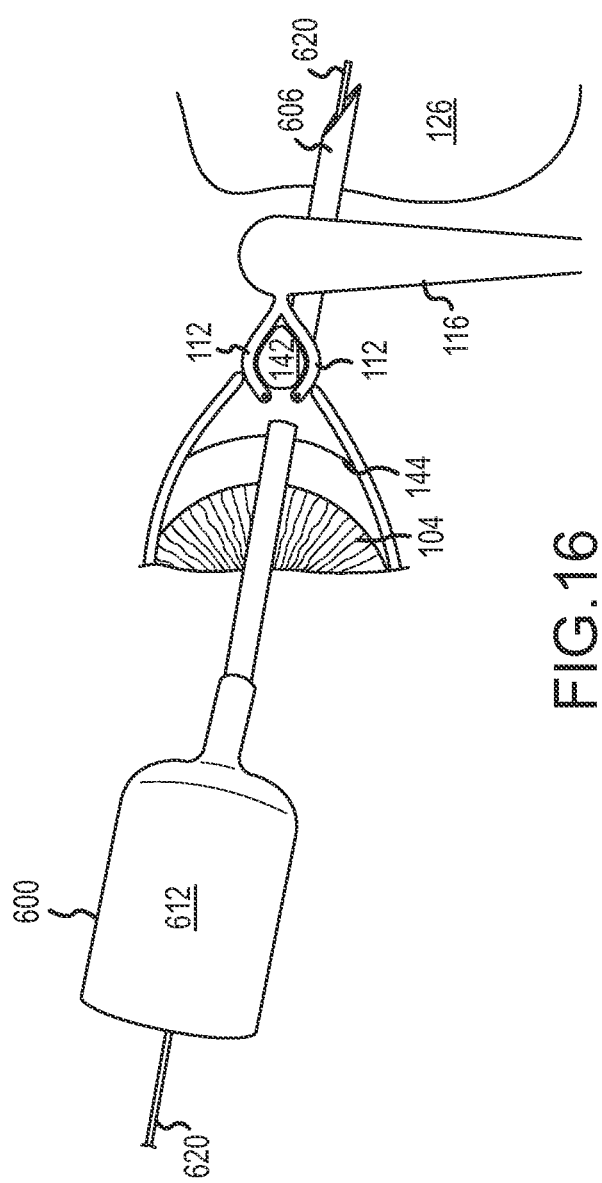
FIG. 16 is an illustration showing insertion of a guide wire following formation of a fistula during a surgical procedure.
Figure 17:
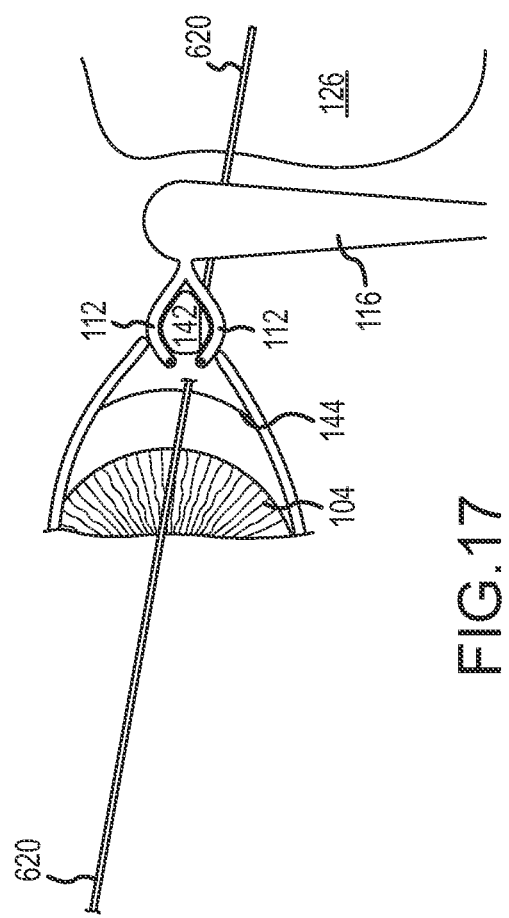
FIG. 17 is an illustration showing a guide wire in place as a guide to a fistula during a surgical procedure.

After the entry tool 600 has been used to initially form a fistula to the ethmoid sinus 126, then a guide wire or other guide member may be inserted through an internal passage extending through the handle 612 and the hollow working member 606. FIG. 16 shows a guide wire 620 inserted through the handle 612 and the working member 606. After insertion of the guide wire 620, entry tool 600 may be retracted and removed from the fistula, leaving the guide wire 620 in place as a guide to and through the fistula, as shown in FIG. 17. The guide wire 620 is now available for guiding additional tools to and through the fistula into the ethmoid sinus 126.

Figure 18:
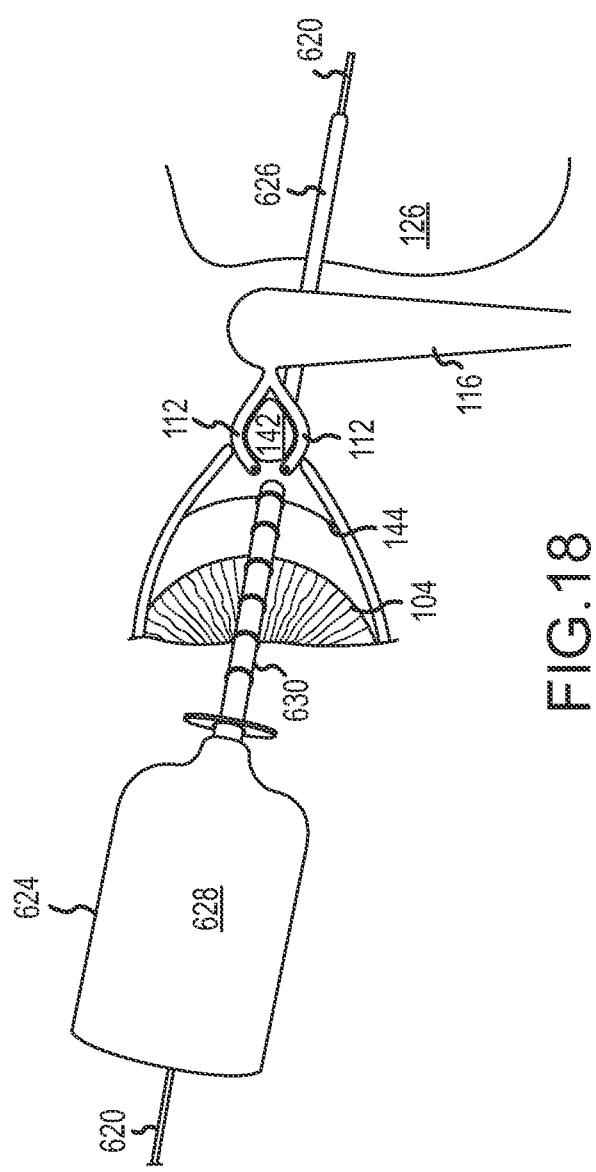
FIG. 18 is an illustration showing use of a surgical tool, in the form of a carrier tool, for implantation of an implant device during a surgical procedure.
Figure 19:
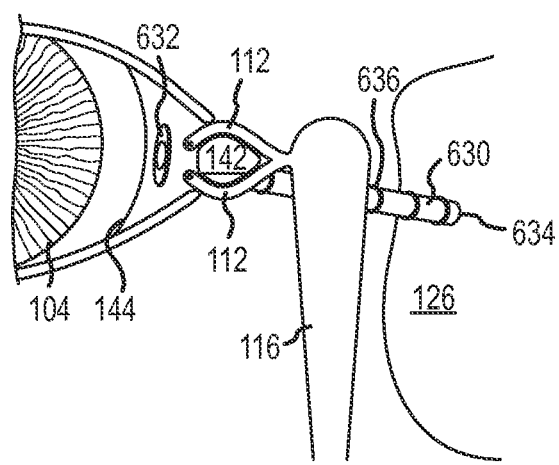
FIG. 19 is an illustration showing placement of an implant device following implantation during a surgical procedure.

With reference now to FIG. 18, the guide wire 620 has been used to guide a surgical tool, in the form of an implant tool 624. The implant tool may also be referred to as a carrier tool. The implant tool 624 includes a hollow working member 626 and a hand-manipulable handle 628. The working member 626 may have a blunt distal tip, as shown in FIG. 18, since the working member 626 may not need to cut additional tissue following formation of the fistula using the entry tool 600, provided that the fistula has already been formed to a final desired size. The working member 626 may also be referred to as a carrier member. The implant tool 624 includes an internal passage passing through the handle 628 and the hollow working member 626. As shown in FIG. 18, the guide wire 620 has been threaded through the internal passage of the implant tool 624 to guide the hollow working member 626 to and through the fistula and into the ethmoid sinus 126. An implant device 630 is mounted on the hollow working member 626 of the implant tool 624. FIG. 18 shows the implant tool 624 advanced to a point where the distal end of the implant device 630 is in the vicinity of the proximal end of the fistula opening into the conjunctival sac. From this position, the implant device 630 may be advanced into the fistula with a head of the implant device 630 disposed adjacent the conjunctiva in the conjunctival sac and a distal end of the implant device 630 extending into the ethmoid sinus 626. For example, a surgeon may slide the implant device 630 down the hollow working member 626 for placement through the fistula for implantation or the surgeon may advance the handle 628 to have the handle push the implant device 630 into the fistula for implant placement. The outside diameter of the hollow working member 626 may be sized to closely fit within the inside diameter of the implant device 630 to help prevent the implant device 630 from bunching-up and laterally deforming as the implant device is pushed into the fistula. The handle 628 and the hollow working member 626 form a carrier for the implant device 630. The handle 628 may be retracted and the hollow working member 626 disengaged from the implant device 630 after the implant device has been appropriately positioned for implantation through the fistula. FIG. 19 shows the implant device 630 as implanted and following disengagement of the hollow working member 626 of the implantation tool 624. As implanted, a head 632 at the proximal end of the implant device 630 is located adjacent the conjunctiva in the conjunctival sac within the orbit between the caruncle 142 and the plica semilunaris 144 and the distal end 634 of the implant device 630 is located in the ethmoid sinus 126. Some anchor protrusions 636 of the conduit of the implant device 630 are disposed within the fistula to engage tissue and help anchor the implant device 630. The implant device 630 may be used to provide access to the ethmoid sinus 126 to perform medical procedures or treatments, for example to administer a treatment composition to the ethmoid sinus or to aspirate fluid from the ethmoid sinus.

The procedure as described with reference to FIGS. 15-19 permits the working member 606 of the entry tool 600 to have a larger diameter working member 626 to form a fistula of appropriate size for accommodating the implant device 630 which is then implanted in a separate step using the implant tool 624 with the implant device 630 carried on to the working member 626, which may advantageously have a smaller diameter than the working member 606 used to form the fistula. As an alternative, an intermediate step to dilate the fistula or to cut away additional tissue to a desired hole size for implantation may be performed between initially forming a fistula with the entry tool 600 and implanting the implant device 630 using the implant tool 624.

Referring again to FIG. 15, optionally, one or more procedures may be performed prior to retracting the hollow working member 606. One or more fluids may be injected through the hollow working member 606. For example, contrast media may be injected through the hollowing working member 612 and may be imaged to confirm that the fistula has been formed to the proper location prior to proceeding with implantation.

Reference is made to FIGS. 20-30 in relation to fluid manipulation through an implant device, such as may be desirable to perform as part of a medical procedure ancillary to implantation of the implant device or a medical procedure performed at a later date following implantation of an implant device.

FIG. 20 shows a paranasal sinus fluid manipulation tool 900 that includes a syringe 902 and a fluid transmission attachment 904 connected with the syringe 902, such as through a luer connection between the syringe 902 and the fluid transmission attachment 904. The fluid transmission attachment 904 includes at a distal end a paranasal sinus fluid connection engagement structure configured for insertion into the palpebral fissure to engage the head of a paranasal sinus access implant device when the implant device is implanted between the medial canthus and the medial side of an adjacent eyeball to provide access to a paranasal sinus. By engaging the head of an implant device with the engagement structure of the fluid transmission attachment 904, the fluid manipulation tool 900 may be engaged with the implant device to establish fluid communication between the fluid container within the barrel of the syringe 902 and the internal passage of the implant device and to permit fluid manipulations to be performed, for example by advancing the piston in the barrel of the syringe 902 to expel fluid from the barrel of the syringe 902 into the internal passage of the implant device for delivery to a paranasal sinus or retracting the piston in the barrel of the syringe 902 to create a vacuum in the barrel of the syringe 902 to apply suction to the internal passage of an implant device to aspirate of fluid from a paranasal sinus into and through the internal passage and into the barrel of the syringe 902.

FIG. 21 shows a paranasal sinus fluid treatment apparatus including the same embodiment of the fluid manipulation tool 900 shown in FIG. 20 with the engagement structure of the fluid transmission attachment 904 engaged with the head of an implant device 906. Such a paranasal sinus fluid treatment apparatus as shown in FIG. 21 may be formed during a fluid manipulation procedure with the implant device implanted in a patient to provide fluid access to a paranasal sinus that is an object of the fluid manipulation procedure. Alternatively, such a paranasal sinus fluid treatment apparatus as shown in FIG. 21 may be formed before the implant device has been implanted in a patient, for example during manufacturing or for testing purposes or in preparation for performing a procedure.

Figure 22:
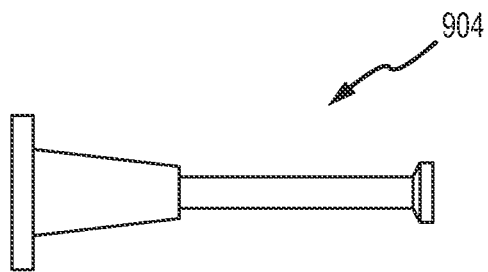
FIGS. 22-26 illustrate an embodiment of a fluid transmission attachment shown in FIGS. 20 and 21 including a paranasal sinus fluid connection engagement structure for engagement with a head of a paranasal sinus access implant device.
Figures 23, 24:
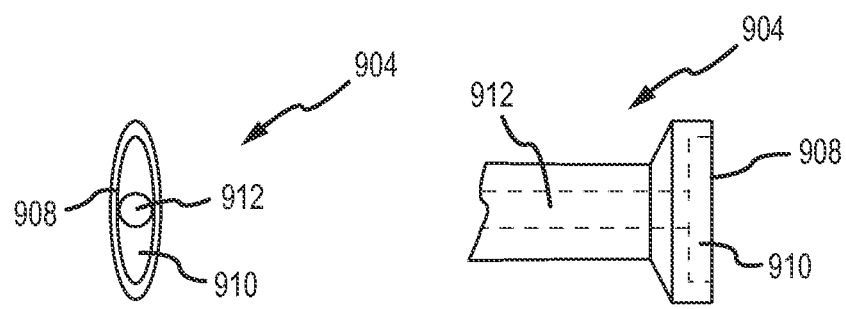
Figure 25:
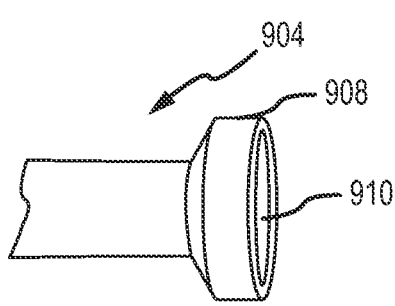

FIG. 22 shows the fluid transmission attachment 904 of FIG. 20 as a separate piece, and not connected with a syringe. FIGS. 23-25 show details of the engagement structure disposed adjacent a distal end of the fluid transmission attachment 904. Such an engagement structure could also be disposed on a distal portion of a paranasal sinus fluid manipulation tool not as part of a removable attachment. For example, the engagement structure could be on a distal extension that is permanently attached to or is integral with a syringe.

Figure 26:
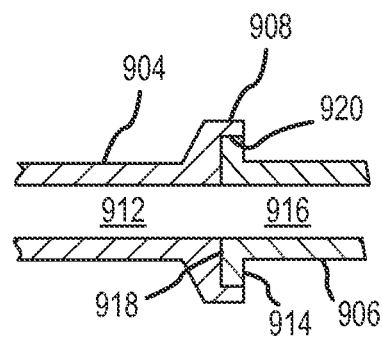
Figures 27, 28:
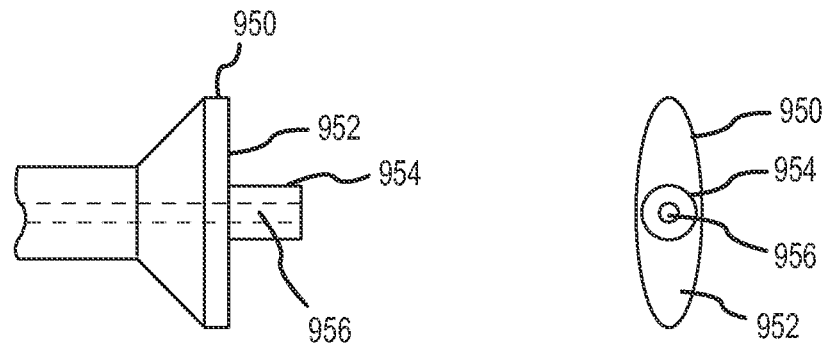
FIGS. 27-30 illustrate an embodiment of a paranasal sinus fluid connection engagement structure for engagement with a head of a paranasal sinus access implant device.
Figure 29:
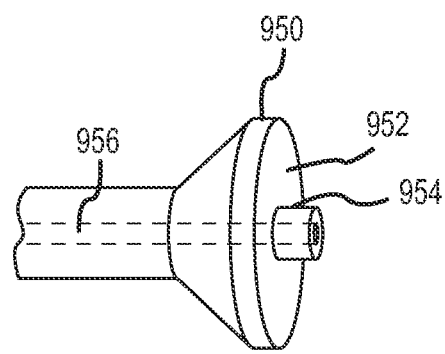

As shown in FIGS. 23-25, the engagement structure 908 of the fluid transmission attachment 904 includes a recess area in the form of a receptacle 910 for receiving the head of an implant device when the engagement structure is engaged with the implant device. A fluid conduit 912 through the fluid transmission attachment 904 opens into the receptacle 910 to permit fluid communication between the conduit 912 and the internal passage of an implant device when the head of an implant device is engaged with the engagement structure 904. As best seen in FIG. 23, the receptacle 910 of the engagement structure has an oval shaped insertion cross-section configured to the insertable into the palpebral fissure to access and engage the head of an implant device having a corresponding oval shape disposed between the medial canthus and a medial side of the adjacent eyeball, thereby permitting performance of fluid manipulations through the internal passage of the engaged implant device when implanted. FIG. 26 shows the engagement structure 908 of the fluid transmission attachment 904 engaged with a head 914 of the implant device 906 shown in FIG. 21. As shown in FIG. 26, the conduit 912 of the fluid transmission attachment 904 is aligned with and in fluid communication with an internal passage 916 of the implant device 906. As seen in FIG. 26, the engagement between the engagement structure 908 and the head 914 includes flush surface contact 920 where the facing surfaces at the bottom of the receptacle 910 and the face of the head 914 are in contact around the periphery of the opening of the internal passage 916 in the head 914. The engagement also includes overlapping surface contact 920 where peripheral edge portions of the head 914 overlap in an axial direction and contact internal wall surfaces of the receptacle 910 of the engagement structure 908.

Figure 30:
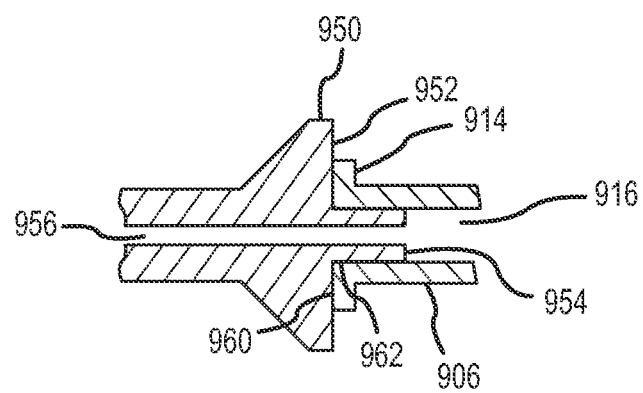

Reference is now made to FIG. 27-30 showing an alternative configuration for a paranasal sinus fluid connection engagement structure for a paranasal sinus fluid manipulation tool. Such an engagement structure may or may not be on a fluid transmission attachment. As shown in FIGS. 27-30, a paranasal sinus fluid connection engagement structure 950 includes a contact face 952 for making flush surface contact with the face of the head of an implant device. The engagement structure 950 includes an insertion stub 954 configured to be inserted into the internal passage of an implant device through an opening in a head of the implant device when the engagement structure 950 is engaged with the implant device. A fluid conduit 956 extends through the insertion stub 954 and opens at a distal end of the insertion stub 954. FIG. 30 shows the engagement structure 950 engaged with the head 914 of the implant device 906 of FIG. 21, and with the insertion stub 954 inserted through an opening in the head 914 and into the internal passage 916 of the implant device 906. As shown in FIG. 30, the head 914 and the engagement between the engagement structure 950 and the head 914 includes flush surface contact 960 between the face of the head 914 and the contact face 952 of the engagement structure 950. The engagement also includes overlapping surface contact 962 between an exterior surface of the insertion stub 954 and an interior wall surface of the internal passage 916 in the head 914. The insertion stub 954 helps orient the engagement structure 950. As seen best in FIG. 28, the engagement structure 950 has an oval-shaped insertion cross-section configured for insertion into the palpebral fissure between the medial canthus and the medial side of the adjacent eyeball to access and engage the head of an implant device, to thereby permit performance of fluid manipulations through the internal passage of the engaged implant device.

As an alternative to piercing and dilating a hole to form a fistula, a method for implantation may include cutting tissue away to leave the bone that is penetrated more in-tact and with better integrity in the vicinity of the hole to help retain the implant device in place following implantation. The cutting may be performed, for example, with a cutting tool such as a needle or cannula that cuts tissue or a drill that drills out the tissue. A method may include cutting an initial hole at the location of the desired fistula, and then using a guide member and further tools to complete an implantation procedure. For example, the initial cut may be to make a preliminary hole and a larger gauge needle or cutting cannula may be guided by the guide member to cut the fistula to the final desired size for implantation of the implant device. Alternatively, the initial hole that is cut may be of a final desired size for implantation of the implant device. After the hole has been made to the desired size, the guide member may then be used to guide the implant device or a carrier tool on which the implant device is mounted to the fistula for implantation of the implant device. As one example, a small gauge needle may be used to form an initial cut, and a guide wire may then be inserted through the needle and into the fistula to maintain control of the fistula. The smaller gauge needle may then be retracted and the second cutting tool, in the form of a larger gauge needle, may be slid over the guide wire and conducted to the proper location to cut the fistula to the proper size for implantation of the implant device. A kit for performing such an operation my include the implant device, the smaller gauge needle, the guide wire (as the guide member) and the larger gauge needle as the cutting tool for making the fistula to the final desired size. As another example, the initial cutting tool, or a portion thereof may be used as the guide member for the subsequent cutting tool. For example, the initial cut may be made using a smaller gauge needle having a handle, such as a spinal needle or similar design. Following the initial cut, the handle, or head, may be cut off and removed from the smaller gauge needle and a cutting tool in the form of a larger gauge needle may then be slid over the smaller gauge needle to cut the hole to the final desired size for the fistula. The larger gauge needle may then be retracted and the implant device may be slid over the smaller gauge needle and conducted to the proper location for implantation. A kit for performing such an operation may include the implant device, the smaller gauge needle (which serves as the guide member) and the larger gauge needle as the cutting tool for making the fistula to the final desired size. Alternatively, a kit may include a single cutting tool (e.g., hollow needle or cutting cannula) sized to cut a hole of the final desired size through which the implant device is to be implanted, and without enlargement by further cutting or dilation.

Figure 31:
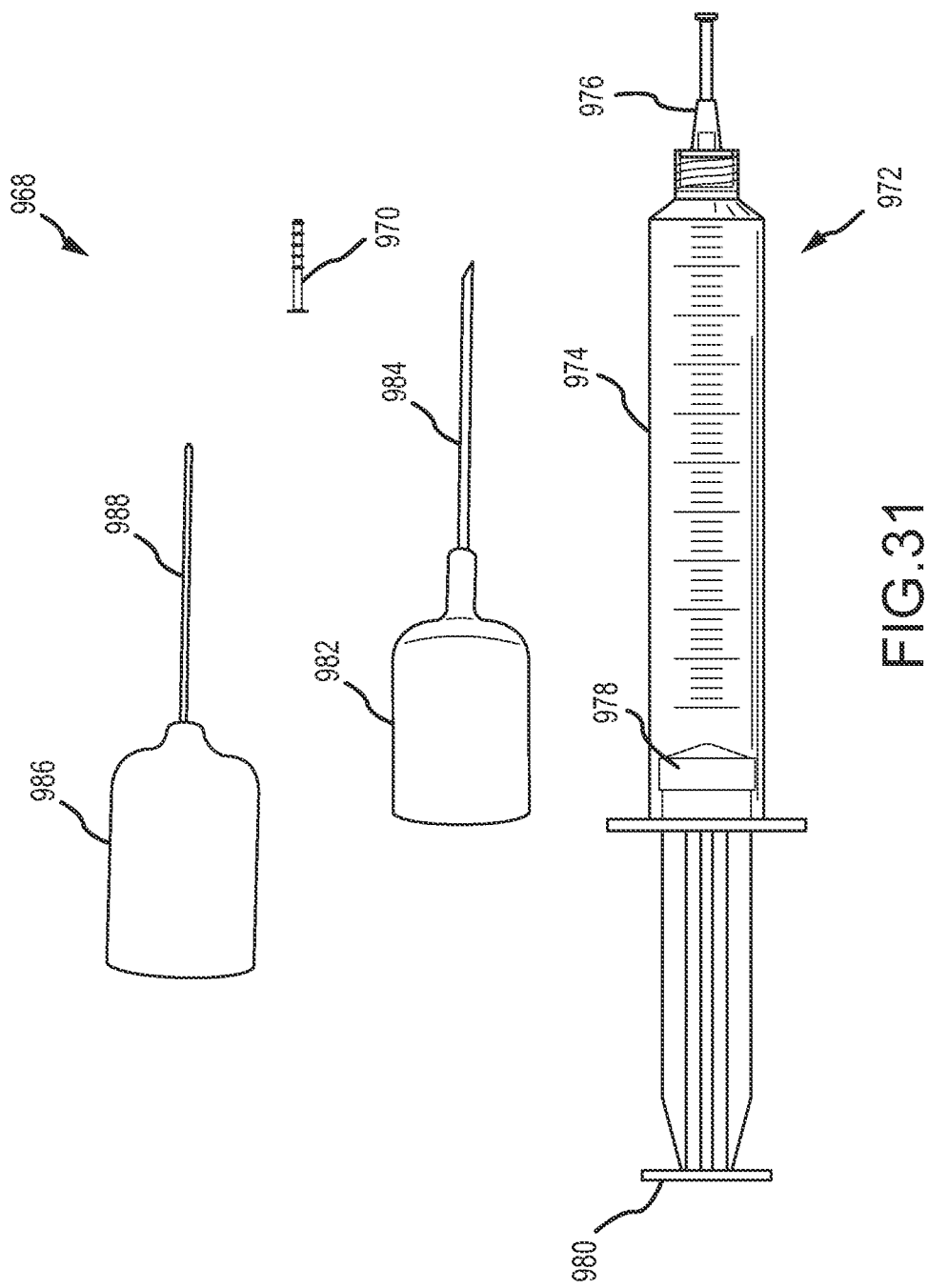
FIG. 31 illustrates an embodiment of a kit useful for performing fluid manipulations in relation to a paranasal sinus.

Referring now to FIG. 31, an example embodiment of a kit is shown that includes components for performing fluid manipulations in relation to a paranasal sinus through an engageable combination of a paranasal access implant device and a paranasal sinus fluid manipulation tool. As shown in FIG. 31, a kit 968 includes a paranasal sinus access implant device 970. The implant device 970 may for example have any design according to or with features shown or described in relation to any of FIGS. 2-13, or may have a different design. The kit also includes a paranasal sinus fluid manipulation tool 972, which includes a syringe 974 and a fluid transmission attachment 976. The fluid transmission attachment 976 includes an engagement structure adjacent a distal end to engage with a head on a proximal end of the implant device 970 to facilitate transmission of fluid from inside a barrel of the syringe 974 to an internal passage of the implant device 970. The syringe 974 includes a piston 978 disposed in the barrel of the syringe 974 and hand manipulable by advancement or retraction of a plunger 980 to move the piston 978 in the syringe barrel create pressure to expel fluid from the syringe barrel through the fluid transmission attachment 976 or to create a vacuum to suction fluid through the fluid transmission attachment 976 into the syringe barrel. The fluid manipulation tool 972 may be provided with the syringe 974 and the fluid transmission attachment 976 assembled as shown in FIG. 31, or may be provided with the syringe 974 and the fluid transmission attachment 976 as separate, disassembled pieces that are assemblable into the assembly as shown in FIG. 31. In some preferred implementations, the syringe 974 may be prefilled with a treatment composition disposed inside the barrel of the syringe 974. Such a prefilled syringe 974 may be provided in the kit 968 assembled with the fluid transmission attachment 976 as shown in FIG. 31, and preferably with a protective cap covering the fluid transmission attachment 976, and which cap is removable by a medical practitioner for use of the fluid manipulation tool 972 to perform a paranasal sinus fluid manipulation in engagement with a head of the implant device 970. The fluid transmission attachment 976 may be of a design according to or including any features shown in or described in relation to any of FIGS. 20-30, or may be of a different design. A treatment composition disposed in the barrel of the syringe 974 may be an irrigation liquid or a drug composition, for example as previously described.

The embodiment of the kit 968 as shown in FIG. 31 also includes tools for forming a fistula between the lacrimal apparatus in the orbit and a paranasal sinus, for example a frontal, maxillary or ethmoid sinus. As shown in FIG. 31, the kit 968 includes a cutting tool 982 having a hollow cutting member 984 (e.g., hollow needle) for cutting away tissue to form a fistula of a size suitable for implantation of the implant device 972 without enlargement by further cutting or dilation. Alternatively a kit could include a cutting tool with a smaller gauge cutting member or piercing member to form an initial hole and one or more additional tools (e.g., cutting tool with larger gauge cutting member and/or dilator) may be included in a kit to enlarge the initial hole to a final desired size for implantation. The cutting tool 982 may for example have a design according to or including features as shown or described in relation to either of FIGS. 15 and 16, or may be of a different design.

The kit 968 as shown in FIG. 31 also includes a carrier tool 986 having an carrier member 988, which has an outside diameter sized for insertion of the carrier member 988 through the internal passage of the implant device 970 to mount the implant device 970 on the carrier member 988 to carry the implant device 970 for implantation after a fistula has been formed to a desired size. The carrier tool 986 may for example have a design according to or including any features as shown in or described in relation to FIG. 18 or may be of a different design. The carrier tool 986 and the implant device 970 may be provided in the kit 968 as separate, assemblable pieces such as is shown in FIG. 31. Alternatively, the carrier tool 986 and the implant device 970 may be provided in the kit with the implant device 970 pre-mounted on the carrier member 988 in a configuration ready for use in an implantation procedure.

The cutting tool 982 and the carrier tool 986 may have internal passages therethrough for insertion of a guide member (e.g., a guide wire). A kit may include such a guide wire or other guide member.

A variety of medical treatments and procedures may be performed through a paranasal sinus access implant device implanted to provide access to a paranasal sinus. Fluid treatment compositions may be administered to a paranasal sinus through the implant device. Fluid may be aspirated from a paranasal sinus through the implant device. One or more medical devices may be inserted into the paranasal sinus through the implant device.

Some example implementation combinations, which may be the subject of claims with or without additional features as disclosed above, are as follows:

1. A paranasal sinus fluid treatment apparatus, comprising:
 a paranasal sinus access implant device configured to be implanted in a human to provide fluid access to a paranasal sinus, the paranasal sinus access implant device comprising:
  a head configured to be disposed between the medial canthus and the medial side of an adjacent eyeball when the paranasal sinus access implant device is implanted; and
  an internal passage providing fluid access through the paranasal sinus access implant device to a paranasal sinus when the paranasal sinus access implant device is implanted, the internal passage being accessible through an opening in the head;
 a paranasal sinus fluid manipulation tool, the paranasal sinus fluid manipulation tool comprising:
  a fluid container;
  a paranasal sinus fluid connection engagement structure in engagement with the head to fluidly connect the paranasal sinus fluid manipulation tool with the paranasal sinus access implant device, the paranasal sinus fluid connection engagement structure being configured to be disposed in the palpebral fissure;
  a fluid transmission structure configured to transmit fluid between the fluid container and the paranasal sinus access implant device; and
  the paranasal sinus fluid manipulation tool being manipulable to perform at least one of the following fluid manipulations when the paranasal sinus access implant device is implanted to provide fluid access to a paranasal sinus: (i) introduction of fluid from the fluid container into the internal passage for delivery to a paranasal sinus and (ii) applying suction to the internal passage for aspiration of fluid from a paranasal sinus through the internal passage.

2. A paranasal sinus fluid manipulation tool to manipulate fluid through a paranasal sinus access implant device configured to be implanted in a human to provide fluid access to a paranasal sinus through an internal passage of the paranasal sinus access implant device, the internal passage being accessible through an opening in a head of the paranasal sinus access implant device, which head is configured to be disposed between the medial canthus and the medial side of the adjacent eyeball when the paranasal sinus access implant device is implanted to provide fluid access to a paranasal sinus, the paranasal sinus fluid manipulation tool comprising:
 a fluid container;
 a paranasal sinus fluid connection engagement structure configured for insertion into the palpebral fissure to make engagement with the head of a said paranasal sinus access implant device when implanted to fluidly connect the fluid container with the internal passage of the said paranasal sinus access implant device;
 a fluid transmission structure configured to transmit fluid between the fluid container and the paranasal sinus access implant device when the paranasal sinus fluid connection engagement structure is in the engagement with the head of the paranasal sinus access implant device; and
 the paranasal sinus fluid manipulation tool being manipulable to manipulate fluid to perform at least one of the following fluid manipulations when the said paranasal sinus access implant device is implanted and the paranasal sinus fluid connection engagement structure is in the engagement with the head: (i) introducing fluid from the fluid container into the internal passage for delivery from the internal passage to a paranasal sinus and (ii) applying suction to the internal passage for aspiration of fluid from a paranasal sinus through the internal passage and into the fluid container.

3. A kit with one or more components to provide a paranasal sinus fluid manipulation tool to manipulate fluid through a paranasal sinus access implant device configured to be implanted in a human to provide fluid access to a paranasal sinus through an internal passage of the paranasal sinus access implant device, the internal passage being accessible through an opening in a head of the paranasal sinus access implant device, which head is configured to be disposed between the medial canthus and the medial side of the adjacent eyeball when the paranasal sinus access implant device is implanted to provide fluid access to a paranasal sinus, the kit comprising:
 a fluid container;
 a paranasal sinus fluid connection engagement structure configured for insertion into the palpebral fissure to make engagement with the head of a said paranasal sinus access implant device when implanted to fluidly connect the fluid container with the internal passage of the said paranasal sinus access implant device;
 a fluid transmission structure configured to transmit fluid between the fluid container and the paranasal sinus access implant device when the paranasal sinus fluid connection engagement structure is in the engagement with the head of the paranasal sinus access implant device; and the fluid container, the paranasal sinus fluid connection engagement structure and the fluid transmission structure being assembled or assemblable as a paranasal sinus fluid manipulation tool being manipulable to manipulate fluid to perform at least one of the following fluid manipulations when the said paranasal sinus access implant device is implanted and the paranasal sinus fluid connection engagement structure is in the engagement with the head: (i) introducing fluid from the fluid container into the internal passage for delivery from the internal passage to a paranasal sinus and (ii) applying suction to the internal passage for aspiration of fluid from a paranasal sinus through the internal passage and into the fluid container. The paranasal sinus fluid manipulation tool may be according to any one of the example implementation combinations 2 and 16-101.

4. A fluid transmission attachment for use with a syringe to manipulate fluid through a paranasal sinus access implant device configured to be implanted in a human to provide fluid access to a paranasal sinus through an internal passage of the paranasal sinus access implant device, the internal passage being accessible through an opening in a head of the paranasal sinus access implant device, which head is configured to be disposed between the medial canthus and the medial side of the adjacent eyeball when the paranasal sinus access implant device is implanted to provide fluid access to a paranasal sinus, the syringe attachment comprising:

a connection structure configured to connect the fluid transmission attachment with a syringe;

a paranasal sinus fluid connection engagement structure configured for insertion into the palpebral fissure for engagement with the head of a said paranasal sinus access implant device when implanted;

a fluid conduit between the connection structure and the paranasal sinus fluid connection engagement structure to conduct fluid from a fluid container of the syringe to the internal passage of the paranasal sinus access implant device when the syringe and fluid transmission attachment are connected through the connection structure and the paranasal sinus fluid connection engagement structure is in the engagement with the head of the said paranasal sinus access implant device; and the fluid transmission attachment being configured to transmit fluid between the syringe and the internal passage of the said paranasal sinus access implant device as manipulated by the syringe to perform at least one of the following fluid manipulations when the said paranasal sinus access implant device is implanted, the fluid transmission attachment and the syringe are connected through the connection structure and the paranasal sinus fluid connection engagement structure is in the engagement with the head: (i) introducing fluid from the fluid container of the syringe into the internal passage for delivery from the internal passage to a paranasal sinus and (ii) applying suction to the internal passage for aspiration of fluid from a paranasal sinus through the internal passage and into the fluid container of the syringe.

5. A kit, comprising:

a paranasal sinus access implant device configured to be implanted in a human to provide fluid access to a paranasal sinus, the paranasal sinus access implant device comprising:

a head configured to be disposed between the medial canthus and the medial side of an adjacent eyeball when the paranasal sinus access implant device is implanted; and an internal passage providing fluid access through the paranasal sinus access implant device to a paranasal sinus when the paranasal sinus access implant device is implanted, the internal passage being accessible through an opening in the head;

a paranasal sinus fluid manipulation tool or components assemblable into the paranasal sinus fluid manipulation tool, the paranasal sinus fluid manipulation tool comprising:

a fluid container;

a paranasal sinus fluid connection engagement structure configured for insertion into the palpebral fissure for engagement with the head of the paranasal sinus access implant device when the paranasal sinus access implant device is implanted;

a fluid transmission structure configured to transmit fluid between the fluid container and the paranasal sinus access implant device when the paranasal sinus fluid connection engagement structure is in the engagement with the head of the paranasal sinus access implant device; and the paranasal sinus access implant device and the paranasal sinus fluid manipulation tool being configurable to perform at least one of the following fluid manipulations when the paranasal sinus fluid connection engagement structure is in the engagement with the head: (i) introducing fluid from the fluid container into the internal passage and (ii) applying suction to the internal passage for aspiration of fluid from the internal passage. The apparatus sinus access implant device and the paranasal sinus fluid manipulation tool in the kit may be assembled or assemblable as the paranasal sinus fluid treatment apparatus of any one of the example implementation combinations 1 and 16-101.

6. A kit according to either one of example implementation combination 3 or example implementation combination 5, comprising at least one cutting tool for cutting away tissue to form a fistula through which the implant device may be implanted during an implantation procedure.

7. A kit according to example implementation combination 6, wherein the at least one cutting tool comprises a hollow member having a hollow cutting tip at a distal end of the cutting member configured to cut tissue to size the fistula for implantation of the implant device through the fistula.

8. A kit according to either one of example implementation combination 6 or example implementation combination 7, wherein the cutting member has a cutting width that is smaller than a maximum exterior width of a conduit of the implant device configured to be disposed through the fistula during implantation.

9. A kit according to example implementation combination 8, wherein the maximum exterior width of the conduit of the implant device is in a range of from 2.0 to 2.75 millimeters.

10. A kit according to either example implementation combination 8 or example implementation combination 9, wherein the cutting width is not more than 0.75 millimeter smaller than the maximum exterior width of the conduit.

11. A kit according any one of example implementation combinations 8-10, wherein the cutting width is in a range of from 1.5 millimeters to 2.5 millimeters.

12. A kit according to any one of example implementation combinations 3 and 5-11, comprising a carrier tool for carrying the implant device during an implantation procedure, the carrier tool comprising:

a carrier member with a distal tip, the carrier member being adapted to be disposed through a fistula between the lacrimal apparatus in the orbit and a paranasal cavity with the distal tip located in the paranasal cavity; and a hand-manipulable handle connected to the carrier member;

wherein:

the implant device is mountable on the carrier member for implantation with the mounted implant device disposed between the handle and the distal tip with the carrier member disposed through the internal passage and with a proximal end of the implant device disposed toward the handle and a distal end of the implant device disposed toward the distal tip of the member; and when the implant device is mounted for implantation, the carrier is disengageable from the implant device for implant placement of the implant device during an implantation procedure to provide fluid access to a paranasal sinus.

13. A kit according to example implementation combination 12, wherein a clearance fit of the carrier member in the internal passage when the implant device is mounted on the carrier member for implantation is no larger than 0.5 millimeter.

14. A method for manipulating fluid in relation to a paranasal sinus using the fluid treatment apparatus of example implementation combination 1, the method comprising:

with the paranasal sinus access implant device implanted in a human with the head disposed in the orbit of the human, manipulating the fluid manipulation apparatus to perform one of the following manipulations:
(i) introduction of fluid from the fluid container into the internal passage for delivery to the paranasal sinus; and
(ii) applying suction to the internal passage for aspiration of fluid from paranasal passage through the internal passage.

15. A method for manipulating fluid in relation to a paranasal sinus through a paranasal sinus access implant device implanted in a human to provide fluid access to a paranasal sinus through an internal passage of the paranasal sinus access implant device, the internal passage being accessible through an opening in a head of the paranasal sinus access implant device, the head being disposed in an orbit of the human, the method comprising:

engaging a paranasal sinus fluid manipulation tool with the head disposed in the orbit, wherein:
the paranasal sinus fluid manipulation tool comprises:
(i) a fluid container;
(ii) a paranasal sinus fluid connection engagement structure configured for insertion into the palpebral fissure for engagement with the head; and
(iii) a fluid transmission structure configured to transmit fluid between the fluid container and the paranasal sinus access implant device when the paranasal sinus fluid connection engagement structure is in the engagement with the head of the paranasal sinus access implant device; and
the engaging comprises making the engagement of the paranasal sinus fluid connection engagement structure with the head;

after the engaging, manipulating the paranasal sinus fluid manipulation tool to perform one of the following fluid manipulations while the paranasal sinus fluid connection engagement structure is in the engagement with the head: (i) introducing fluid from the fluid container into the internal passage for delivery from the internal passage to a paranasal sinus and (ii) applying suction to the internal passage for aspiration of fluid from a paranasal sinus through the internal passage and into the fluid container.

16. A subject matter according to any one of example implementation combinations 1-15, wherein:

the paranasal sinus fluid connection engagement structure has an insertion cross-section positionable within a first rectangular area having a first length dimension no larger than 12 millimeters and a first width dimension no larger than 8 millimeters; and the insertion cross-section is not positionable in a second rectangular area having a second length dimension of at least 3 millimeters and no larger than the first length dimension and having a second width dimension of at least 1.5 millimeters and smaller than the first width dimension.

17. A subject matter according to example implementation combination 16, wherein the second length dimension is at least 5 millimeters and the second width dimension is at least 2 millimeters.

18. A subject matter according to either one of example implementation combination 16 or example implementation combination 17, wherein the insertion cross-section has an oval shape.

19. A subject matter according to any one of example implementation combinations 16-18, wherein the insertion cross-section has an aspect ratio of length to width of at least 1.5:1.

20. A subject matter according to any one of example implementation combinations 1-19, wherein the paranasal sinus fluid connection engagement structure comprises a receptacle for receiving the head when in the engagement.

21. A subject matter according to example implementation combination 20, wherein the receptacle includes a stop that limits a depth within the receptacle to which the head is receivable in the receptacle in the engagement to no more than 5 millimeters.

22. A subject matter according to either one of example implementation combination 20 or example implementation combination 21, wherein the receptacle has a receiving geometry that is keyed to align with a corresponding geometry of the periphery of the head.

23. A subject matter according to any one of example implementation combinations 20-22, wherein in the engagement clearance fit of the head in the receptacle is no larger than 0.25 millimeter.

24. A subject matter according to any one of example implementation combinations 20-23, wherein the receptacle has an oval geometry and the head has a mating oval geometry received within the receptacle in the engagement.

25. A subject matter according to any one of example implementation combinations 1-24, wherein the paranasal sinus fluid connection engagement structure comprises an insertion stub inserted through the opening into the internal passage in the engagement.

26. A paranasal fluid treatment apparatus according to example implementation combination 25, wherein in the engagement clearance fit between the insertion stub in the internal passage is no larger than 0.25 millimeter.

27. A subject matter according to either one of example implementation combination 25 or example implementation combination 26, wherein in the engagement the insertion stub does not extend beyond a distal end of the internal passage.

28. A subject matter according to any one of example implementation combinations 1-27, wherein in the engagement the paranasal sinus fluid connection engagement structure and the head are in surface contact around the entire periphery of the opening.

29. A subject matter according to any one of example implementation combinations 1-28, wherein in the engagement the paranasal sinus fluid connection engagement structure and the head contact to form a fluid seal therebetween.

30. A subject matter according to any one of example implementation combinations 1-29, wherein in the engagement no portion of the paranasal sinus fluid manipulation tool extends through the opening in the head.

31. A subject matter according to any one of example implementation combinations 1-30, wherein in the engagement at least a portion of the paranasal sinus fluid manipulation tool is disposed exterior to the paranasal sinus access implant device and distal to a proximal end of the paranasal sinus access implant device.

32. A subject matter according to any one of example implementation combinations 1-31, wherein the paranasal sinus fluid connection engagement structure includes a contact surface that is in contact with the head in the engagement and the contact surface is of a material having a durometer of no larger than Shore D 100.

33. A subject matter according to example implementation combination 32, wherein the durometer of the material is not smaller than Shore A 30.

34. A subject matter according to either one of example implementation combination 32 or example implementation combination 33, wherein the material is a polymeric material.

35. A paranasal fluid treatment apparatus according to example implementation combination 34, wherein the polymeric material comprises a silicone composition.

36. A paranasal fluid treatment apparatus according to example implementation combination 34, wherein the polymeric material comprises a polyurethane composition.

37. A subject matter according to example implementation combination 34, wherein the polymeric material comprises a polyolefin composition.

38. A subject matter according to example implementation combination 34, wherein the polymeric material comprises an elastomeric composition.

39. A subject matter according to either one of example implementation combination 32 or example implementation combination 33, wherein the material is a rubber material.

40. A subject matter according to any one of example implementation combinations 1-39, wherein all surfaces of the paranasal sinus fluid connection engagement structure that contact the head in the engagement are of the same material.

41. A subject matter according to any one of example implementation combinations 1-40, wherein the fluid container comprises at least a portion of a barrel of a syringe, the syringe including a piston disposed within the barrel that is manipulable to manipulate fluid in the fluid container.

42. A subject matter according to example implementation combination 41, wherein the paranasal sinus fluid connection engagement structure is on a distal portion of a fluid transmission attachment connected with the syringe; and the fluid transmission structure comprises a fluid conduit in fluid communication with the fluid container and the internal passage.

43. A subject matter according to example implementation combination 42, wherein the fluid transmission attachment is connected with the syringe through a luer connection.

44. A subject matter according to any one of example implementation combinations 1-43, wherein;

the head is disposed adjacent a proximal end of the paranasal sinus access implant device;

the paranasal sinus access implant device has a distal end at a longitudinal end opposite the proximal end; and in the engagement, no portion of the paranasal sinus fluid manipulation tool extends distal of the distal end of the paranasal sinus access implant device.

45. A subject matter according to any one of example implementation combinations 1-44, comprising a fluid treatment composition disposed within the fluid container.

46. A subject matter according to example implementation combination 45, wherein the treatment composition is an aqueous irrigation liquid.

47. A subject matter according to example implementation combination 45, wherein the treatment composition is a drug treatment composition.

48. A subject matter according to example implementation combination 47, wherein the drug treatment composition comprises at least one drug for treating sinusitis.

49. A subject matter according to either one of example implementation combination 47 or example implementation combination 48, wherein the drug treatment composition comprises an antibiotic.

50. A subject matter according to any one of example implementation combinations 47-49, wherein the drug treatment composition comprises a steroid.

51. A subject matter according to any one of example implementation combinations 47-50, wherein the drug treatment composition comprises an anti-viral.

52. A subject matter according to any one of example implementation combinations 47-51, wherein the drug treatment composition comprises an antihistamine.

53. A subject matter according to any one of example implementation combinations 47-52, wherein the drug treatment composition comprises an anti-fungal.

54. A subject matter according to any one of example implementation combinations 47-53, wherein the drug treatment composition comprises a mast cell stabilizer.

A subject matter according to any one of example implementation combinations 47-54, wherein the drug treatment composition comprises a mucolytic.

56. A subject matter according to any one of example implementation combinations 47-55, wherein the drug treatment composition comprises a non-steroidal anti-inflammatory drug (NSAID).

57. A subject matter according to any one of example implementation combinations 47-56, wherein the drug treatment composition comprises a vasoconstrictor.

58. A subject matter according to any one of example implementation combinations 47-57, wherein the drug treatment composition comprises an immunosuppressant.

59. A subject matter according to any one of example implementation combinations 45-58, wherein the fluid container contains a volume of the treatment composition in a range of from 0.1 milliliter to 3 milliliters.

60. A subject matter according to any one of example implementation combinations 1-59, wherein the paranasal sinus access implant device comprises:

a proximal end at a first longitudinal end, the head being adjacent the proximal end;

a distal end at a second longitudinal end that is longitudinally opposite the first longitudinal end;

a conduit disposed between the head and the distal end, the internal passage extending through the head and the conduit;

a length longitudinally along the paranasal sinus access implant device between the proximal end and the distal end in a range of from 2 millimeters to 50 millimeters;

a width of the internal passage transverse to the length of the paranasal sinus access implant device in a range of from 0.25 millimeter to 5 millimeters; and the paranasal sinus access implant device is configured to be implanted between the lacrimal apparatus in the orbit and a paranasal sinus, wherein when so implanted the proximal end is disposed in the lacrimal apparatus within the orbit and the distal end is disposed in the paranasal sinus.

61. A subject matter according to example implementation combination 60, wherein:

the conduit includes a first longitudinal portion and a second longitudinal portion located toward the distal end relative to the first longitudinal portion;

the first longitudinal portion of the conduit has a first minimum wall thickness adjacent the internal passage;

the second longitudinal portion of the conduit has a second minimum wall thickness adjacent the internal passage that is smaller than the first minimum wall thickness; and the paranasal sinus access implant device is configured to be implanted between the lacrimal apparatus in the orbit and a paranasal sinus, wherein when so implanted at least a portion of each of the first longitudinal portion and the second longitudinal portion of the conduit are disposed across tissue between the lacrimal apparatus in the orbit and the paranasal sinus and at least a portion of the second longitudinal portion of the conduit is disposed in the paranasal sinus.

62. A subject matter according to example implementation combination 61, wherein the first longitudinal portion of the conduit has a uniform wall thickness.

63. A subject matter according to either one of example implementation combination 61 or example implementation combination 62, wherein the first longitudinal portion of the conduit has a smooth exterior surface.

64. A subject matter according to any one of example implementation combinations 61-63, wherein the first longitudinal portion of the conduit has a length of at least 5 millimeters.

65. A subject matter according to any of example implementation combinations 61-64, wherein the first longitudinal portion of the conduit has a length of no greater than 15 millimeters.

66. A subject matter according to any one of example implementation combinations 61-65, wherein the first minimum wall thickness is at least 0.35 millimeter.

67. A subject matter according to any one of example implementation combinations 61-66, wherein the first minimum wall thickness is no greater than 0.55 millimeter.

68. A subject matter according to any one of example implementation combinations 61-67, wherein the second longitudinal portion of the conduit has a length of at least 5 millimeters.

69. A subject matter according to any one of example implementation combinations 61-68, wherein the second longitudinal portion of the conduit has a length of no greater than 15 millimeters.

70. A subject matter according to any one of example implementation combinations 61-69, wherein the second minimum wall thickness is no greater than 0.35 millimeter.

71. A subject matter according to any one of example implementation combinations 61-70, wherein the second minimum wall thickness is at least 0.15 millimeter.

72. A subject matter according to any one of example implementation combinations 61-71, wherein the first minimum wall thickness is at least 0.05 millimeter larger than the second minimum wall thickness.

73. A subject matter according to any one of example implementation combinations 61-72, wherein the first longitudinal portion of the conduit has a first maximum exterior width that is smaller than a second maximum exterior width of the second longitudinal portion of the conduit.

74. A subject matter according to example implementation combination 73, wherein the second maximum exterior width is at least 0.2 millimeters larger than the first maximum exterior width.

75. A subject matter according to either one of example implementation combination 73 or example implementation combination 74, wherein the first maximum exterior width is in a range of from 1.5 millimeters to 2.5 millimeters.

76. A subject matter according to any one of example implementation combinations 73-75, wherein:

the first longitudinal portion of the conduit has a first minimum exterior width and the second longitudinal portion of the conduit has a second minimum exterior width; and the second minimum exterior width is smaller than the first maximum exterior width.

77. A subject matter according to example implementation combination 76, wherein the first minimum exterior width is larger than the second minimum exterior width.

78. A subject matter according to example implementation combination 77, wherein:

the first maximum exterior width and the first minimum exterior width are each within a range of from 1.5 millimeters to 2.5 millimeters;

the second maximum exterior width is in a range of from 1.6 millimeters to 3 millimeters;

the second minimum exterior width is in a range of from 1 millimeter to 2 millimeters;

the first minimum exterior width is at least 0.1 millimeter larger than the second minimum exterior width;

the second maximum exterior width is at least 0.2 millimeter larger than the first maximum exterior width.

79. A subject matter according to any one of example implementation combinations 76-78, wherein the first minimum exterior width and the first maximum exterior width are equal.

80. A subject matter according to any one of example implementation combinations 61-79, wherein the conduit has a circular cross-section at all points along the length of the first and second longitudinal portions of the conduit.

81. A subject matter according to any one of example implementation combinations 61-80, wherein an exterior of the second longitudinal portion of the conduit includes an anchoring surface feature including protrusion areas and recess areas.

82. A subject matter according to example implementation combination 81, wherein the protrusion areas are on a longitudinal portion of the second longitudinal portion of the conduit extending at least 5 millimeters along the length of the device.

83. A subject matter according to either one of example implementation combination 81 or example implementation combination 82, wherein the first longitudinal portion of the conduit is in the absence of the anchoring surface feature.

84. A subject matter according to any one of example implementation combinations 81-83, wherein the protrusion areas cover no more than 30 percent of the area along the longitudinal portion of the second longitudinal portion of the conduit.

85. A subject matter according to any one of example implementation combinations 81-84, wherein the protrusion areas comprise at least 2 spaced circumferential ridges, with each said circumferential ridge extending around an entire circumference of the conduit.

86. A subject matter according to any one of example implementation combinations 1-82, wherein the head comprises a flanged tissue engagement surface on a side of the head disposed toward the conduit and configured to engage tissue exposed in the orbit when the paranasal sinus access implant device is implanted.

87. A subject matter according to example implementation combination 86, wherein the head has a second dimension transverse to the first dimension that is a maximum separation distance between points on the outer edge that are on a line transverse to the first dimension, and a ratio of the first dimension to the second dimension is at least 1.5.

88. A subject matter according to example implementation combination 87, wherein the ratio of the first dimension to the second dimension is no greater than 4.

89. A subject matter according to any one of example implementation combinations 1-7, 14 and 15, wherein:

the paranasal sinus fluid connection engagement structure has an insertion cross-section having an aspect ratio of length to width of at least 1.5, being positionable within a first rectangular area having a first length dimension of 12 millimeters and a first width dimension of 8 millimeters, and being not positionable within a second rectangular area having a second length dimension of 5 millimeters and a second width dimension of 2 millimeters.

90. A subject matter according to example implementation combination 89, wherein:

the paranasal sinus fluid connection engagement structure comprises a receptacle for receiving the head;

the receptacle includes a stop that limits a depth within the receptacle to which the head is receivable in the receptacle to no more than 5 millimeters in the engagement; and the receptacle has a receiving geometry that is keyed to align with a corresponding geometry of the periphery of the head in the engagement.

91. A subject matter according to example implementation combination 90, wherein the receptacle has an oval geometry and the head has a mating oval geometry received within the receptacle in the engagement.

92. A subject matter according to example implementation combination 91, wherein in the engagement the paranasal sinus fluid connection engagement structure and the head are in flush surface contact around the entire periphery of the opening.

93. A subject matter according to example implementation combination 89, comprising a drug treatment composition disposed in the fluid container.

94. A subject matter according to example implementation combination 93, wherein the drug treatment composition comprises at least two members selected from the group consisting of an antibiotic, a steroid, an anti-fungal, an anti-viral and an antihistamine.

95. A subject matter according example implementation combination 89, wherein the paranasal sinus fluid connection engagement structure includes a contact surface that is in contact with the head in the engagement and the contact surface is of a polymeric material having a durometer of no larger than Shore A 100.

96. A subject matter according to example implementation combination 90, wherein:

the paranasal sinus access implant device comprises a conduit adjacent the head;

the head comprises a flanged tissue engagement surface on a side of the head disposed toward the conduit and configured to engage tissue when the paranasal sinus access implant device is implanted;

the flanged tissue engagement surface comprises an outer edge;

the head has a first dimension that is a maximum separation distance between points on the outer edge of the flanged tissue engagement surface, the first dimension being larger than the exterior width of the conduit;

the head has a second dimension that is a maximum separation distance between points on the outer edge that are on a line transverse to the first dimension;

the second dimension is not larger than an exterior width of the conduit;

a ratio of the first dimension to the second dimension is in a range of from 2 to 4;

the first dimension is in a range of from 4 to 10 millimeters;

the second dimension is in a range of from 1.5 millimeters to 4 millimeters; and a ratio of the first dimension to the second dimension is at least 1.5.

97. A subject matter according to example implementation combination 89, wherein the paranasal sinus access implant device comprises:

a proximal end at a first longitudinal end, the head being adjacent the proximal end;

a distal end at a second longitudinal end that is longitudinally opposite the first longitudinal end;

a conduit disposed between the head and the distal end, the internal passage extending through the head and the conduit;

a length longitudinally along the paranasal sinus access implant device between the proximal end and the distal end in a range of from 2 millimeters to 50 millimeters;

a width of the internal passage transverse to the length of the paranasal sinus access implant device in a range of from 0.25 millimeter to 5 millimeters;

the conduit including a first longitudinal portion and a second longitudinal portion located toward the distal end relative to the first longitudinal portion;

the first longitudinal portion of the conduit having a first minimum wall thickness adjacent the internal passage;

the second longitudinal portion of the conduit having a second minimum wall thickness adjacent the internal passage that is smaller than the first minimum wall thickness; and the paranasal sinus access implant device is configured to be implanted between the lacrimal apparatus in the orbit and a paranasal sinus, wherein when so implanted:

the proximal end is disposed in the lacrimal apparatus within the orbit;

the distal end is disposed in the paranasal sinus; and at least a portion of each of the first longitudinal portion and the second longitudinal portion of the conduit are disposed across tissue between the lacrimal apparatus in the orbit and the paranasal sinus and at least a portion of the second longitudinal portion of the conduit is disposed in the paranasal sinus.

98. A subject matter according to example implementation combination 97, wherein:

the first longitudinal portion of the conduit has a length of at least 5 millimeters;

the second longitudinal portion of the conduit has a length of at least 5 millimeters;

the second longitudinal portion of the conduit has a minimum exterior width at a location corresponding with the second minimum wall thickness;

the second longitudinal portion of the conduit has a maximum exterior width that is larger than the minimum exterior width of the second longitudinal portion of the conduit; and the first longitudinal portion of the conduit has a maximum exterior width that is smaller than the maximum exterior width of the second longitudinal portion of the conduit.

99. A subject matter according to example implementation combination 98, wherein:

the first maximum exterior width and the first minimum exterior width are each within a range of from 1.5 millimeters to 2.5 millimeters;

the second maximum exterior width is in a range of from 1.6 millimeters to 3 millimeters;

the second minimum exterior width is in a range of from 1 millimeter to 2 millimeters;

the first minimum exterior width is at least 0.1 millimeter larger than the second minimum exterior width; and the second maximum exterior width is at least 0.2 millimeter larger than the first maximum exterior width.

100. A subject matter according to example implementation combination 99, wherein the first longitudinal portion of the conduit has an exterior width equal to the maximum exterior width along the entire length of the first longitudinal portion of the conduit.

101. A subject matter according to example implementation combination 100, wherein an exterior of the second longitudinal portion of the conduit includes an anchoring surface feature including protrusion areas and recess areas, and wherein the second minimum wall thickness occurs at a location corresponding with at least one of the recess areas.

A "subject matter" as referenced in the foregoing example implementation combinations may be a paranasal sinus fluid treatment apparatus, fluid manipulation tool, kit, fluid transmission attachment or method, as the case may be.

The various apparatuses, devices, tools and kits, and the various example implementation combinations, disclosed herein are described with reference primarily to access to and applications directed to a paranasal sinus, but the apparatuses, devices, tools, kits and example implementation combinations are also useful in relation to access to and applications directed to a nasal cavity, notwithstanding identification of such apparatuses, devices, tools and kits in relation to a paranasal sinus. In that regard, as noted above a paranasal sinus fluid treatment apparatus may be referred to herein as simply a fluid treatment apparatus, a paranasal sinus access implant device may be referred to as simply an implant device, a paranasal sinus fluid manipulation tool may be referred to as simply a fluid manipulation tool, and a paranasal sinus fluid connection engagement structure may be referred to as simply a fluid connection engagement structure. The implant device is also implantable in a fistula that may be formed between the lacrimal apparatus (e.g., from the corner of medial portion of the orbit between the lacrimal caruncle and the plica semilunaris) and the nasal cavity, for example for enhanced drainage of lacrimal fluid and/or to provide access to the nasal cavity for medical procedures or fluid manipulations, and such applications directed to the nasal cavity are within the scope of the different aspects of the disclosure. The methods disclosed herein may alternatively involve an implant device implanted to fluidly connect a location in the lacrimal apparatus and a nasal cavity rather than to a paranasal sinus, with a proximal end of the implant device disposed in the lacrimal apparatus and a distal end of the implant device disposed in the nasal cavity and with an internal passage through the implant device opening into the lacrimal apparatus and the nasal cavity. The methods disclosed herein may alternatively include fluid manipulations directed to a nasal cavity, rather than a paranasal sinus, through an implant device so implanted to fluidly connect the lacrimal apparatus and the nasal cavity, for example to provide fluid access to the nasal cavity to perform at least one of the following fluid manipulations through the internal passage of the implant device: (i) introduction of fluid from a fluid container into the internal passage for delivery to a nasal cavity and (ii) applying suction to the internal passage for aspiration of fluid from a nasal cavity.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are not necessarily technically incompatible, and all such combinations are within the scope of the present invention.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, a statement that some thing "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term "at least a portion" means all or a portion that is less than all. The term "at least a part" means all or a part that is less than all.

The features in the drawings are shown for illustration purposes and to generally show relative positioning and interaction, and the features shown are not necessarily to scale.

What is claimed is:

1. A paranasal sinus fluid treatment apparatus, comprising:
   a paranasal sinus access implant device configured to be implanted in a human to provide fluid access to a paranasal sinus, the paranasal sinus access implant device comprising:
      a head configured to be disposed between the medial canthus and the medial side of an adjacent eyeball when the paranasal sinus access implant device is implanted; and
      an internal passage providing fluid access through the paranasal sinus access implant device to a paranasal sinus when the paranasal sinus access implant device is implanted, the internal passage being accessible through an opening in the head;
   a paranasal sinus fluid manipulation tool, the paranasal sinus fluid manipulation tool comprising:
      a fluid container;
      a paranasal sinus fluid connection engagement structure in engagement with the head with the paranasal sinus fluid connection engagement structure and the head in surface contact around the entire periphery of the opening in the head to fluidly connect the paranasal sinus fluid manipulation tool with the paranasal sinus access implant device, the paranasal sinus fluid connection engagement structure being configured to be disposed in the palpebral fissure;
      a fluid transmission structure configured to transmit fluid between the fluid container and the internal passage of the paranasal sinus access implant device, the fluid transmission structure having a fluid transmission opening within the internal passage or proximal to the internal passage and through which fluid is transmitted between the fluid transmission structure and the internal passage; and
   the paranasal sinus fluid manipulation tool being manipulable to perform at least one of the following fluid manipulations when the paranasal sinus access implant device is implanted to provide fluid access to a paranasal sinus: (i) introduction of fluid from the fluid container through the fluid transmission opening into the internal passage for delivery of the introduced fluid from the internal passage to a paranasal sinus and (ii) applying suction to the internal passage through the fluid transmission opening for aspiration of fluid from the internal passage for removal of fluid from a paranasal sinus through the internal passage.

2. An apparatus according to claim 1, wherein:
   the paranasal sinus fluid connection engagement structure has an insertion cross-section positionable within a first rectangular area having a first length dimension no larger than 7 millimeters and a first width dimension no larger than 7 millimeters; and
   the insertion cross-section is not positionable in a second rectangular area having a second length dimension of at least 3 millimeters and no larger than the first length dimension and having a second width dimension of at least 2.5 millimeters and smaller than the first width dimension.

3. An apparatus according to claim 1, wherein the paranasal sinus fluid connection engagement structure comprises a receptacle for receiving the head when in the engagement; and
   the receptacle includes a stop that limits a depth within the receptacle to which the head is receivable in the receptacle in the engagement to no more than 5 millimeters.

4. An apparatus according to claim 3, wherein in the engagement clearance fit of the head in the receptacle is no larger than 0.25 millimeter.

5. An apparatus according to claim 1, wherein the paranasal sinus fluid connection engagement structure comprises an insertion stub inserted through the opening in the head into the internal passage in the engagement.

6. An apparatus according to claim 1, wherein in the engagement no portion of the paranasal sinus fluid manipulation tool extends beyond a distal end of the internal passage.

7. An apparatus according to claim 1, wherein in the engagement the paranasal sinus fluid connection engagement structure and the head contact to form a fluid seal therebetween.

8. An apparatus according to claim 1, wherein in the engagement no portion of the paranasal sinus fluid manipulation tool extends through the opening in the head.

9. An apparatus according to claim 1, wherein in the engagement at least a portion of the paranasal sinus fluid manipulation tool is disposed exterior to the paranasal sinus access implant device and distal to a proximal end of the paranasal sinus access implant device.

10. An apparatus according to claim 1, wherein the fluid container comprises at least a portion of a barrel of a syringe, the syringe including a piston disposed within the barrel that is manipulable to manipulate fluid in the fluid container.

11. An apparatus according to claim 10, wherein the paranasal sinus fluid connection engagement structure is on a distal portion of a fluid transmission attachment connected with the syringe; and
   the fluid transmission structure comprises a fluid conduit in fluid communication with the fluid container and the internal passage.

12. An apparatus according to claim 1, comprising a fluid treatment composition disposed within the fluid container.

13. An apparatus according to claim 12, wherein the treatment composition is an aqueous irrigation liquid.

14. An apparatus according to claim 12, wherein the treatment composition is a drug treatment composition.

15. An apparatus according to claim 14, wherein the drug treatment composition comprises at least one drug for treating sinusitis.

16. An apparatus according to claim 14, wherein the drug treatment composition comprises at least two members selected from the group consisting of an antibiotic, a steroid, an anti-fungal, an anti-viral and an antihistamine.

17. A paranasal sinus fluid treatment apparatus, comprising:
   a paranasal sinus access implant device configured to be implanted in a human to provide fluid access to a paranasal sinus, the paranasal sinus access implant device comprising:
      a head configured to be disposed between the medial canthus and the medial side of an adjacent eyeball when the paranasal sinus access implant device is implanted; and an internal passage providing fluid access through the paranasal sinus access implant device to a paranasal sinus when the paranasal sinus access implant device is implanted, the internal passage being accessible through an opening in the head;

a proximal end at a first longitudinal end, the head being adjacent the proximal end;

a distal end at a second longitudinal end that is longitudinally opposite the first longitudinal end;

a conduit disposed between the head and the distal end, the internal passage extending through the head and the conduit;

a length longitudinally along the paranasal sinus access implant device between the proximal end and the distal end in a range of from 8 millimeters to 50 millimeters;

a width of the internal passage transverse to the length of the paranasal sinus access implant device in a range of from 0.25 millimeter to 5 millimeters;

the conduit includes a first longitudinal portion and a second longitudinal portion located toward the distal end relative to the first longitudinal portion;

the first longitudinal portion of the conduit having a length of at least 3 millimeters extending from a proximal end of the first longitudinal portion of the conduit adjacent the head to a distal end of the first longitudinal portion of the conduit disposed toward a proximal end of the second longitudinal portion of the conduit;

the first longitudinal portion of the conduit has a first minimum wall thickness adjacent the internal passage;

an exterior of the second longitudinal portion of the conduit having an anchoring surface feature including anchor protrusions spaced along a length of the second longitudinal portion of the conduit and recess areas between the anchor protrusions, wherein the length of the second longitudinal portion of the conduit is at least 3 millimeters extending from a proximal end of the second longitudinal portion of the conduit at a said anchor protrusion closest to the head to a distal end of the second longitudinal portion of the conduit at a said anchor protrusion farthest from the head;

the second longitudinal portion of the conduit has a second minimum wall thickness adjacent the internal passage that is smaller than the first minimum wall thickness, wherein the second minimum wall thickness is at a said recess area; and the paranasal sinus access implant device is configured to be implanted between the lacrimal apparatus in the orbit and a paranasal sinus, wherein when so implanted at least a portion of each of the first longitudinal portion and the second longitudinal portion of the conduit are disposed across tissue between the lacrimal apparatus in the orbit and the paranasal sinus and at least a portion of the second longitudinal portion of the conduit is disposed in the paranasal sinus a paranasal sinus fluid manipulation tool, the paranasal sinus fluid manipulation tool comprising:

a fluid container;

a paranasal sinus fluid connection engagement structure in engagement with the head with the paranasal sinus fluid connection engagement structure and the head in surface contact around the entire periphery of the opening to fluidly connect the paranasal sinus fluid manipulation tool with the paranasal sinus access implant device, the paranasal sinus fluid connection engagement structure being configured to be disposed in the palpebral fissure;

a fluid transmission structure configured to transmit fluid between the fluid container and the paranasal sinus access implant device; and the paranasal sinus fluid manipulation tool being manipulable to perform at least one of the following fluid manipulations when the paranasal sinus access implant device is implanted to provide fluid access to a paranasal sinus: (i) introduction of fluid from the fluid container into the internal passage for delivery to a paranasal sinus and (ii) applying suction to the internal passage for aspiration of fluid from a paranasal sinus through the internal passage.

18. An apparatus according to claim 17, wherein the first longitudinal portion of the conduit has a length in a range of from 5 millimeters to 15 millimeters and the second longitudinal portion of the conduit has a length in a range of from 5 millimeters to 15 millimeters; and the first minimum wall thickness is at least 0.35 millimeter and is at least 0.05 millimeter larger than the second minimum wall thickness.

19. An apparatus according to claim 18, wherein the first longitudinal portion of the conduit has a first maximum exterior width that is smaller than a second maximum exterior width of the second longitudinal portion of the conduit;

the second maximum exterior width is at least 0.2 millimeters larger than the first maximum exterior width;

the first maximum exterior width is in a range of from 1.5 millimeters to 2.5 millimeters;

the first longitudinal portion of the conduit has a first minimum exterior width and the second longitudinal portion of the conduit has a second minimum exterior width;

the second minimum exterior width is smaller than the first maximum exterior width;

the first minimum exterior width is larger than the second minimum exterior width;

the first maximum exterior width and the first minimum exterior width are each within a range of from 1.5 millimeters to 2.5 millimeters;

the second maximum exterior width is in a range of from 1.75 millimeters to 3 millimeters;

the second minimum exterior width is in a range of from 1 millimeter to 2 millimeters;

the first minimum exterior width is at least 0.1 millimeter larger than the second minimum exterior width; and the second maximum exterior width is at least 0.2 millimeter larger than the first maximum exterior width.

20. An apparatus according to claim 19, wherein the first longitudinal portion of the conduit is in the absence of the anchoring surface feature.

* * * * *